(12) United States Patent
Miller et al.

(10) Patent No.: US 6,690,004 B2
(45) Date of Patent: Feb. 10, 2004

(54) METHOD AND APPARATUS FOR ELECTROSPRAY-AUGMENTED HIGH FIELD ASYMMETRIC ION MOBILITY SPECTROMETRY

(75) Inventors: Raanan A. Miller, Brookline, MA (US); Erkinjon G. Nazarov, Lexington, MA (US); Gary A. Eiceman, Las Cruces, NM (US); Evgeny Krylov, Las Cruces, NM (US)

(73) Assignee: The Charles Stark Draper Laboratory, Inc., Cambridge, MA (US)

(*) Notice: Subject to any disclaimer, the term of this patent is extended or adjusted under 35 U.S.C. 154(b) by 0 days.

(21) Appl. No.: 10/123,030

(22) Filed: Apr. 12, 2002

(65) Prior Publication Data

US 2003/0146377 A1 Aug. 7, 2003

Related U.S. Application Data

(63) Continuation-in-part of application No. 10/040,974, filed on Jan. 7, 2002, now abandoned, and a continuation-in-part of application No. 09/358,312, filed on Jul. 21, 1999, now Pat. No. 6,495,823, and a continuation-in-part of application No. 09/439,543, filed on Nov. 12, 1999, now Pat. No. 6,512,224, and a continuation-in-part of application No. 09/799,223, filed on Mar. 5, 2001.

(51) Int. Cl.⁷ .............................................. B01D 59/44
(52) U.S. Cl. ...................... 250/286; 250/287; 250/282; 250/288
(58) Field of Search ........................... 250/286, 287, 250/282, 288

(56) References Cited

U.S. PATENT DOCUMENTS

| | | |
|---|---|---|
| 2,615,135 A | 10/1952 | Glenn |
| 2,818,507 A | 12/1957 | Britten |
| 2,919,348 A | 12/1959 | Bierman |
| 3,511,986 A | 5/1970 | Llewellyn |
| 3,619,605 A | 11/1971 | Cook et al. |
| 3,621,240 A | 11/1971 | Cohen et al. |
| 3,648,046 A | 3/1972 | Denison et al. |
| 4,019,989 A | 4/1977 | Hazewindus et al. |
| 4,163,151 A | 7/1979 | Bayless et al. |
| 4,167,668 A | 9/1979 | Mouriér |
| 4,315,153 A | 2/1982 | Vahrenkamp |
| 4,517,462 A | 5/1985 | Boyer et al. |
| 4,761,545 A | 8/1988 | Marshall et al. |
| 4,885,500 A | 12/1989 | Hansen et al. |
| 4,931,640 A | 6/1990 | Marshall et al. |
| 5,019,706 A | 5/1991 | Allemann et al. |
| 5,047,723 A | 9/1991 | Puumalainen |

(List continued on next page.)

FOREIGN PATENT DOCUMENTS

| | | |
|---|---|---|
| WO | WO 9738302 | 10/1997 |
| WO | WO 9921212 | 4/1999 |
| WO | WO 00/08455 | 2/2000 |
| WO | WO 0108197 A1 | 2/2001 |
| WO | WO 01/69647 A2 | 9/2001 |

OTHER PUBLICATIONS

Guevremont et al., "Tandem High Field Asymmetric Waveform Ion Mobility Spectrometry" (FAIMS), Pub. No: US 2003/0089847 A1, Pub. Date: May 15, 2003.*
E. Krylov, "A method of reducing diffusion losses in a drift spectrometer," *Technical Physics*, V.44:1, pp. 113–116.
R. Guevremont, et al., "Atmospheric pressure ion focusing in a high–field asymmetric waveform ion mobility spectrometer," *Review of Scientific Instruments*, V.70:2, pp. 1370–1383.

*Primary Examiner*—John R. Lee
*Assistant Examiner*—Zia R. Hashmi
(74) *Attorney, Agent, or Firm*—Hamilton, Brook, Smith and Reynolds, P.C.

(57) ABSTRACT

Method and apparatus for the analysis of compounds using electrospray in high field asymmetric ion mobility spectrometry.

99 Claims, 33 Drawing Sheets

U.S. PATENT DOCUMENTS

| | | |
|---|---|---|
| 5,144,127 A | 9/1992 | Williams et al. |
| 5,298,745 A | 3/1994 | Kernan et al. |
| 5,373,157 A | 12/1994 | Hiroki et al. |
| 5,492,867 A | 2/1996 | Kotvas et al. |
| 5,541,408 A | 7/1996 | Sittler |
| 5,644,131 A | 7/1997 | Hansen |
| 5,654,544 A | 8/1997 | Dresch |
| 5,811,059 A | 9/1998 | Genovese et al. |
| 5,838,003 A | 11/1998 | Bertsch et al. |
| 5,852,302 A | 12/1998 | Hiraishi et al. |
| 6,049,052 A | 4/2000 | Chutjian et al. |
| 6,066,848 A | 5/2000 | Kassel et al. |
| 6,124,592 A | 9/2000 | Spangler |
| 6,157,029 A | 12/2000 | Chutjian et al. |
| 6,157,031 A | 12/2000 | Prestage |
| 6,188,067 B1 | 2/2001 | Chutjian et al. |
| 6,262,416 B1 | 7/2001 | Chutjian et al. |
| 6,281,494 B1 | 8/2001 | Chutjian et al. |
| 2001/0030285 A1 | 10/2001 | Miller et al. |

* cited by examiner

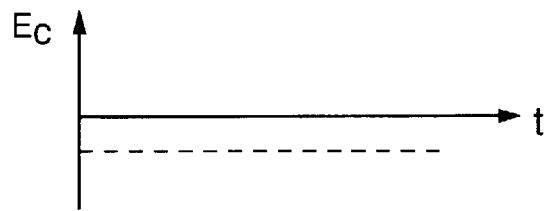
**FIG. 1D1
(PRIOR ART)**
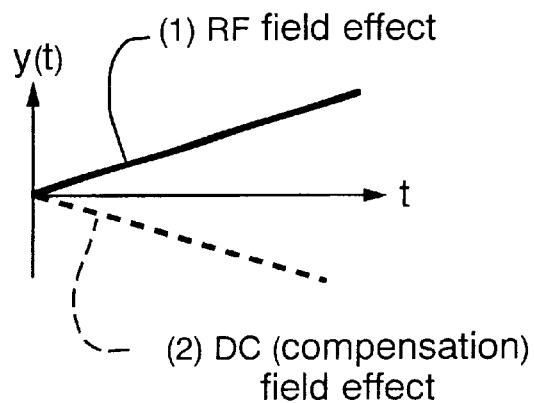
**FIG. 1D2
(PRIOR ART)**
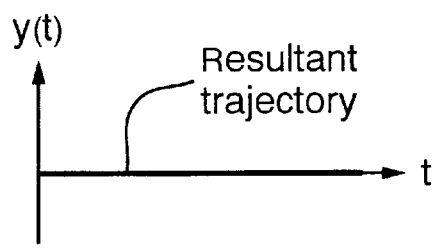
**FIG. 1D3
(PRIOR ART)**

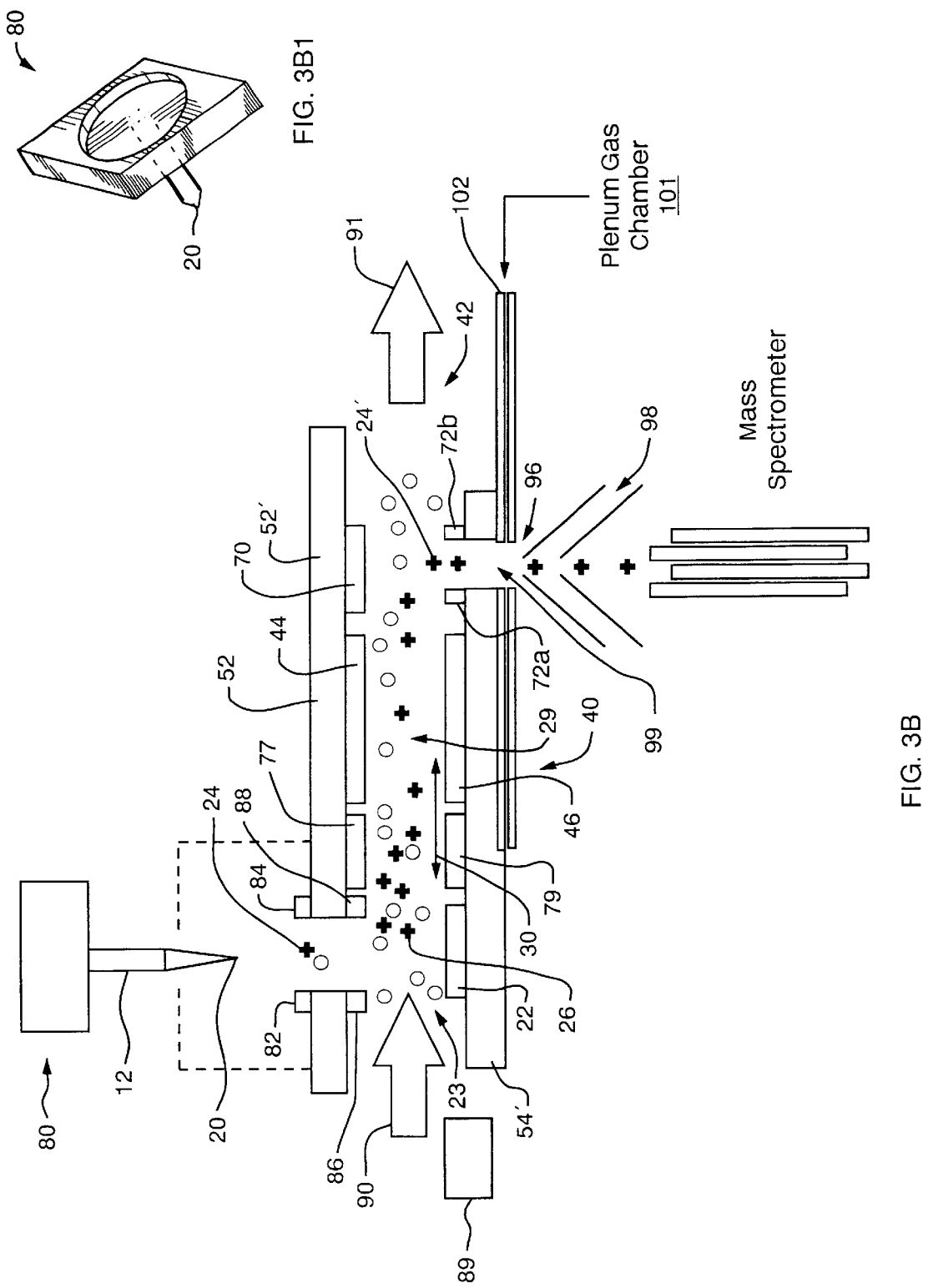

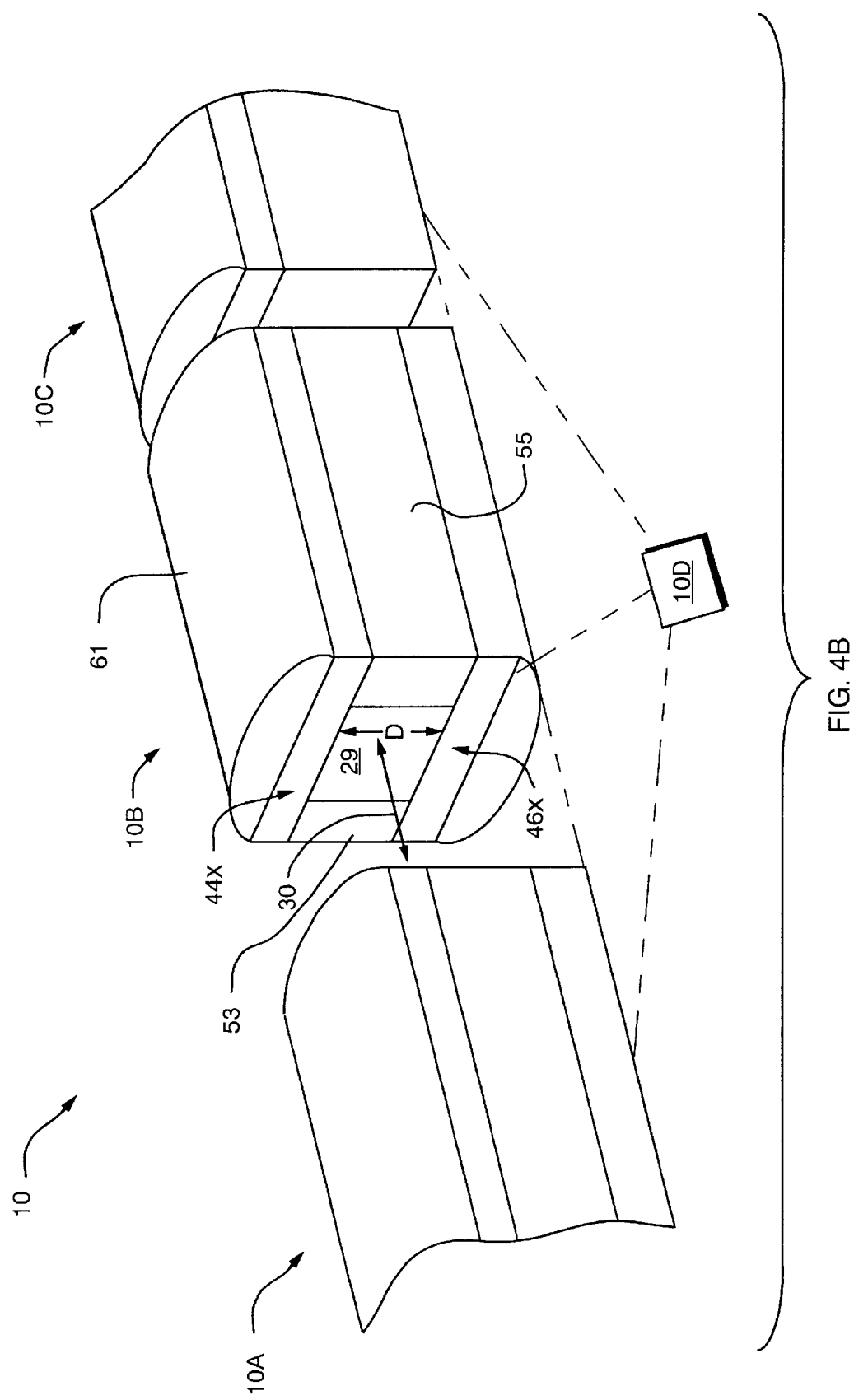

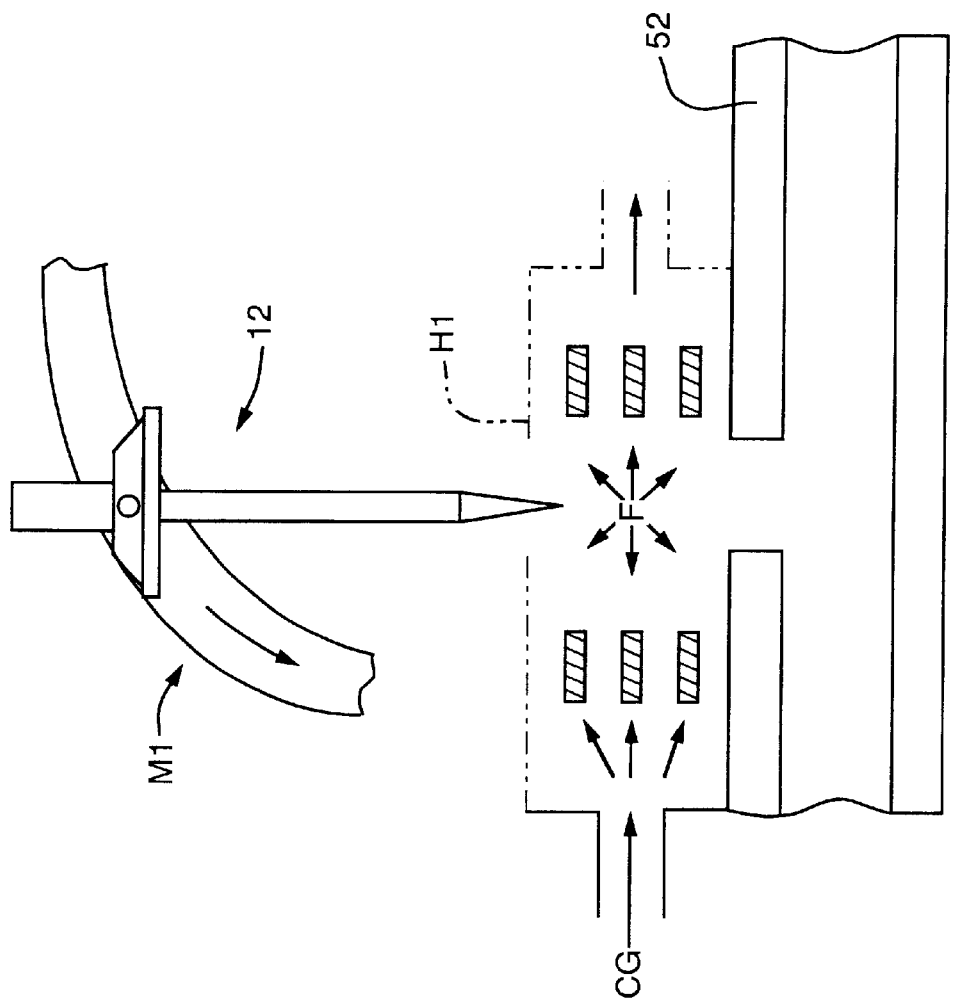

METHOD AND APPARATUS FOR ELECTROSPRAY-AUGMENTED HIGH FIELD ASYMMETRIC ION MOBILITY SPECTROMETRY

RELATED APPLICATION(S)

This application is a continuation in part of the following applications: U.S. application Ser. No. 09/358,312, filed Jul. 21, 1999 now U.S. Pat. No. 6,495,823, U.S. application Ser. No. 09/439,543, filed Nov. 12, 1999 now U.S. Pat. No. 6,512,224, U.S. application Ser. No.09/799,223, filed, Mar. 5, 2001, and U.S. application Ser. No. 10/040,974, filed Jan. 7, 2002 now abandoned, all of which are incorporated herein by reference.

FIELD OF THE INVENTION

This invention relates to ion mobility spectrometry for gas and liquid sample preparation, filtering, and detection in a field asymmetric waveform ion mobility spectrometer, with electrospray sample delivery, and using either internal or external detectors.

BACKGROUND OF THE INVENTION

Electrospray mass spectrometry is a powerful analytical tool that has been broadly applied to bio-molecular structure analysis (i.e., Proteins, Peptides and DNA). See Electrospray Ionization Mass Spectrometry Fundamentals, Instruments, and Applications, Richard B. Cole, John Wiley and Sons, 1997. This technique plays a central role in the development of most pharmaceutical drugs and is being used to perform quantitative measurement of human exposure to carcinogens. Because of the size and potential revenues of the pharmaceutical market, there is interest in developing instrumentation based on, and technical enhancements to, electrospray mass spectrometry.

In recent years there has been a general trend to minimize the amount of sample required for analysis and micro-electrospray ionization (micro-ESI, micro-ES) and nano-spray describe two of these approaches. These two methods share a lot in common, and they are often used interchangeably. Micro-ES is a miniaturized electrospray source with the same system components as "conventional" electrospray. These include a source of pumped liquid flow containing the sample for analysis, a small diameter sharp hollow needle through which liquid is pumped, and a source of high voltage to generate the spray. Nanospray relies on the electrostatic attraction of the liquid inside the needle towards an attractor counter-electrode to generate the flow rather than a pump. This characteristic makes nanospray very attractive as a means to minimize sample waste. Since electrospray, micro-ES, and nanospray are all species of a generic class referred to as electrospray they will be interchangeably referred to as electrospray in this patent.

The nature of the electrospray ionization process makes sample preparation a major consideration. The presence of solvent and buffer salts along with the sample significantly increases spectral complexity and degrades detection limits. The electrospray ionization process produces an abundance of solvent ions that give an intense mass spectral background that can severely limit identification of many compounds at trace levels in solution. Even without the solvent ions to contend with, many applications require working with complex mixtures that necessitate some degree of separation prior to mass analysis. See J. Lee, J. F. Kelly, I. Chernushevich, D. J. Harrison, and P. Thibalut "Separation and Identification of Peptides from Gel-Isolated Membrane Proteins Using a Microfabricated Device for Combined Capillary Electrophoresis/Nanoelectrospray Mass Spectrometry," Anal.Chem.2000, 72,599–609. Better methods for elimination of unwanted solvent and separation of sample ions from background are therefore needed.

Electrospray mass spectrometry (ES-MS) provides a powerful tool for structure determination of peptides, proteins. This is important, as structure to a large extent defines the function of the protein. The structural information about a protein is typically determined from its amino acid sequence. To identify the sequence, the protein is usually digested by enzymes, and the peptide fragments are sequenced by tandem mass spectrometry. Another possible way to obtain the sequence is to digest the protein and measure the molecular weights of the peptide fragments. These are the input data for a computer program which digests theoretically all the proteins being found in the data base and the theoretical fragments are compared with the measured molecular weights.

Recently, it has been noticed that Ion Mobility Spectrometry can provide useful information to an electrospray/mass-spectrometry measurement. Ion Mobility spectrometry is ordinarily an atmospheric pressure technique which is highly sensitive to the shape and size of a molecule. Protein identification thorough the combination of an IMS and mass spectrometer may eliminate the need for protein digestion, simplifying sample preparation.

Commercially available IMS systems are based on time-of-flight (TOF), i.e., they measure the time it takes ions to travel from a shutter-gate to a detector through an inert atmosphere (1 to 760 Torr.). The drift time is dependent on the mobility of the ion (i.e., its size, mass and charge) and is characteristic of the ion species detected. TOF-IMS is a technique useful for the detection of many compounds including narcotics, explosives, and chemical warfare agents. See PCT Application Ser. No. PCT/CA99/00715 incorporated herein by this reference and U.S. Pat. No. 5,420,424 also incorporated herein by this reference. In ion mobility spectrometry, gas-phase ion mobility is determined using a drift tube with a constant low field strength electric field. Ions are gated into the drift tube and are subsequently separated based on differences in their drift velocity. The ion drift velocity under these conditions is proportional to the electric field strength and the ion mobility, which is determined from experimentation, is independent of the applied field. Current spectrometers use conventionally machined drift tubes (minimum size about 40 cm$^3$) for ion identification.

In conventional time-of-flight ion mobility spectrometers (TOF-IMS) ion identification is done in a low strength electric field (less than 1000 V/cm) where the coefficient of mobility for each ion is essentially independent of field strength [.W. McDaniel and Edward A. Mason, The mobility and diffusion of ions in gases, John Wiley & Sons, 1973].

At high electric fields, ion mobility becomes dependent upon the applied electric field strength and the ion drift velocity may no longer behave linearly with field strength. This principle is utilized in the subject of this disclosure.

The field asymmetric waveform ion mobility spectrometer (FAIMS, also known as RF-IMS) utilizes these significantly higher electric fields, and identifies the ion species based on the difference in its mobility in high and low strength electric fields.

The FAIMS spectrometer uses an ionization source, such as an ultra violet photo-ionization lamp, to convert a gas sample into a mixture of ion species with each ion type corresponding to a particular chemical in the gas sample. The ion species are then passed through an ion filter where particular electric fields are applied between electrodes to select an ion type allowed to pass through the filter. Once through the filter the ion type hits a detector electrode and produces an electrical signal. To detect a mixture of ion species in the sample, the electric fields applied between the filter electrodes can be scanned over a range and a spectrum generated. The ion filtering is achieved through the combination of two electric fields generated between the ion filter electrodes, an asymmetric, periodic, radio frequency (RF) electric field, and a dc compensation electric field. The asymmetric RF field has a significant difference between its peak positive field strength and negative field strength. The asymmetric RF field scatters the ions and causes them to deflect to the ion filter electrodes where they are neutralized, while the compensation field prevents the scattering of a particular ion allowing it to pass through to the detector. The ions are filtered in instruments on the basis of the difference in the mobility of the ion at high electric fields relative to its mobility at low electric fields. That is, the ions are separated due to the compound dependent behavior of their mobility at high electric fields relative to their mobility at low electric fields.

The FAIMS approach is based on an observation of Mason and McDaniel [.W. McDaniel and Edward A. Mason, The mobility and diffusion of ions in gases, John Wiley & Sons, 1973] who found that the mobility of an ion is affected by the applied electric field strength. Above an electric field to gas density ratio (E/N) of 40 Td (E>10,700 V/cm at atmospheric pressure) the mobility coefficient K(E) has a non-linear dependence on the field. This dependence is believed to be specific for each ion species. Below are some examples from Mason and McDaniel [.W. McDaniel and Edward A. Mason, The mobility and diffusion of ions in gases, John Wiley & Sons, 1973]. The mobility for the cluster ion $CO^+CO$ increases with increasing field strength (FIG. 7-1-K-1 in reference [.W. McDaniel and Edward A. Mason, The mobility and diffusion of ions in gases, John Wiley & Sons, 1973]). For some molecular and atomic ions the coefficient of mobility can change in a more complex way. For example, for atomic ions $K^+$, the mobility coefficient in carbon monoxide gas increases with increasing field by as much as 20%, but above E/N~200 Td the coefficient starts to decrease (FIG. 7-1-K-3 in reference [.W. McDaniel and Edward A. Mason, The mobility and diffusion of ions in gases, John Wiley & Sons, 1973]). For some other ions for example $N^+$, $N_3^+$ and $N_4^+$ the mobility changes very little (FIG. 7-1-H-1/2 in reference [.W. McDaniel and Edward A. Mason, The mobility and diffusion of ions in gases, John Wiley & Sons, 1973]). FIG. 1A illustrates schematically three possible ion mobility dependencies on electric field. For simplicity we will assume that the low field value of the mobility $K(E_{min})$ in a weak electric field (E approximately $10^2$–$10^3$ V/cm) is the same for all three ion types. However, at $E_{max}$ the value of the mobility coefficient $K(E_{max})$ is different for each ion type.

The field dependence of the mobility coefficient K(E) can be represented by a series expansion of even powers of E/N [18]

$$K(E)=K(0)[1+\alpha_1(E/N)^2+\alpha_2(E/N)^4+\ldots] \quad (1)$$

where K(0) is the coefficient of mobility of the ion in a weak electric field, and $\alpha_1$, $\alpha_2$ are coefficients of the expansion. This equation can be simplified by using an effective $\alpha(E)$ as shown in equation 2 [T. W. Carr, Plasma Chromatography, Plenum Press, New York and London, 1984], $$K(E) \approx K(0)[1+\alpha(E)]. \quad (2)$$

According to this expression when $\alpha(E)>0$ the mobility coefficient K(E) increases with field strength, when $\alpha(E)\sim0$ the mobility K(E) does not change, and when $\alpha(E)<0$ then K(E) decreases with increasing field strength. An expression for the field dependent mobility coefficient can also be derived from momentum and energy balance considerations. Where the energy of the ion $\epsilon=3/2\, kT_{eff}$ can be expressed as a function of its effective temperature [18–20].

$$K(E) = \frac{v}{E} = \frac{q}{N}\left(\frac{1}{3\mu kT_{eff}}\right)^{1/2}\frac{1}{\Omega(T_{eff})}. \quad (3)$$

The case where $\alpha(E)<0$ can be explained based on the model presented in equation 3, if one assumes the value of the ion neutral cross-section $\Omega(T_{eff})$ does not change significantly for rigid-sphere interactions [T. W. Carr, Plasma Chromatography, Plenum Press, New York and London, 1984, E. A. Mason and E. W. McDaniel, Transport Properties of Ions in Gases, Wiley, New York, 1988] and the reduced mass $\mu$ is constant. Under these conditions one finds that the mobility K(E) will decrease if the effective temperature, or energy, of the ion increases. Physically this effect has a simple explanation. When the electric field strength is increased the ions are driven harder through the neutral gas. This increases the ion neutral collision frequency, which leads to a reduced average ion velocity and a reduced ion mobility coefficient.

The rigid-sphere model however, does not explain the experimental results which show that with certain ions the mobility increases with increasing electric field ($\alpha(E)>0$). One of the possible explanations for the increased mobility at elevated values of E/N is offered when one allows for ion de-clustering at high field strengths to occur. Ions in ambient conditions in a weak electric field generally do not exist in a free state. They are usually in cluster form (for example, $MH^+(H_2O)_n$) with n polar molecules such as water attached. As the electric field strength is increased the kinetic energy and consequently the effective temperature ($T_{eff}$) of the ion increases due to the energy imparted between collisions. This can lead to a reduction in the level of ion clustering (reduction in n) resulting in a smaller ion cross-section $\Omega(T_{eff})$ and a smaller reduced mass $\mu$ for the ion. According to equation 3 then, if do to de-clustering the cross-section and reduced mass decrease in a sufficient manner to offset the increase in $T_{eff}$ the case where $\alpha(E)>0$ can be explained.

The third case when $\alpha(E)\sim0$ can be explained by a decrease in ion cross section due to de-clustering which is offset by an increase in the effective temperature of the ion. This results in no net change to the mobility coefficient of the ion.

The mechanism of operation of the FAIMS for ion filtering is described in the following. Consider three kinds of ions with different mobility coefficient dependencies on electric field (i.e., $\alpha(E)>0$, $\alpha(E)<0$, $\alpha(E)\sim0$) which are formed, due to local ionization of neutral molecules, at the same location in a narrow gap between two electrodes, as shown on FIG. 1B. A stream of carrier gas transports these ions longitudinally down the drift tube between the gap. If an asymmetric RF electric field is then applied to the electrodes the ions will oscillate in a perpendicular direction to the carrier gas flow, in response to the RF electric field, while moving down the drift tube with the carrier gas. A simplified asymmetric RF electric field waveform (FIG. 1C) with maximum field strength $|E_{max}|>10,000$ V/cm and minimum field strength $|E_{min}|<<|E_{max}|$ is used here to illustrate the operation principle of the RF-IMS. The asymmetric RF waveform is designed such that the time average electric field is zero and $$|E_{max}|t_1=|E_{min}|t_2=\beta. \tag{1}$$

$t_1$ is the portion of the period where the high field is applied and $t_2$ is the time the low field is applied. $\beta$ is a constant corresponding to the area under-the-curve in the high field and low field portions of the period. The ion velocities in the y-direction are given by $$V_y=K(E)E(t). \tag{2}$$

Here K is the coefficient of ion mobility for the ion species and E is the electric field intensity, in this case entirely in the y-direction. If the amplitude of the positive polarity RF voltage pulse (during $t_1$) produces an electric field of strength greater than 10,000 V/cm then the velocity towards the top electrode $$V_{up}=K_{up}|E_{max}| \tag{3}$$

will differ for each of the ion species (FIG. 1B) since, as shown in FIG. 1A, the coefficient of mobility $K_{up}$ for each ion at the high field condition is different. The ions with $\alpha(E)>0$ will move faster and ions with $\alpha(E)<0$ will have the smallest velocity, therefore, the slope of each ion's trajectory will also differ. In the next portion of the period ($t_2$), once the polarity of the RF field has switched, all three ion types will begin moving with the same velocity $$V_{down}=K(E_{min})|E_{min}| \tag{4}$$

down towards the bottom plate. In this low field strength condition (see FIG. 1A) all three ion types will have the same mobility coefficient $K_{down}$. Therefore, all three ion trajectories will have the same slope in this portion of the period (FIG. 1B).

The ion displacement from its initial position in the y-direction is the ion velocity in the y-direction $V_y$ multiplied by the length of time $\Delta t$ the field is applied $$\Delta y=V_y \Delta t. \tag{5}$$

In one period of the applied RF field the ion moves in both the positive and negative y-directions. By substituting equation 2 into equation 5 the average displacement of the ion over one period of the RF field can be written as $$\Delta y_{RF}=K_{up}|E_{max}|t_1-K_{down}|E_{min}|t_2. \tag{6}$$

Using equation 1 this expression can be re-written as $$\Delta y_{RF}=\beta(K_{up}-K_{down})=\beta \Delta K. \tag{7}$$

Since $\beta$ is a constant determined by the applied RF field, the y-displacement of the ion per period of the RF field $T=t_1+t_2$ depends on the change in mobility of the ion between its high and low field conditions. Assuming the carrier gas only transports the ion in the z-direction. The total ion displacement Y (in the y-direction) from its initial position (due to the electric field) during the ions residence time $t_{res}$ between the ion filter plates can be expressed as $$Y=\frac{\Delta y_{RF}}{(t_1+t_2)}t_{res}=\frac{\beta \Delta K}{T}t_{res} \tag{8}$$

The average ion residence time inside the ion filter region is given in equation 9. A is the cross-section area of the filter region, L is the length of the ion filter electrodes, V is the volume of the ion filter region V=AL, and Q is the volume flow rate of the carrier gas.

$$t_{res}=\frac{AL}{Q}=\frac{V}{Q}. \tag{9}$$

Substituting equation 9 into equation 8, noting from equation 1 that $\beta=|E_{max}|t_1$ and defining the duty cycle of the RF pulses as $D=t_1/T$. The equation for displacement of the ion species, equation 8, can be re-written as $$Y=\frac{\Delta K E_{max} VD}{Q} \tag{10}$$

where Y is now the total displacement of the ion in the y-direction based on the average ion residence time in the ion filter region. From equation 10 it is evident that the vertical displacement of the ions in the gap are proportional to the difference in coefficient of mobility between the low and high field strength conditions. Different species of ions with different $\Delta K$ values will displace to different values of Y for a given $t_{res}$. All the other parameters including the value of the maximum electric field, the volume of the ion filter region, the duty cycle and the flow rate, to first order are essentially the same for all ion species.

When a low strength DC field ($|E_c|<|E_{min}|<<|E_{max}|$) is applied in addition to the RF field, in a direction opposite to the average RF-induced (y-directed) motion of the ion, the trajectory of a particular ion species can be "straightened", see FIGS. 1D(1), 1D(2), 1D(3). This allows the ions of a particular species to pass unhindered between the ion filter electrodes while ions of all other species are deflected into the filter electrodes. The DC voltage that "tunes" the filter and produces a field which compensates for the RF-induced motion is characteristic of the ion species and is called the compensation voltage. A complete spectrum for the ions in the gas sample can be obtained by ramping or sweeping the DC compensation voltage applied to the filter. The ion current versus the value of the sweeping voltage forms the RF-IMS spectra. If instead of sweeping the voltage applied to one of the ion filter electrodes, a fixed DC voltage (compensation voltage) is applied, the spectrometer will work as continuous ion filter allowing only one type of ion through.

In PCT application Ser. No. PCT/CA99/00715, an electrospray ionization chamber or electrospray source is used to create ions which are ultimately transported to an analytical region which is subject to both a high frequency voltage asymmetric waveform and a DC offset voltage.

It is therefore an object of the present invention to provide method and apparatus for improved detection of compounds using field asymmetric waveform ion mobility.

SUMMARY OF THE INVENTION

Objects of the invention are achieved in practice of field asymmetric ion mobility spectrometers and novel improvements, particularly in three areas: 1) sample preparation and introduction, 2) ion filtering, and 3) output and signal collection.

Embodiments of the invention feature combinations of various aspects, including use of a FAIMS ion filter to filter ions where control of which ions are filtered is achieved by control of a variable DC compensation signal in addition to a high field asymmetric waveform radio frequency signal or use of a FAIMS filter where the control of which ions are filtered is achieved by varying the wavelength, frequency, amplitude, period, duty cycle or the like of the high field asymmetric waveform radio frequency signal; use of a planar FAIMS filter which uses insulating substrates to very accurately control the gap between the ion filter electrodes and ensure the ion filter electrodes are parallel, this allows very reproducible fields to be obtained which results in a higher resolution spectrometer; use of a planar FAIMS filter where the insulating spacers overlap the edges of the filter electrodes, which results in a higher resolution FAIMS with more accurate identification of compounds since all the sample is forced to pass between the ion filters and no ions can bypass the filter electrodes and still reach the detector electrode.

In use with a spray source, such as electrospray, where desolvation of the ions is very important in order to obtain reliable, reproducible spectra, desolvation is achieved. Desolvation electrodes may be included to assist in desolvation, where enhanced desolvation is achieved by applying symmetric RF signals to the desolvation electrodes. The RF signals provide energy to the ions which raises their effective temperature and helps to enhance the desolvation process.

Desolvation electrodes can also be used to control the level of ion clustering in gas samples from electrospray and from other than electrospray sources. Control of ion clustering can permit more repeatable measurements and also can provide additional information on the ions being detected.

A novel embodiment of the invention relates to the sample preparation section. This embodiment incorporates the use of an electrospray head and the use of an attraction electrode which is separated from the ion filter electrodes. The advantage of separating the attraction electrode from the ion filter electrodes is that this allows freedom in applying a different potential to the attraction electrode relative to the ion filter electrodes, and this allows optimization of the electrospray conditions and ion introduction conditions into the FAIMS. This separation of attraction electrode from the ion filter electrodes can also be realized in cylindrical FAIMS configurations.

Additionally, guiding electrodes can be provided and allow further optimization of ion injection into the ion filter. In a further embodiment of the invention the electrospray assembly can be attached to one of the substrates of the FAIMS and guiding electrodes are used to guide the ions into the ionization region. The guiding electrodes can be a freestanding structure attached or connected to or near one of the substrates of the FAIMS. The assembly can have a counter gas flow to enhance desolvation.

The invention also features the realization of the concept that a time-of-flight measurement can be combined with a FAIMS approach using electrospray to provide improved identification of the ion species through the additional information provided by the time-of-flight measurement. The time it takes the ion to travel from the orifice of the FAIMS to the detector can be measured. This can be achieved through the independent control of the attraction and guiding electrode potentials. For example, initially the attraction electrode potential is adjusted so that no ions make it into the drift region, but rather are collected at the guiding electrodes. Then the attraction electrode is pulsed so that some ions can make it into the ionization region and into the ion filter. Now the time it takes the ions to travel from the ionization region to the detector can be measured, and this provides additional discriminating information on the identity of the ion.

A novel aspect of the invention is the concept of formation of electrodes on an insulating or insulated substrate where the insulating substrate can form a housing. This approach provides significant advantages in simplification of device construction. It allows low cost, mass producible processes to be used such as micromachining and multichip modules which can result in low cost, miniature sensors.

In the output section, the embodiments of the FAIMS proposed are the first to have output sections with the ability to detect multiple ion species simultaneously such as a positively and negatively charged ion.

Since sample analysis in the FAIMS is generally performed in the gas phase, liquid samples require conversion from the liquid to the gas phase. In a preferred embodiment, the electrospray method (which we define as encompassing "conventional", micro and/or nanospray) is used to convert a liquid sample into gas phase ions. Preferably the ions streaming out of the electrospray tip are submitted to a planar FAIMS device. In a preferred practice of the invention, all the functions of sample preparation, ionization, filtering and detection are performed on a single "chip".

In another embodiment, the electrospray-FAIMS is applied as a filter to a mass spectrometer. The FAIMS coupled to the mass spectrometer provides enhanced resolution, better detection limits, ability to extract shape and structure information of the molecules being analyzed, molecules can include bio-molecules such as proteins and peptides. The FAIMS technique is based on ion mobility, where ion filtering and identification is highly dependent on the size and shape of the ion. This information is of great interest in genomics and proteomics research (i.e., pharmaceutical industry) since the shape of a protein to a large extent determines its functionality and therefore FAIMS filtering can be applied as a low cost high volume method of protein characterization. A particular embodiment includes a disposable FAIMS filter chip which is plugged into a carrier mounted on the inlet of a mass spectrometer. The FAIMS-electrospray device can also provide structural (conformation) information about the molecule being analyzed and sequence information not obtainable simply with electrospray-mass spectrometry. In addition the FAIMS allows discrimination between isomers (molecules with the identical mass but which differ in their shape) which cannot be identified using electrospray-mass spectrometry alone.

In a particular embodiment, the electrospray-FAIMS forms a filter and detection system in a single housing. The electrospray-FAIMS configuration of the present invention can be used as a standalone detector for liquid sample analysis or as the front end to a mass spectrometer. The present invention also has application to other liquid separation techniques such as liquid chromatography, high pressure liquid chromatography, and capillary electrophoresis. A preferred embodiment of the invention includes a planar FAIMS apparatus where in one embodiment the device is integrated with an electrospray ionizing source on a common housing or substrate and is coupled to a mass spectrometer. Alternative practices of the invention may include cylindrical or coaxial FAIMS devices.

Embodiments of the invention enable filtering of molecules after they have been ejected from a source, such as from an electrospray tip or a capillary electrophoresis outlet, and have been ionized prior to filtering via a FAIMS filter, and detected via an internal detector or via a mass spectrometer or other detector. In one practice of the invention, micromachining (MEMS) processing enables integration of an electrospray tip with a FAIMS filter into a simple device and results in a precise yet compact analytical system for accurate, highly repeatable, liquid sample evaluation. In another practice of the invention, portable, miniature, low cost, bio-sensors for biological agent detection which use an integrated electrospray-FAIMS chip are possible; preferably they are prepared using micromachining fabrication techniques. In one embodiment an atmospheric pressure chemical ionization (APCI) device is achieved with a FAIMS filter used as a prefilter to a mass spectrometer.

Prior to the present invention, conventional machining led to high cost of fabrication and poor reproducibility from FAIMS device to FAIMS device. Furthermore, prior art cylindrical FAIMS geometry either limits collection efficiency when interfacing to a mass spectrometer, or permits both sample neutrals and sample ions to enter the mass spectrometer, resulting in more complex spectra. Advantageously in practice of the invention, ion filtering is performed after sample ionization, therefore buffer salt and solvent ions, which are invariably generated in the electrospray process, are separated from the bio-molecules of interest. This provides significantly simpler mass spectra and improves the detection limits and identification of the bio-molecules.

Combination of electrospray with a new FAIMS filter device enables analytical detection devices with greatly enhanced sensitivity and resolution. In some cases the ability is provided to resolve compounds that could not be identified without the FAIMS present. Combination of electrospray with a prior art FAIMS filter devices raises issues of sample to sample contamination when running low concentration samples through the device for high throughput low cost sample analysis, but these are overcome in practice of the present invention.

The new FAIMS of the invention is a low cost, a volume manufacturable, small and compact, spectrometer based on differential ion mobility. The present invention, particularly configured using high volume manufacturing techniques, such as MEMS fabrication techniques which includes ceramic packaging, PC board manufacturing techniques or plastic processing, offers several additional advantages over prior devices. The volume manufacture techniques result in low cost devices that can be made disposable, thus avoiding the problem of sample cross contamination. These chips will be available to any laboratory using a mass spectrometer for biological molecule identification as a FAIMS interface filter. Such a filter includes the FAIMS interface chip which can plug into an interface fixture which contains, filtering electronics. The electrospray tip or electrophoresis chips can be integrated with (fabricated as part of) the FAIMS chip. The MEMS approach is not required but is preferred and renders high reliability and repeatability in volume manufactured FAIMS chips; this lowers their cost and enables disposable devices. This disposability avoids contamination from one sample to the next, which is invaluable for tests performed subject to, for and/or by regulatory agencies like the EPA and FDA where contamination is a concern.

In one embodiment of the present invention, a planar MEMS FAIMS chip was fabricated in which ions are focused into a mass spectrometer and collection efficiency is close to 100%. In this embodiment, no ion injection is required into the FAIMS ion filter region. The device is micromachined on a planar surface. This enables easy integration with onboard heaters to minimize ion clustering. It can be easily integrated with micromachined or conventional electrospray tips and/or micromachined electrophoresis chips. This is a simplified design with reduced fabrication requirements, and can be configured to use only a single gas flow channel.

Micromachining provides for excellent reproducibility in the manufacture and performance of the filters. This is critical so that test results are consistent from one device to the next and from one laboratory to the next. Micromachining enables new configurations of FAIMS filter chips which cannot be made any other way. These new configurations are simpler and more efficient at delivering ions to the mass spectrometer and filtering unwanted ions.

A MEMS FAIMS drift tube has been successfully fabricated and characterized. High spectrometer sensitivity and ability to resolve chemicals not separated in conventional TOF-IMS has been demonstrated. The MEMS FAIMS enables the realization of miniature, low cost, high sensitivity, high reliability chemical detectors. The FAIMS spectrometer of the invention has also been demonstrated as a pre-filter to a mass spectrometer. The new FAIMS/MS combination allows better resolution of complex mixtures.

Portable, miniature, low cost, bio-sensors for biological agent detection which use an integrated electrospray-FAIMS chip are possible using microfabrication methods such as micromachining s because of the size reduction and cost reductions enabled by this technology and enabled manufacture. These instruments will have many uses, including availing high quality bio-analysis in the field. For example, a person suspected of being exposed to a bio-agent will supply a drop of blood to the instrument. The blood will be mixed with a buffer solution, processed, and introduced via the electrospray nozzle into the FAIMS where the ions will be analyzed. If a particular bio-molecule is detected an alarm will be set off. As well, micromachining enables new configurations of FAIMS filter chips which are not otherwise available. For example, the planar FAIMS disclosed in this patent. These new configurations are simpler and more efficient at delivering ions to the mass spectrometer and filtering unwanted ions. In a preferred embodiment, the Electrospray and FAIMS form an atmospheric pressure chemical ionization (APCI) prefilter and analyte filter and detection system in a single housing. The new FAIMS-APCI provides high performance and low cost, volume manufacturable, small and compact, ion mobility spectrometer.

In an embodiment of the invention, a breakthrough can be attributed to providing a multi-use housing/substrate/packaging that simplifies formation of the component parts and resulting assembly. Additional features include the possibility to use the substrate as a physical platform to build the filter upon and to give structure to the whole device, to use the substrate as an insulated platform or enclosure that defines the flow path through the device, and/or use the substrate to provide an isolating structure that improves performance. A spacer can be incorporated into the device, which provides both a defining structure and also the possibility of a pair of silicon electrodes for further biasing control. Multiple electrode formations and a functional spacer arrangement can be utilized which improve performance and capability. Filtering employs the FAIMS asymmetric periodic voltage applied to the filters along with a control component, and this component can be a bias signal or voltage or may be supplied simply otherwise, such as by control of the duty cycle of the same asymmetric signal and which removes the need for the DC compensation circuit. This compact arrangement enables inclusion of a heater for purging ions, and may even include use of the existing electrodes, such as filter or detector electrodes, for heating/temperature control.

Embodiments of the invention include a field asymmetric ion mobility spectrometer apparatus and some preferred embodiments include a sample preparation and introduction section, ion filtering section, and an output section and a control section, the filter comprising a FAIMS ion filter for filtering ions. Embodiments of the invention may variously include: planar FAIMS filter which uses insulating substrates to very accurately control the gap between the ion filter electrodes and ensure the ion filter electrodes are parallel, this allows very reproducible fields to be obtained which results in a higher resolution spectrometer; a FAIMS filter where the insulating spacers overlap the edges of the filter electrodes. This results in a higher resolution FAIMS with more accurate identification of compounds since all the sample is forced to pass between the ion filters and no ions can bypass the filter electrodes and still reach the detector electrode; an electrospray head and providing desolvation of the ions via desolvation electrodes; enhanced desolvation is achieved by applying symmetric RF signals to the desolvation electrodes; the RF signals provide energy to the ions which raises their effective temperature and helps to enhance the desolvation process; wherein desolvation electrodes for control of the level of ion clustering in gas samples, for more repeatable measurements and providing additional information on the ions being detected, are provided in a practice of the invention.

A novel aspect may include the concept of formation of electrodes on an insulating or insulated substrate where the insulating substrate can form a housing, and providing significant advantages in simplification of device construction, with low cost, mass producible processes to be used such as micromachining and manufacture of multichip modules which can result in low cost, miniature sensors using FAIMS architecture; within the output section the ability to detect multiple ion species simultaneously such as a positively and negatively charged ion; further incorporating the use of an electrospray head and the use of an attraction electrode which is separated from the ion filter electrodes to permit applying a different potential to the attraction electrode relative to the ion filter electrode(s), and this allows optimization of the electrospray conditions and ion introduction conditions into the FAIMS device. The FAIMS device may be cylindrical-type, planar-type, or otherwise. Guiding electrodes can allow further optimization of ion injection into the ion filter.

It is also possible to form a time-of-flight measurement device combined with the FAIMS device using electrospray to provide improved identification of the ion species through the additional information provided by the time-of-flight measurement; the time it takes the ion to travel from the orifice of the FAIMS to the detector can be measured, which can be achieved through the independent control of the attraction and guiding electrode potentials; wherein the electrospray assembly can be attached to one of the substrates of the FAIMS and guiding electrodes are used to guide the ions into the ionization region; a counter gas flow enhances desolvation; wherein the guiding electrodes can be a freestanding structure attached or connected to or near one of the substrates of the FAIMS; wherein control of which ions are filtered is achieved by control of a variable DC compensation signal in addition to a high field asymmetric waveform radio frequency signal, or control of which ions are filtered is achieved by varying an aspect of the field such as the duty cycle, amplitude or frequency of the high field asymmetric waveform radio frequency signal, among others.

All the functions of sample preparation, ionization, filtering and detection can be performed on a single chip or workpiece of the invention; wherein an electrospray-FAIMS is applied as a filter to a mass spectrometer; a chip carrier and a disposable FAIMS filter chip which is plugged into the carrier, the carrier enable for mounting on the inlet of a mass spectrometer; wherein an electrospray-FAIMS forms a filter and detection system in a single housing; wherein electrospray-FAIMS configuration of the present invention can be used as a standalone detector for liquid sample analysis or as the front end to a mass spectrometer; wherein present invention also has application to other liquid separation techniques such as liquid chromatography, high pressure liquid chromatography, and capillary electrophoresis; wherein a preferred embodiment of the invention includes a FAIMS apparatus where in one embodiment the FAIMS device is integrated with an electrospray ionizing source on a common housing or substrate and is coupled to a mass spectrometer; wherein embodiments of the invention enable filtering of molecules after they have been ejected from a source, such as from an electrospray tip or a capillary electrophoresis outlet, and have been ionized prior to filtering via a FAIMS filter, and detected via an internal detector, or via a mass spectrometer or other detector, and in a practice of the invention, micromachining (MEMS) processing enables integration of an electrospray tip with a planar field asymmetric waveform ion mobility spectrometer filter into a simple unit/device and results in a precise yet compact analytical system for accurate, highly repeatable, liquid sample evaluation, or in another practice of the invention, portable, miniature, low cost, bio-sensors for biological agent detection which use an integrated electrospray-FAIMS chip are possible, possibly prepared using micromachining fabrication techniques; wherein the FAIMS part is planar and forms an atmospheric pressure chemical ionization (APCI) prefilter to a mass spectrometer; wherein ion filtering is performed after sample ionization, therefore buffer salt and solvent ions, which are invariably generated in the electrospray process, are separated from the bio-molecules of interest and this provides significantly simpler mass spectra and improves the detection limits and identification of the bio-molecules; wherein combination of electrospray with a FAIMS filter device enables analytical detection devices with greatly enhanced sensitivity and resolution and wherein in some cases the ability is provided to resolve compounds that could not be identified without the FAIMS present, and wherein combination of electrospray with a prior art FAIMS filter devices raises issues of sample to sample contamination when running low concentration samples through the device, high throughput low cost sample analysis, but these are overcome in practice of the present invention.

A mass spectrometer is directly coupled to the exhaust port at the end of the drift tube, wherein a baffle may be placed to regulate the velocity of waste gas flow stream relative to the velocity of drift gas flow stream, in a practice of the invention. Various sample preparation sections can be used, whether simply a port to draw in ambient air samples, or electrospray, gas chromatograph, liquid chromatograph, or the like. A split gas flow may be used to prevent clustering and allows better identification of ion species.

The relationship between the amount of monomer and cluster ions for a given ion species is dependent on the concentration of sample and the particular experimental conditions (e.g., moisture, temperature, flow rate, intensity of RF-electric field). In a practice of the invention, both monomer and cluster states are detected to provide useful information for chemical identification. In one example, a planar two channel FAIMS is used to achieve this result, wherein a curtain gas is applied to sample neutrals and they are prevented from entering the second channel "II" and ions in the monomer state can be investigated. In another embodiment, curtain gasses may flow in the same direction and exhaust at an orifice or in opposite directions while guiding electrodes are included to guide the ions into the second channel "II" and an attraction electrode is also used to attract ions into channel "II", such that when the curtain gas is turned off ions in the cluster state may be observed since sample neutrals and sample ions may now be drawn into channel "II" using a pump. The output section may be connected to a mass spectrometer.

A method of the invention includes coupling a FAIMS device to a mass spectrometer, for providing enhanced resolution, better detection limits, ability to extract shape and structure information of the molecules being analyzed, molecules can include bio-molecules such as proteins and peptides, the FAIMS technique being based on ion mobility, where ion filtering and identification is highly dependent on the size and shape of the ion, the FAIMS-electrospray device providing structural (conformation) information about the molecule being analyzed and sequence information not obtainable simply with electrospray-mass spectrometry and also allowing discrimination between isomers (molecules with the identical mass but which differ in their shape) which cannot be identified using electrospray-mass spectrometry alone.

Embodiments of the invention feature a multi-functional use of the FAIMS substrates. The substrates are platforms (or a physical support structures) for the precise definition and location of the component parts or sections of the device. The substrates form a housing, enclosing the flow path with the filter and perhaps the detector, as well as other components. This multi-functional design reduces parts count while also precisely locating the component parts so that quality and consistency in volume manufacture can be achieved. The smaller device also has unexpected performance improvements, perhaps because of the smaller drift tube and perhaps also because substrates also perform an electronic isolation function. By being insulating or an insulator (e.g., glass, ceramic, plastic), the substrates can be a direct platform for formation of components, such as electrodes, with improved performance characteristics.

Embodiment of the invention may be cylindrical or planar, or the like. In disclosed embodiments, use of substrates as a support/housing does not preclude yet other "housing" parts or other structures to be built around the device. For example, it might be desirable to put a humidity barrier over the device. As well, additional components, like batteries, can be mounted to the outside of the substrate/housing, e.g., in a battery enclosure. Nevertheless, embodiments of the presently claimed invention can provide a substrate insulation function, support function, multi-functional housing function, as well as other functions.

The insulative or insulated substrate/flow path invention achieves excellent performance in a simplified structure. The use of an electrically insulated flow path in a FAIMS device enables the applied asymmetric periodic voltage to be isolated from the output part (e.g., from the electrodes of the detector), where detection takes place. This reduction is accomplished because the insulated substrates provide insulated territory between the filter and detector in the flow path, and this spacing in turn advantageously separates the filter's field from the detector. The less noisy detection environment means a more sensitive FAIMS device.

Moreover, by forming the electrodes on an insulative substrate, the ion filter electrodes and detector electrodes can be positioned closer together which unexpectedly enhances ion collection efficiency and favorably reduces the device's mass that needs to be regulated, heated and controlled. This also reduces power requirements. Furthermore, use of small electrodes reduces capacitance which in turn reduces power consumption. As well, tightly spaced electrodes lends itself to a mass production process, since the insulating surfaces of the substrates are a perfect platform for the forming of such electrodes.

Embodiments of the claimed invention result in FAIMS devices that achieve high resolution, fast operation and high sensitivity, yet with a low parts count and in configurations that can be cost-effectively manufactured and assembled in high volume. Quite remarkably, packaging is very compact for such a capable FAIMS device, with sensitivity in the range of parts per billion or trillion. In addition, the reduced real estate of this smaller device leads to reduced power requirements, whether in sensing ions or in heating the device surfaces, and can enable use of a smaller battery. The benefits of the simplified and compact FAIMS spectrometer according to the invention requires typically as little as one second (and even less) to produce a complete spectrum for a given sample. No FAIMS system has ever been taught or disclosed in the prior art that can achieve such beneficial results.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1D1 shows compensation voltage applied to cancel out displacement produced by RF-field.

FIG. 1D2 shows the trajectory of ion from initial position with only the RF field applied and the trajectory of ion with only the compensation field applied.

FIG. 1D3 shows the trajectory of ion with both RF and compensation fields applied.

FIG. 2 is a schematic of a chemical sensor system in practice of the invention.

FIG. 3B shows a chemical sensor system with liquid sample preparation section including an electrospray in practice of the invention.

FIG. 3B1 shows a machined electrospray head in practice of the invention.

FIG. 4B shows an alternative structural electrode embodiment in practice of the invention.

FIG. 9A shows an electrospray head cooperating with guiding electrodes in practice of the invention.

DETAILED DESCRIPTION OF THE PREFERRED EMBODIMENTS

A description of preferred embodiments of the invention follows.

The present invention provides method and apparatus for analysis of compounds in a liquid sample, preferably enabled by high field asymmetric waveform ion mobility spectrometry.

Figure 2:
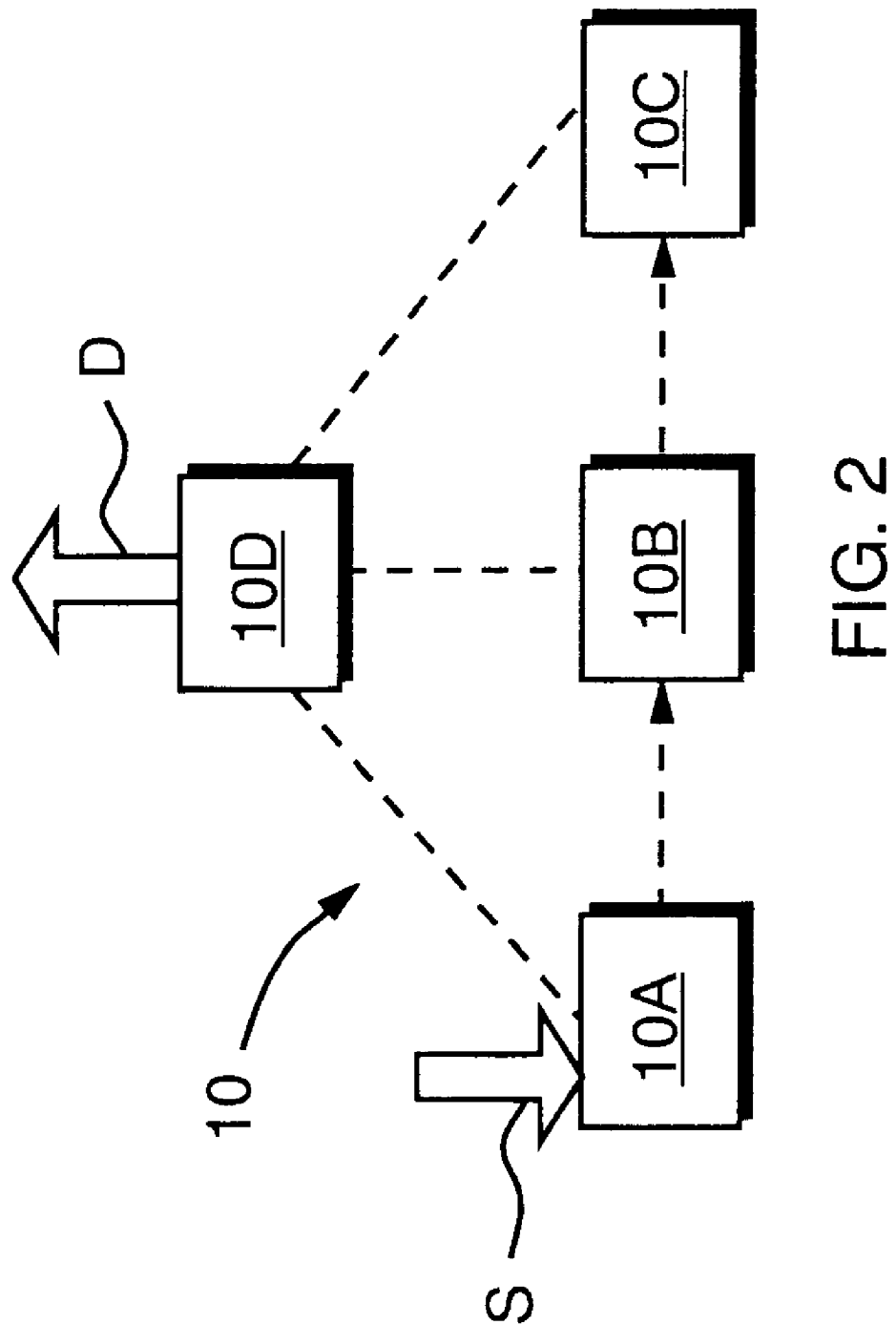

In an illustrative embodiment of the present invention shown in FIG. 2, a chemical sensor system 10 includes a sample preparation section 10A, a filter section 10B, and an output section 10C. In practice, a liquid sample S is ionized in sample preparation section 10A, the created ions then being passed to and filtered in filter section 10B, and then ions passing through the filter section are delivered to output section 10C for detection. The liquid sample preparation section 10A, filter section 10B, and output section 10C operate under control and direction of controller section 10D. Preferably controller section 10D controls both the operation of system 10 and appraises and reports detection data D.

In a preferred embodiment of the invention, the liquid sample preparation section 10A includes an electrospray head, which receives, conditions, and ionizes liquid sample S. This is transported to a preferred planar high field asymmetric ion mobility spectrometer (PFAIMS) filter in section 10B, the latter filtering the delivered ions and passing ion species of interest to output section 10C. In various embodiments of the invention, function in output section 10C may include immediate detection of ion species or transfer of ions to another component such as a mass spectrometer (MS) for detection of ion species thereat, with a readout being available of data D indicative of detected ion species.

As will be understood by a person skilled in the art, the FAIMS filter with planar surfaces is preferred in embodiments of the present invention, but embodiments of the present invention are operable with various non-planar parts and surfaces, including filters, detectors, flow paths, electrodes, and the like. The description herein of PFAIMS is by way of illustration and not limitation.

Figure 3A:
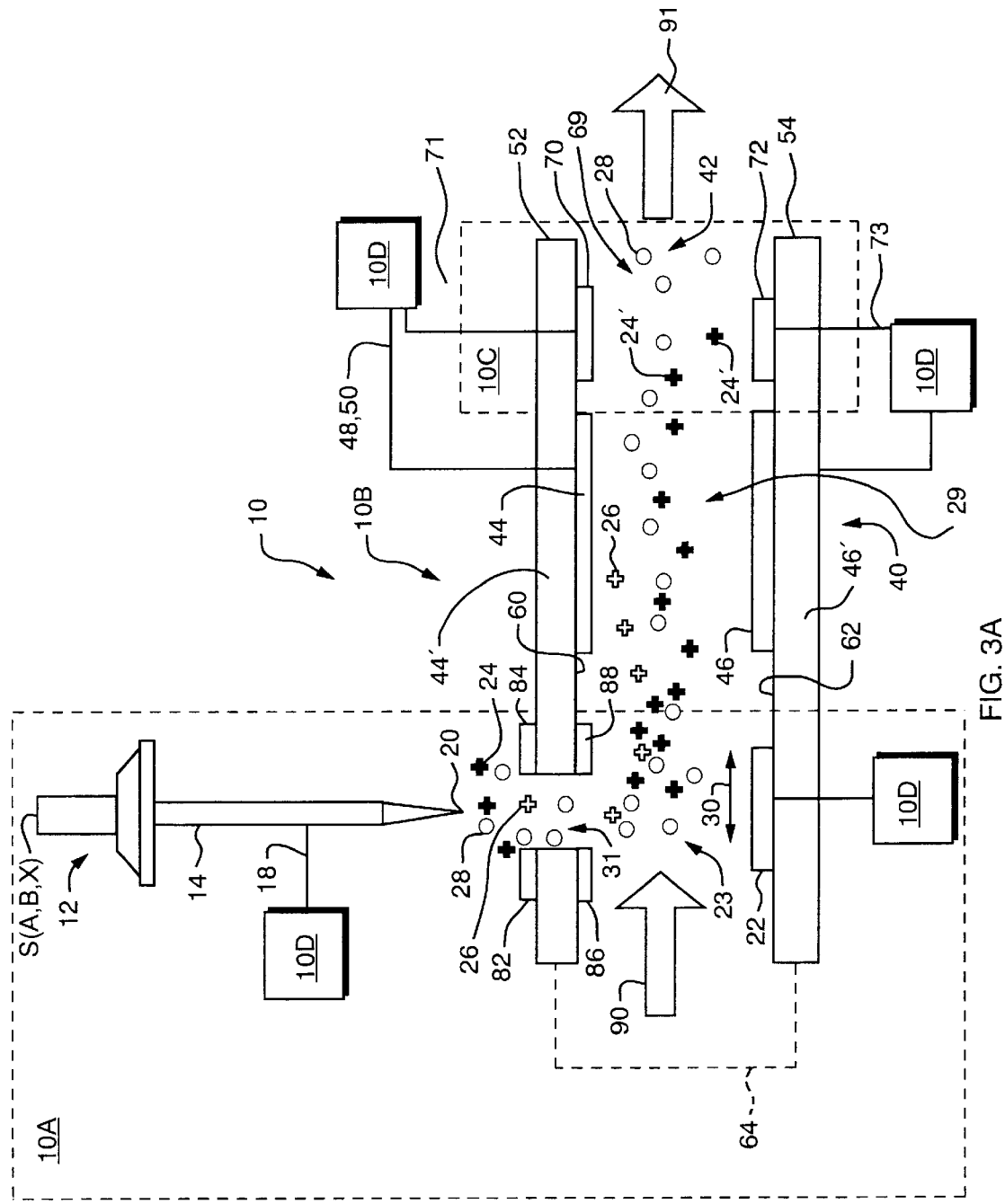
FIG. 3A shows a chemical sensor system with liquid sample preparation section including an electrospray in practice of the invention.
Figure 3C:
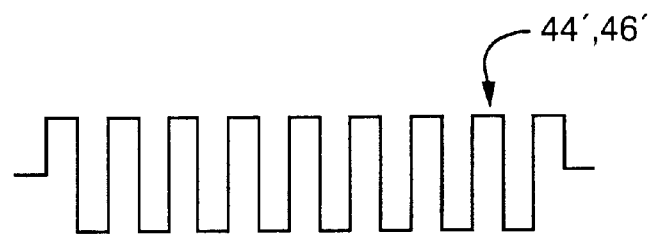
FIG. 3C shows a serpentine electrode in practice of the invention.

In the embodiments of FIGS. 3A, 3B, liquid sample preparation section 10A includes electrospray sample ionization source or head 12 having a chamber 14 for receipt of liquid sample S. In practice of the invention, the liquid sample S may contain bio-compounds, for example compounds A and B, in a solvent X. The present invention is engaged to identify one or more of the compounds in the liquid sample.

In practice of the electrospray device of section 10A, a high voltage potential 18 is applied by controller 10D to the liquid sample S within chamber 14 of electrospray head 12. The potential difference between the liquid sample S at electrospray tip 20 and attraction electrode 22, driven by controller 10D, ionizes compounds A, B in solvent X in sample S in ion region 23. This creates ions 24 and 26, representing compounds A and B, and solvent molecules 28. In a preferred embodiment, ions and solvent are driven or drawn along flow path 30 into filter section 10B between the parallel filter electrodes 44, 46 of PFAIMS ion filter 40.

Filtering in the PFAIMS filter device 40 is based on differences in ion mobility, which is influenced by ion size and shape, among other items. This enables separation of ion species based on their characteristics. In one practice of the invention, a high intensity asymmetric waveform radio frequency (RF) signal 48 and a DC compensation signal 50 are applied to filter electrodes 44, 46 by RF/DC generator circuits within controller 10D. The asymmetric field alternates between a high and low field strength condition that causes the ions to move in response to the field according to their mobility. Typically the mobility in the high field differs from that of the low field. This mobility difference produces a net transverse displacement of the ions as they travel longitudinally through the filter between the filter electrodes.

In the absence of a compensating bias signal, these ions would hit one of the filter electrodes and be neutralized. In the presence of a selected compensating bias signal 50 (or other compensation), a particular ion species will be returned toward the center of the flow path and will pass through the filter. Therefore, in the presence of the compensated asymmetric RF signal 48, separation of ions from each other according to their species can be achieved. Unselected species will hit the electrodes and be neutralized and species of interest will be passed through the filter. The data and system controller 10D regulate the signals 48, 50 applied to the filter electrodes 44, 46, in order to select which ion species pass through the filter.

It will be appreciated that it is desirable to isolate ions 24 and 26 to be able to obtain unambiguous identification of either or both of compounds A and B, as can be achieve with the PFAIMS filter 40. The PFAIMS filter 40 discriminates between ions A and B based on their mobility, such that in principle only one or the other is presented for detection at output section 10C according to the compensation applied by controller 10D. For example, ions 24 are shown as ions 24' passed by filter 40 in FIGS. 3A, 3B.

Referring again to FIGS. 3A, 3B, the output section 10C includes detector 69 with detector electrodes 70, 72. Controller 10D measures the current on electrodes 70, 72 as an indication of ions passed by filter 40. These electrodes are held at a potential by bias signals 71, 73, from controller 10D. Ions 24' which passed filter 40 deposit their charge on a detector electrode 70, 72 under control of controller 10D, depending upon the polarity of the electrode and the control signals 71, 73 on the detector electrodes. Furthermore, by sweeping the compensation (i.e., the bias voltage), a complete spectrum of ion species in Sample S can be detected.

By intelligent control of controller 10D it is possible to select different operating regimes and as a result it is possible to target the filtering of ion species of interest. In practice of one embodiment of the invention, the asymmetric electric signal 48 is applied in conjunction with compensating bias voltage 50, and the result is that the filter passes desired ion species as controlled by electronic controller 10D. As well, by sweeping bias voltage 50 over a predetermined voltage range, a complete spectrum of ion species in sample S can be achieved.

In another embodiment, the asymmetric electric signal enables passing of the desired ion species where the compensation is in the form of varying the duty cycle of the asymmetric electric signal, without the need for compensating bias voltage, again under direction of the control signals supplied by the electronic controller. By means of these features, the apparatus is also tunable, i.e., it can be tuned to filter ion species, passing only desired selected species to the detector.

A further advantage of the invention is that the filter can pass multiple ion species with similar mobility but different polarity, and these can be detected simultaneously. If each detector electrode 70, 72 is held at a different polarity, then multiple ion species (having similar mobility but different polarity) that pass through the filter can be detected simultaneously. Detected ions are correlated with the applied control signals 48, 50 and potential bias signals 71, 73 to determine the species of detected ion(s) indicated at data D, FIG. 2.

This multi-functionality may be further understood by reference to output section 10C, such as in FIG. 3A, where a top electrode 70 is held at a predetermined voltage at the same polarity as the ions of interest passed by filter 40 while bottom electrode 72 is held at another level, perhaps at ground. Top electrode 70 deflects ions 24' downward to electrode 72 for detection. However, either electrode may detect ions depending on the ion charge and polarity and the signal applied to the electrodes. Thus multiple ion species having similar mobility but different polarity that pass through the filter can be detected simultaneously by using top electrode 70 as one detector and bottom electrode 72 as a second detector, and using two different detector circuits in controller 10D, with two different outputs thus emitted. Detector 69 may thus detect simultaneously multiple species passed by the PFAIMS filter 40, such as a gas sample including sulfur in a hydrocarbon gas background.

The electronics controller 10D supplies the controlling electronic signals to system 10. A control circuit could be on-board, or off-board, where the PFAIMS device has a control part with at least the leads and contact pads shown in FIG. 4A that connect to the control circuit 10D. The signals from the controller are applied to the filter electrodes via such connections.

Figure 4A:
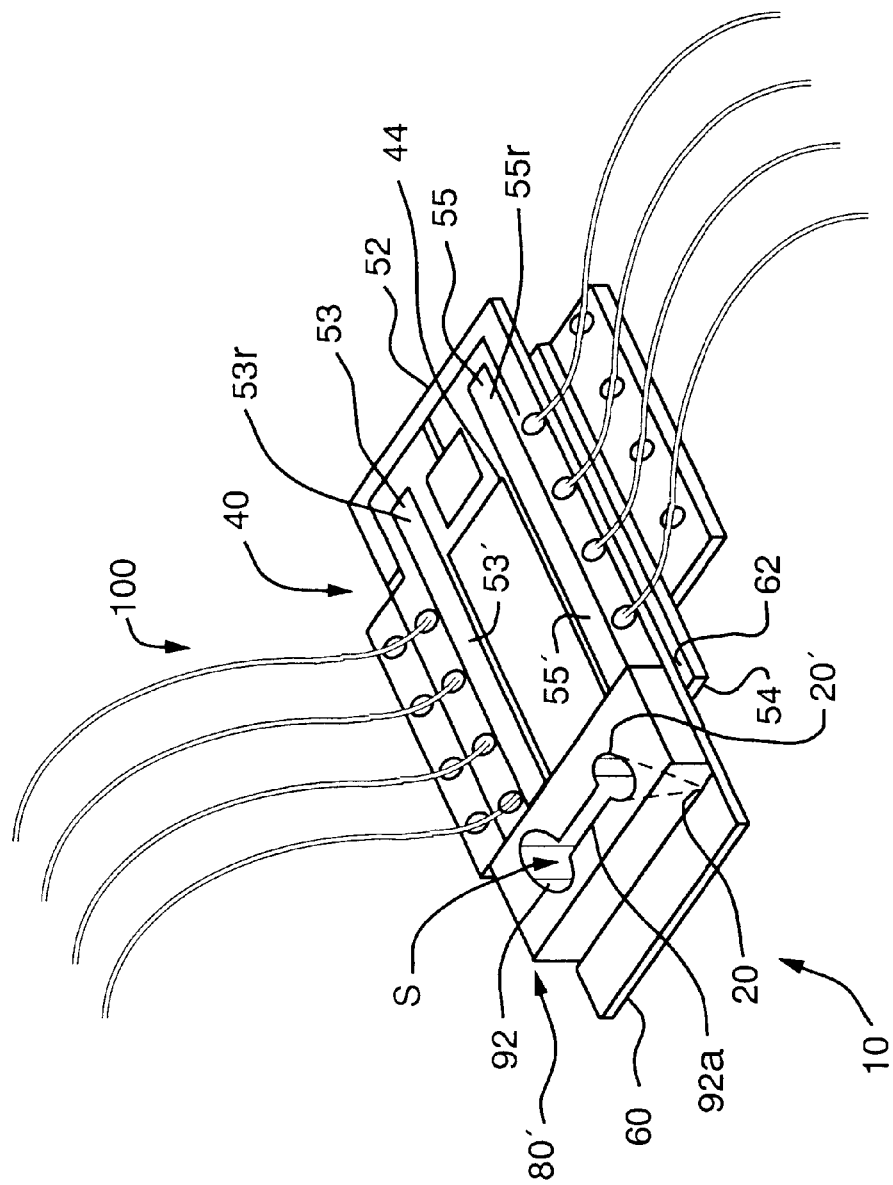
FIG. 4A shows a FAIMS spectrometer with spaced insulated substrates in practice of the invention.

In the embodiment of FIG. 4A, a PFAIMS system 10 includes a spectrometer chip 100 having spaced insulated substrates 52, 54, (e.g., Pyrex® glass, ceramic, plastic and the like) with filter electrodes 44, 46 formed thereon (of gold or the like). Substrates 52, 54, define between themselves the drift tube 29 and flow path 30, thus performing a housing function. Preferably the substrates are insulating or have surfaces 60, 62 for insulated mounting of electrodes. Electrodes 44, 46 form ion filter 40, with the filter electrodes mounted on these insulated surfaces 60, 62 facing each other across the flow path 30.

Figure 4C:
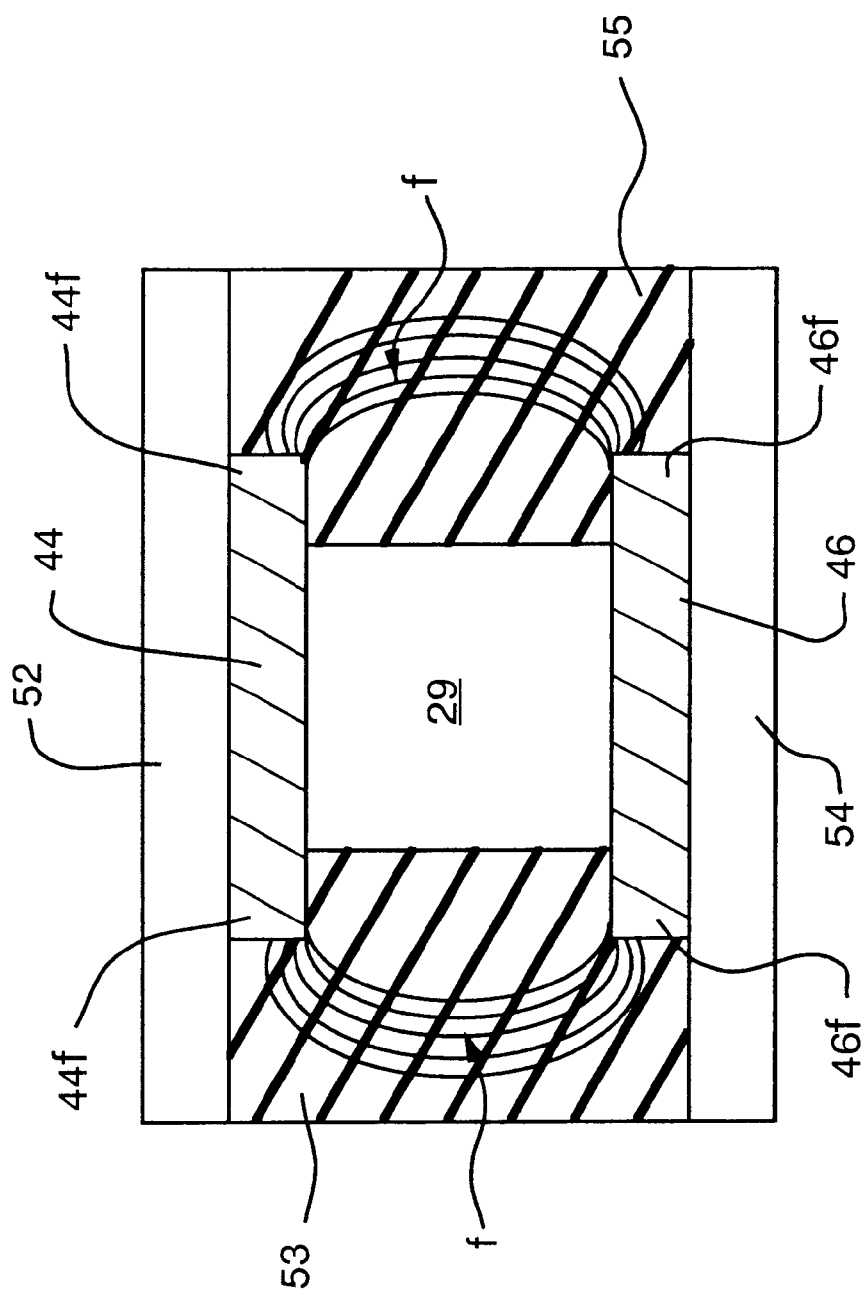
FIG. 4C shows side cross-sectional view of filter with insulating spacers overlapping edges of electrodes in practice of the invention.

As shown in FIGS. 4A, 4B, 4C, substrates 52, 54 are separated by spacers 53, 55, which may be insulating and formed from ceramic, plastic, Teflon® or the like, or may be formed by etching or dicing silicon wafers, or creating an extension of the substrates 52, 54, for example. The thickness of the spacers defines the distance "D" between the faces of substrates 52, 54 carrying electrodes 44, 46. In one embodiment of FIG. 4A, the silicon spacers can be used as electrodes 53', 55' and a confining voltage is applied by controller 10D to the silicon spacer electrodes to confine the filtered ions within the center of the flow path. This confinement can result in more ions striking the detectors, and which in turn improves detection.

In a further alternative embodiment of the invention shown in FIG. 4B, alternative structural electrodes 44x, 46x, take the place of the substrates 52, 54, and are mounted at and separated by insulating spacers 53, 55, forming flow path 30 within. At one end of the flow path, sample preparation section 10A supplies the ions to the filter section 10B, and at the other end, the filtered ions pass into an output section 10C. In the same manner that the substrates serve a structure function and form a housing, so too the structural electrodes 44x, 46x serve the function of a housing, as well as being electrodes. As with the substrates, the outer surface of these electrodes may be planar or not, and may be covered by an insulated surface 61.

In the embodiment of FIG. 4C, shown in side cross-section, the insulating spacers 53, 55 overlap with the edges 44f, 46f of filter electrodes 44, 46. This ensures that the ions flowing in flow path (i.e., drift tube) 29 are confined to a region of uniform transverse electric field between the filter electrodes 44, 46, away from the electrode edges 44f, 46f where the non-uniform fringing field "f" is present. A further benefit is that all ions are forced to pass between the filter electrodes, and are subjected to that uniform field.

Figure 3D:
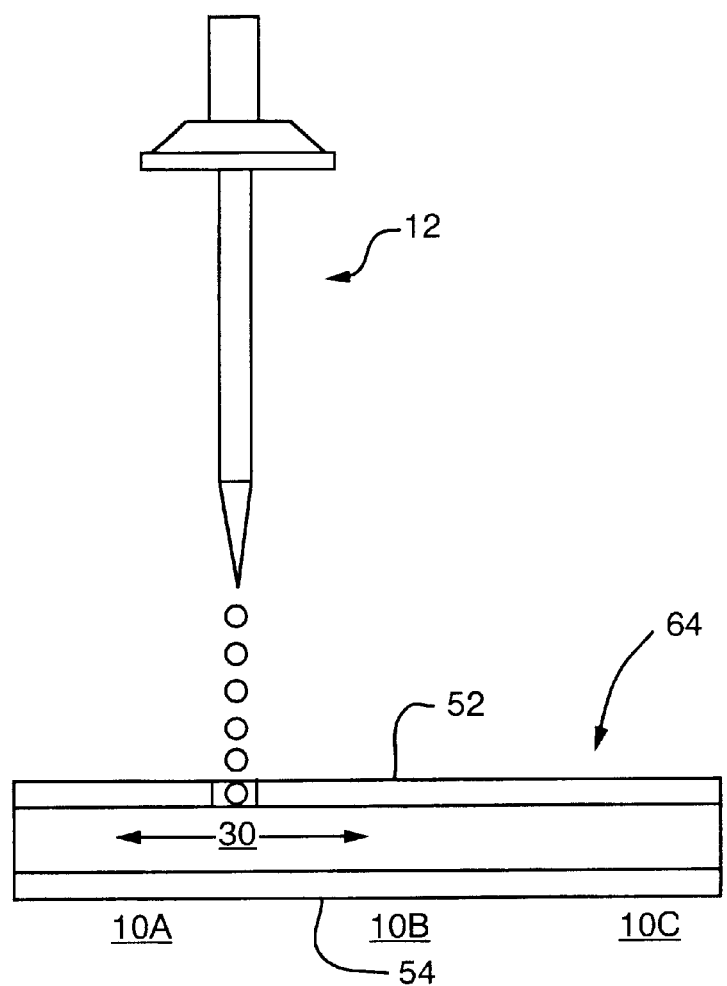
FIG. 3D shows the substrates forming a housing in practice of the invention.

Returning to FIG. 3A, in operation, ions 24, 26 flow into the filter 40. Some ions are neutralized as they collide with filter electrodes 44, 46. These neutralized ions are generally purged by the carrier gas. Purging can also be achieved, for example, by heating the flow path 30, such as by applying a current to appropriately configured filter electrodes (e.g., serpentine 44',46' shown in FIG. 3D) or to resistive spacer electrodes. Spacer electrodes 53, 55 of FIG. 4A could be formed with resistive material and therefore could be used as heatable electrodes 53r, 55r.

Ions 24 are passed to output section 10C of FIG. 3A. Exhaust port 42 is provided to exhaust the molecules 28 from the passed ions 24. This isolation of ions 24 eases the detection function and enables more accurate chemical analysis. But even with this precaution, some solvent molecules may remain attached to the ions of interest 24. Therefore, in a preferred embodiment, apparatus is provided to desolvate ions such as 24 and 26 prior to their filtering. Desolvation may be achieved by heating. For example, any of electrodes 44, 46, 53r, 55r, may have a heater signal applied thereto by controller 10D. In another embodiment incoming gas flow may be heated by heater element 89 as shown in FIG. 3B.

It will be appreciated by those skilled in the art that desolvation or "drying" of electrosprayed ions is a critical part of the electrospray process. When the ion is first ejected out the electrospray tip it is in the form of a droplet with a large amount of solvent coating the ion. As it travels through the air towards a counter electrode the solvent evaporates eventually leaving the desolvated ion which can then be analyzed. Incomplete desolvation prior to analysis can distort the analysis. Additionally, a long ion travel distance may be required to allow the ion to sufficiently desolvate, without some other assistance. It will therefore be appreciated that this desolvation is beneficial in practice of the invention.

Figure 5A:
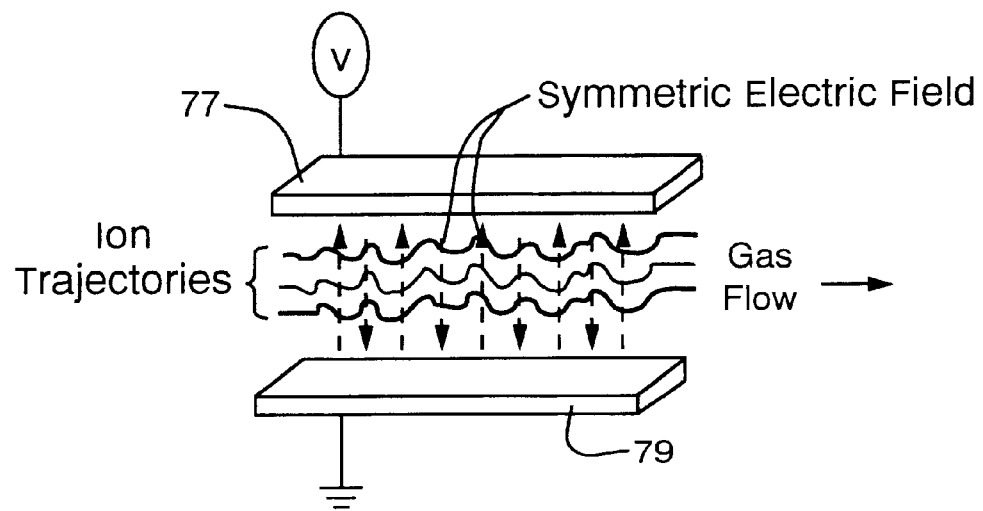
FIG. 5A shows symmetric AC radio frequency field for ion desolvation in practice of the invention.
Figure 5B:
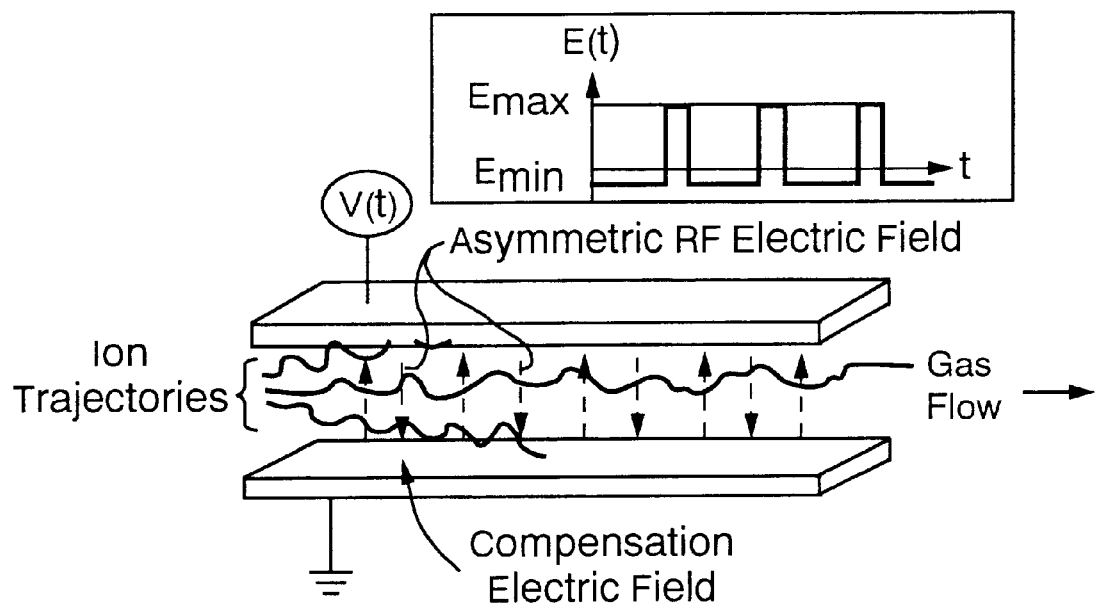
FIG. 5B shows the desolvation region integrated into a FAIMS device in practice of the invention.

In another embodiment of the invention, a symmetric RF-electric field is used to enhance desolvation of ions produced in the electrospray prior to analysis. As shown in FIGS. 5A, 5B, a symmetric radio frequency field applied perpendicularly to the carrier gas flow to cause the ions generated in the electrospray process to oscillate symmetrically, and be heated, as they travel down the drift tube so that the ions are desolvated without net deflection from this signal.

More particularly, the interaction between the ions and the neutral molecules raises their effective temperature, enhancing their desolvation. During their oscillations the ions will impact neutral air molecules and their internal temperature will increase. The rise in the internal temperature of the ions enhances the evaporation of the solvent and shortens the time to realize a desolvated charged ion. This action enables desolvation to be done over a relatively short length of the drift tube. Desolvation results in more accurate detection data, and the above approach is easily integrated with the PFAIMS filter of the invention.

The desolvating electric field can be generated by applying a voltage between two electrodes configured parallel to each other with a gap between them. For example, any of electrode pairs 44, 46 and 53, 55 may be used for this function, under control of controller 10D. Preferably separate desolvation electrodes 77, 79, as shown in FIG. 3B may be used for this function.

Figure 1A:
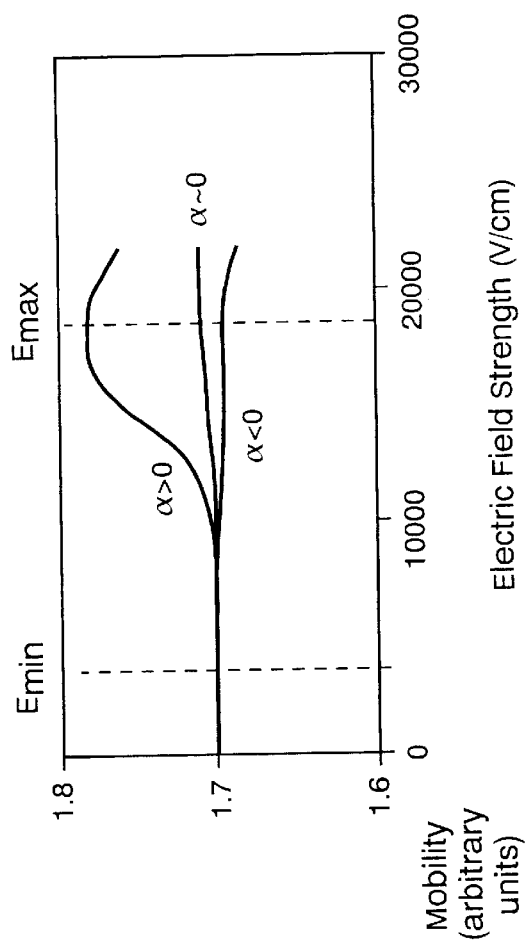
FIG. 1A shows the mobility dependence on electric field for three different ion species.
Figure 1B:
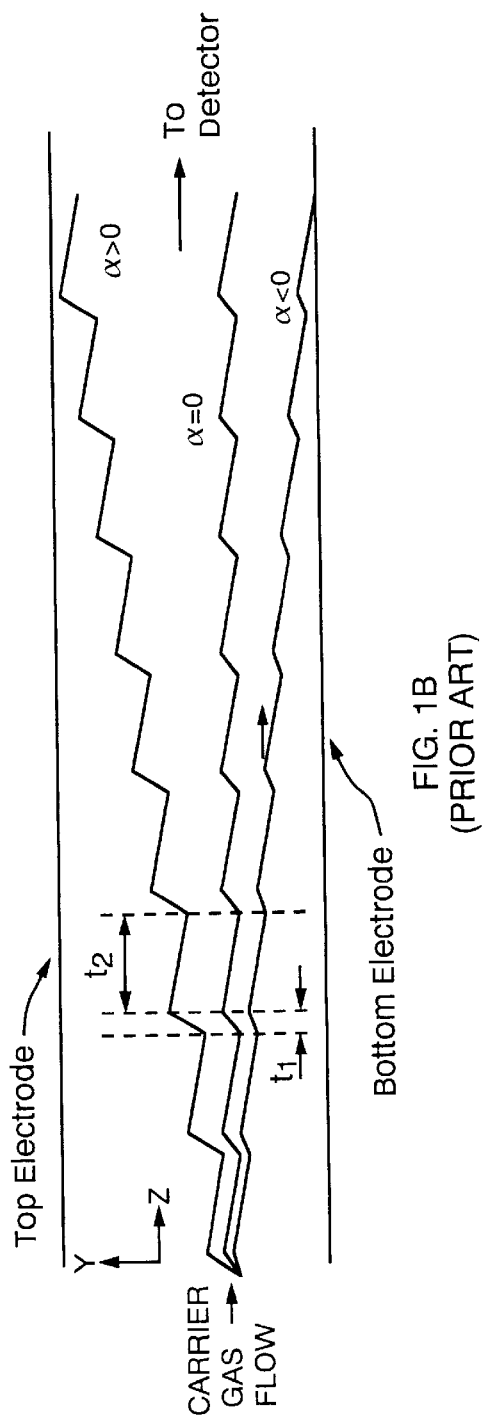
FIG. 1B shows the trajectories of ions in the gap between the upper and lower parallel plate electrodes of the ion filter, under the simultaneous influence of the carrier gas flow and an asymmetric radio frequency electric field waveform.
Figure 1C:
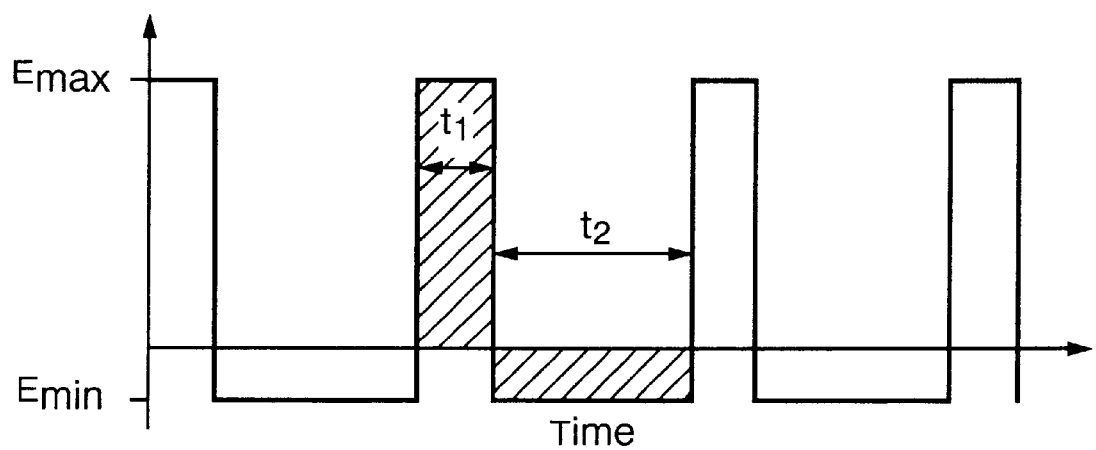
FIG. 1C shows a simplified asymmetric RF electric field waveform used for ion filtering.

In a further embodiment of the invention, a micromachined electrospray head 80 is mounted on substrate 52, shown schematically in FIGS. 3B and 3B1. Electrodes 82, 84, 86, 88 are formed on opposite sides of substrate 52 and guide the electrospray ions 24, 26 into ion region 23 of flow path 30 in drift tube 29. Attraction electrode 22 has a potential applied thereto to attract the ions 24, 26 into the ion region 23. Carrier gas flow 90 is set at a desired flow rate to capture ions 24, 26 and to carry them to filter 40 for the filtering function already described. The gas exhaust 91 includes the carrier gas 90 and carries away non-ionized components and neutralized ions.

Potentials applied to electrodes 22, 82, 84, 86, 88, and even desolvation electrodes 77, 79, can be set and controlled independent of each other and of the filter electrodes 44, 46. For example, this advantageously enables the attractor electrode 22 to be driven with a different signal than any other electrode, such as the adjacent filter electrode 46. This is particularly facilitated by provision of the insulated surfaces of the substrates, and the electrode isolation allows optimization of ion introduction independent of filter drive requirements.

This configuration also enables the guiding electrodes 82,84, 86, 88 and attractor electrode 22 to be individually operated in a pulsed mode (e.g., switched on and off). In this mode, a select amount of ions can be introduced into the ion region 23. The time these ions travel, such as from the orifice to detector 72 for example, can be used in a "time-of-flight" ("TOF") FAIMS mode of operation. In this mode, the time of flight is associated with ion species, thus providing additional information for species discrimination. This leads to an improvement in cylindrical FAIMS devices.

As will be appreciated by a person skilled in the art of IMS, this TOF is an analog to the time-of-flight practiced in IMS devices, but now being practiced within a FAIMS structure. This new innovation may therefore provide both IMS and FAIMS detection data in one operating device; the combination of FAIMS and IMS data can yield better detection results.

In preferred embodiments, such as shown in FIGS. 3A–3B, 4A–4B, the housing 64 is formed by substrates 52, 54, with internal flow path 30 defined extending from the input part 10A, through the ion filter 10B, to the output part 10C. More particularly, substrates 52, 54 present work surfaces 60, 62, which favor formation of electrodes thereat. These surfaces 60, 62 may be curved or planar and preferably insulating (or insulated), such as when formed using glass or ceramic substrates for example. This lends itself to mass manufacturing techniques such as Micro-Electro-Mechanical Systems (MEMS) or Multi-Chip Module (MCM) or other processes, with a result of very compact packaging and small electrode sizes. As such, the ion filter is preferably defined on these insulated surfaces by the facing filter electrodes 44, 46 with the flow path 30 defined in between, and the insulated surfaces of the substrates in turn then isolating the control signals 48, 50 at the filter electrodes from detector electrodes 70, 72, for lower noise and improved performance. This is unlike the extensive conductive area of the outer cylinder of conventional prior art FAIMS devices, such as in U.S. Pat. No. 5,420,424, incorporated herein by reference.

Figure 6:
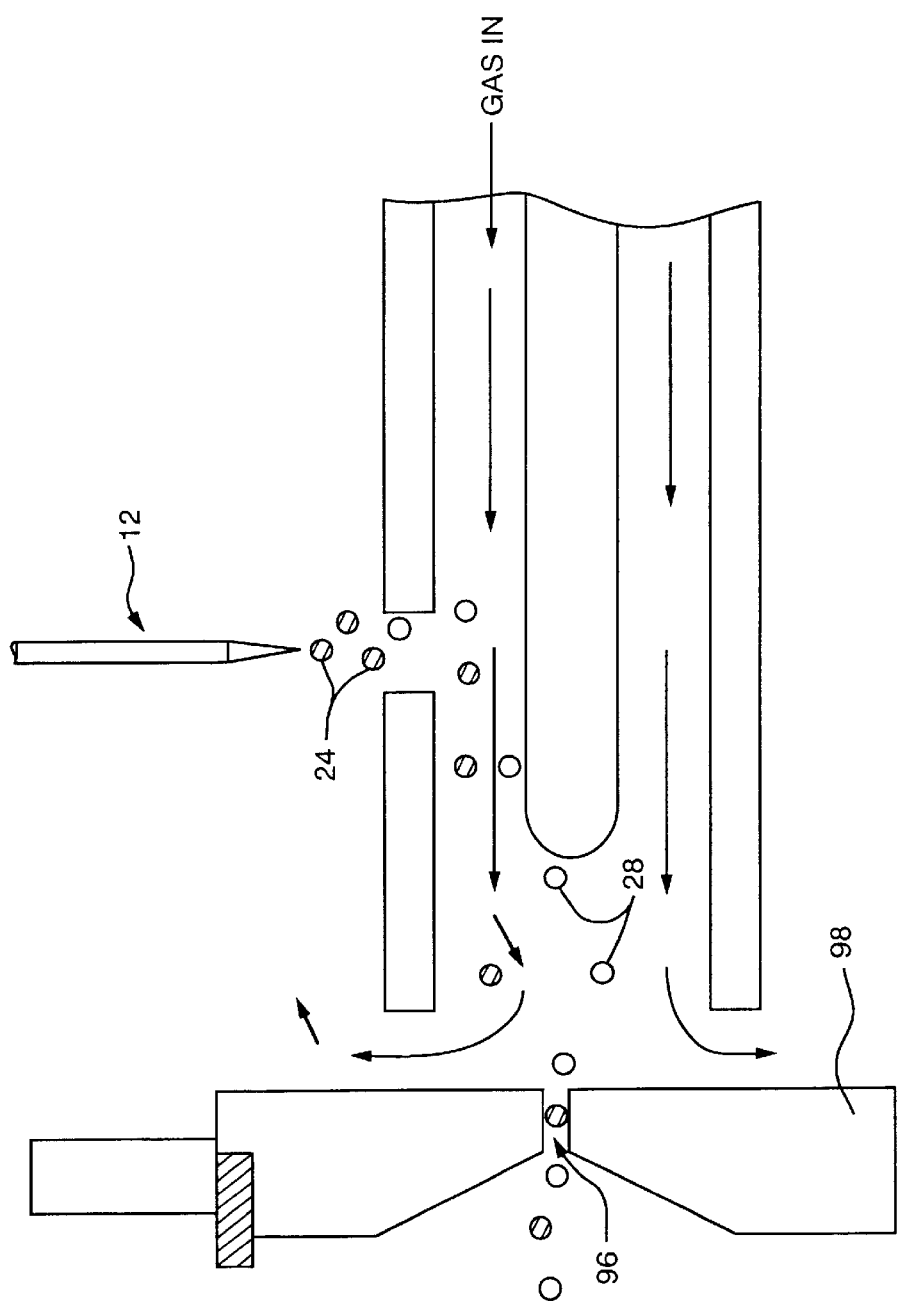
FIG. 6 shows a prior art cylindrical FAIMS connected to a mass spectrometer.

It will be further understood that due to geometrical and physical considerations, the ions in prior art cylindrical designs are distributed in the drift tube cross-section and therefore only a fraction of ions are available in the region R near the mass spec inlet 96. In the prior art configuration of a cylindrical FAIMS shown in FIG. 6 (see PCT/CA99/00715, incorporated herein by reference), an attempt is made to overcome this limitation by enabling additional delivery of ions to the mass spectrometer inlet 96. However neutral sample molecules can also enter into the mass spectrometer inlet 96 because there is no separation between the sample ions 24 and neutral molecules, such as solvent molecules 28. This leads to significantly more complex spectra in the mass spectrometer, and degraded resolution.

The present invention overcomes these shortcomings in the configuration of FIG. 3B, for example. In practice of the invention, virtually all of the ions 24 entering the detector region 69 are focused into the mass spec inlet 96. This results in a dramatic increase in efficiency of detection and improved sensitivity of the system, especially compared to a cylindrical FAIMS device where ions are distributed around the entire flow path circumference, not just at the MS inlet.

Figure 7A:
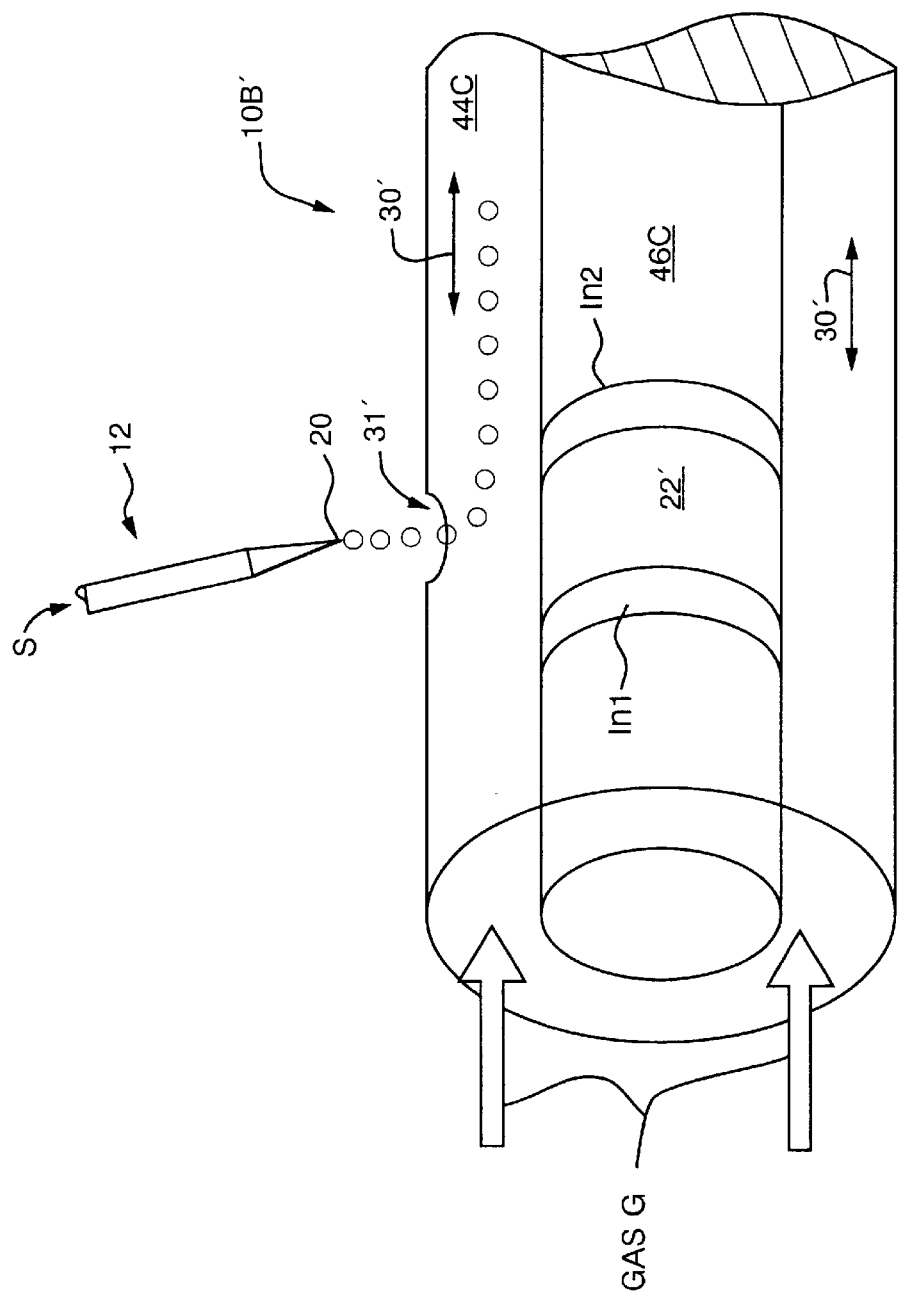
FIGS. 7A, 7B show improved cylindrical FAIMS devices in practice of the invention.

Furthermore, referring to a new cylindrical design of the present invention, shown in FIG. 7A, electrospray tip 20 injects samples via orifice 31' in outer electrode 44C into flow channel 30', under attraction of attractor electrode 22', and the sample is carried by the flow of gas G toward the filter section 10B'. The attractor electrode is formed adjacent to the inner electrode 46C but electrically isolated by insulator strips In1, In2. Therefore the attractor electrode can be independently biased separate from neighboring electrodes, e.g., 46C. This embodiment also combines functional and structural components while reducing parts count, such as where the inner cylinder components can be mated together via a binding function of the insulating layers In1, In2, for example.

Figure 7B:
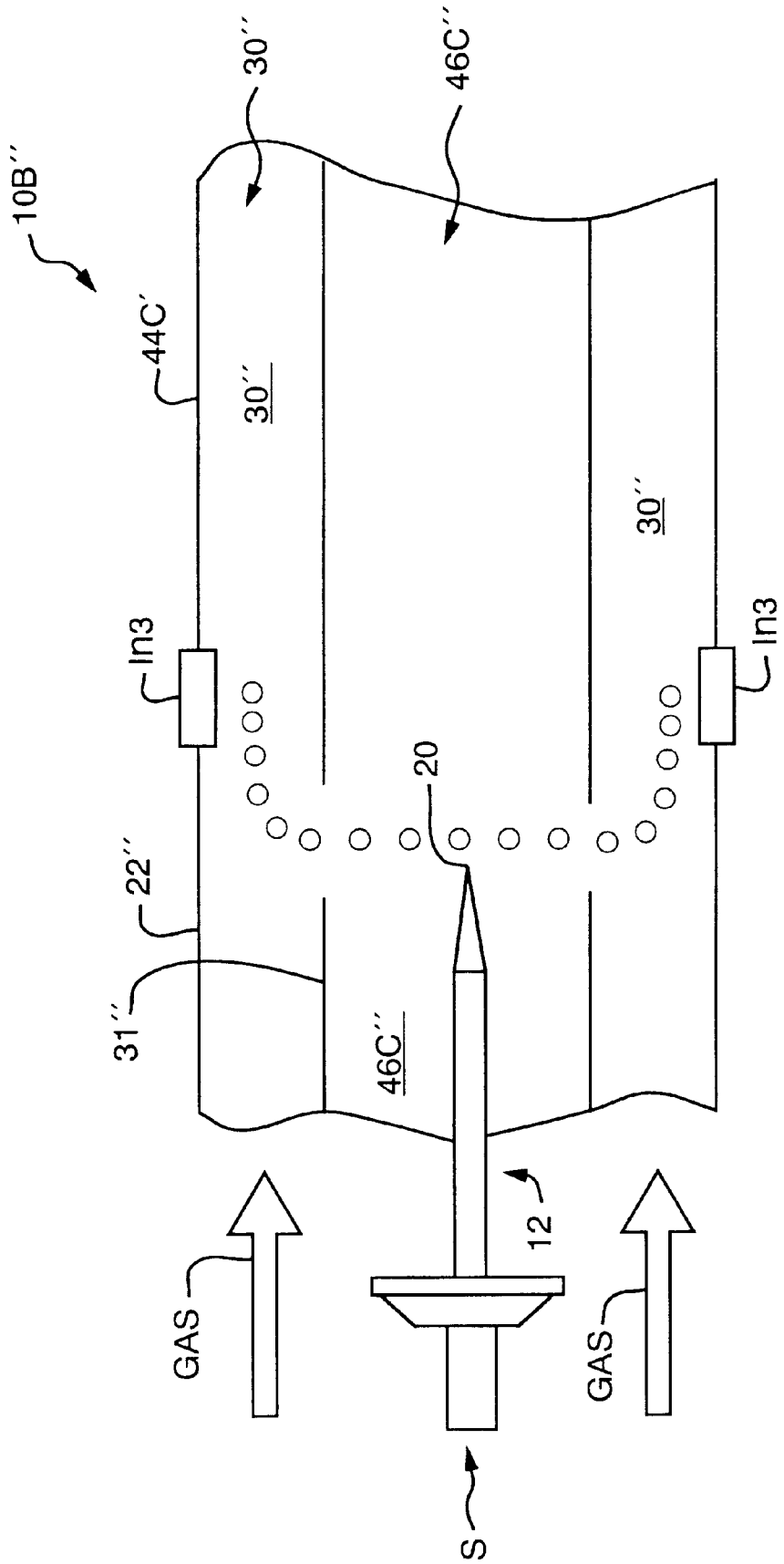

In an alternative embodiment shown in FIG. 7B, an attractor electrode 22" is formed adjacent to outer ring electrode 44C', insulated therefrom by insulator ring In3. The electrospray tip 20 introduces sample S from the side into the interior of a ring 46C", which may be a separate electrode, or may be an extension of inner electrode 46C', with the sample under attraction of attractor electrode 22" and being carried by gas G in flow channel 30" of filter section 10B". Again, electrode 22" is isolated from electrode 44C' by insulator In3, and therefore the electrodes are independently drivable.

Figure 8:
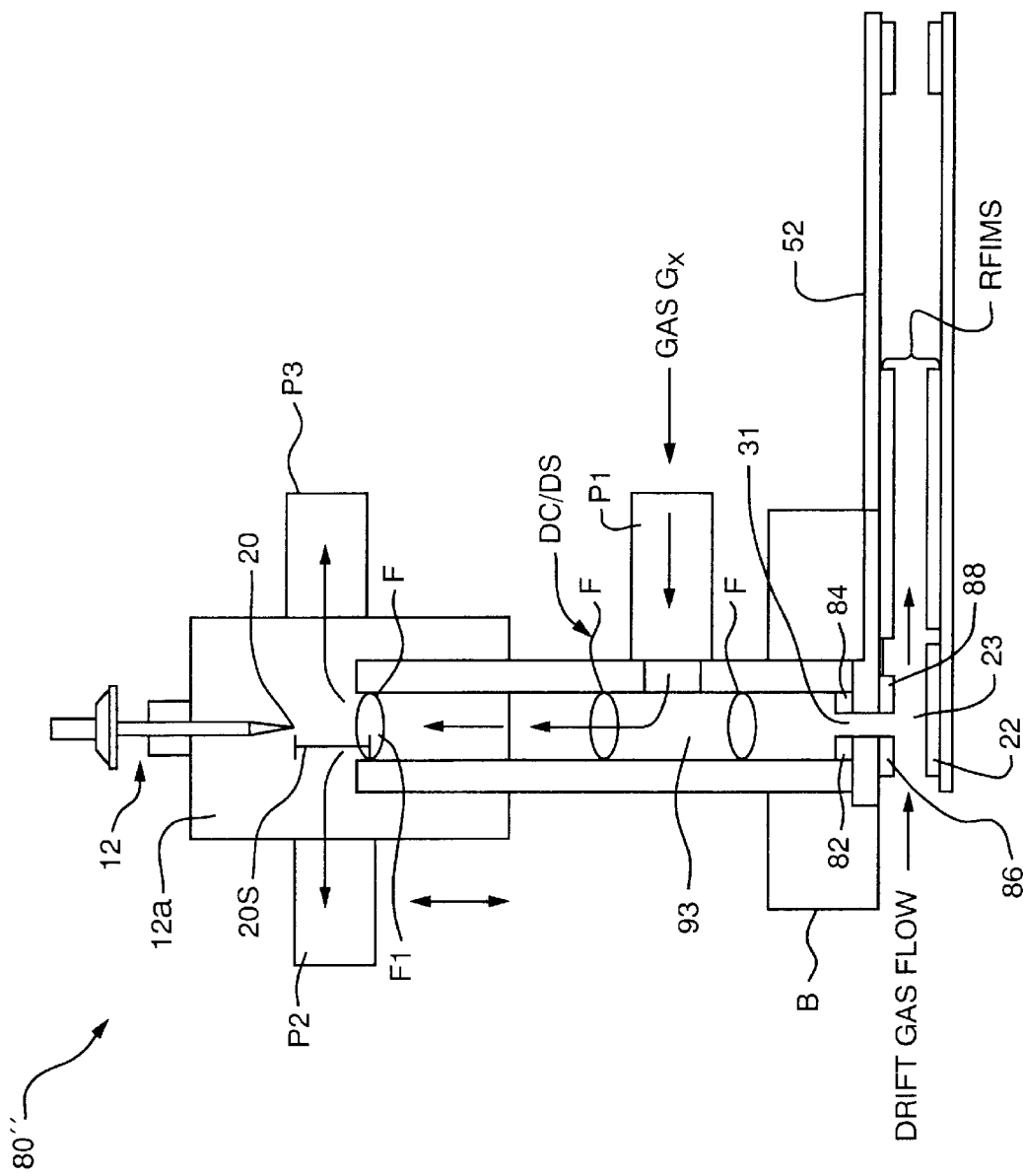
FIG. 8 shows an electrospray mounting tower in practice of the invention.

In a further embodiment of the invention shown in FIG. 8, electrospray assembly 80", attached to substrate 52, includes electrospray head 12. The ions are carried by guiding electrodes "F" (three in this embodiment), toward orifice 31 and are attracted into ion region 23 by attraction electrode 22 and guiding electrodes, such as 82, 84 and/or 86, 88.

Preferably a separate DC bias "DC" is applied to each guiding electrode to create a potential gradient which guides the ions towards ion region 23. The guiding electrodes can be used for a further function by also applying symmetric RF signals "DS" to enhance desolvation, as earlier discussed.

Cleansing gas G is introduced at port P1 to further enhance desolvation. This gas flows opposite to the guided ions in chamber 93 and exhausts out ports P2, P3. Preferably, this is operated with no pressure gradient across orifice 31.

In order to improve spray conditions, the separation 20S between the tip 20 and the top guiding electrode F1 can be adjusted in practice of the invention. In one practice, the position of housing 12a can be adjusted relative to base B, which in turn adjusts the separation 20S. In an alternative, the height of head 12 can be adjusted relative to electrode F1.

Figure 9B:
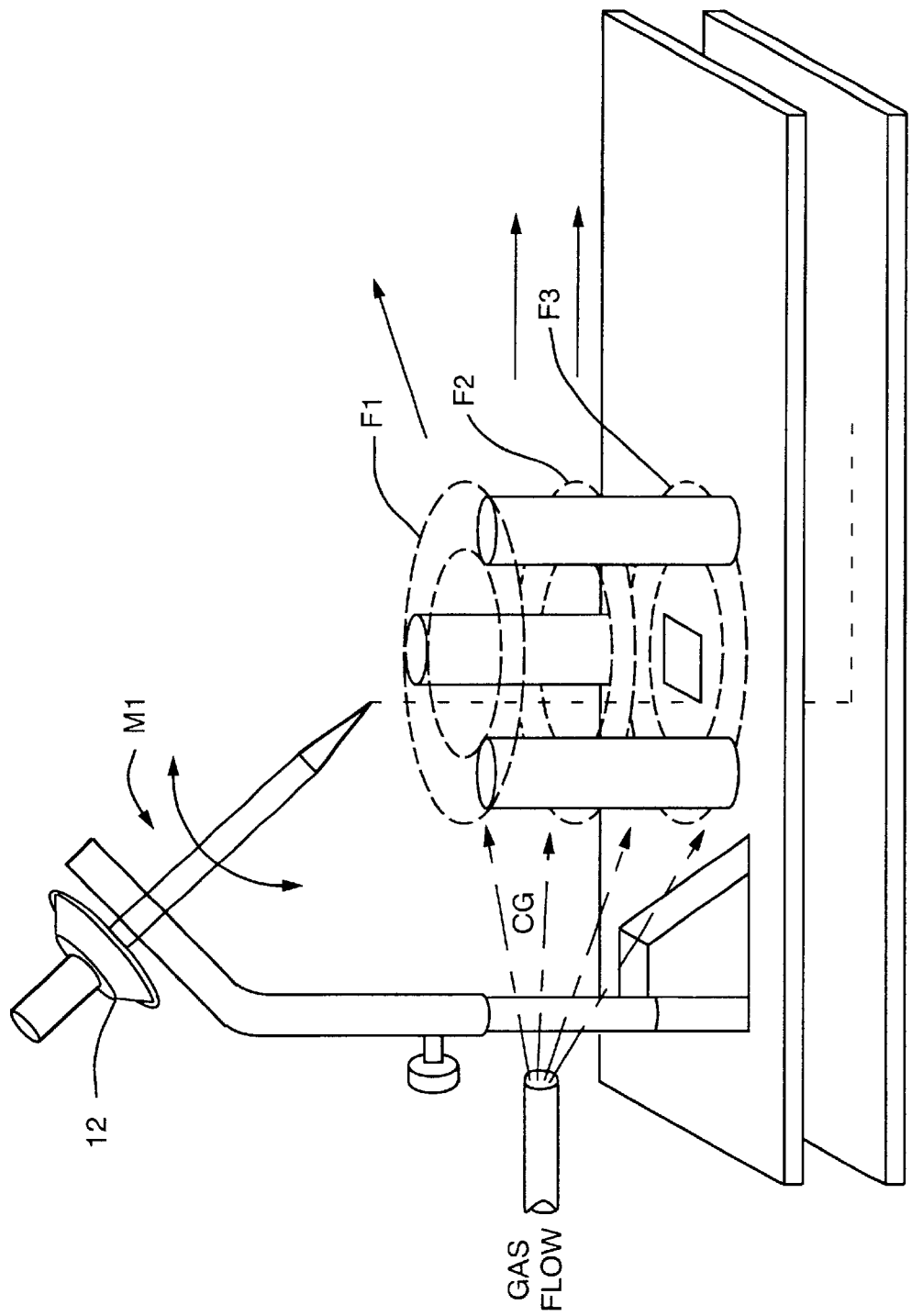
FIG. 9B shows an electrospray head cooperating with guiding electrodes in practice of the invention.

In an alternative embodiment, as shown in FIGS. 9A and 9B, spaced apart guiding electrodes F (FIG. 9A) or F1, F2, F3 (FIG. 9B) are bathed in a curtain gas flow CG. This flow may be unconfined or contained within housing H1. The electrospray head 12 is adjustably mounted in mount M1, wherein its angle of delivery can be adjusted relative to the surface of substrate 52. In addition, its height can be adjusted relative to the substrate.

Referring again to FIG. 4A, sample reservoir 92 receives a liquid sample S, which is then ionized and filtered as set forth above. In such embodiment, a single spectrometer chip 100 integrates both a ionization source, such as part of a microfluidic electrospray module 80', and planar high field asymmetric waveform ion mobility filter 40. An internal detector may also be included, or ions are outputted for detection. Various micro-fabricated micro-fluidic components may be used as an ion source, or combinations thereof, including electrospray, nano-electrospray, liquid chromatography, electrophoresis separation.

In another embodiment, the electrospray head 80' of FIG. 4A may be attached to substrate 52 (preferably through anodic bonding or brazing). Guiding electrodes 82 and 84 are not required in this embodiment.

Figure 4D:
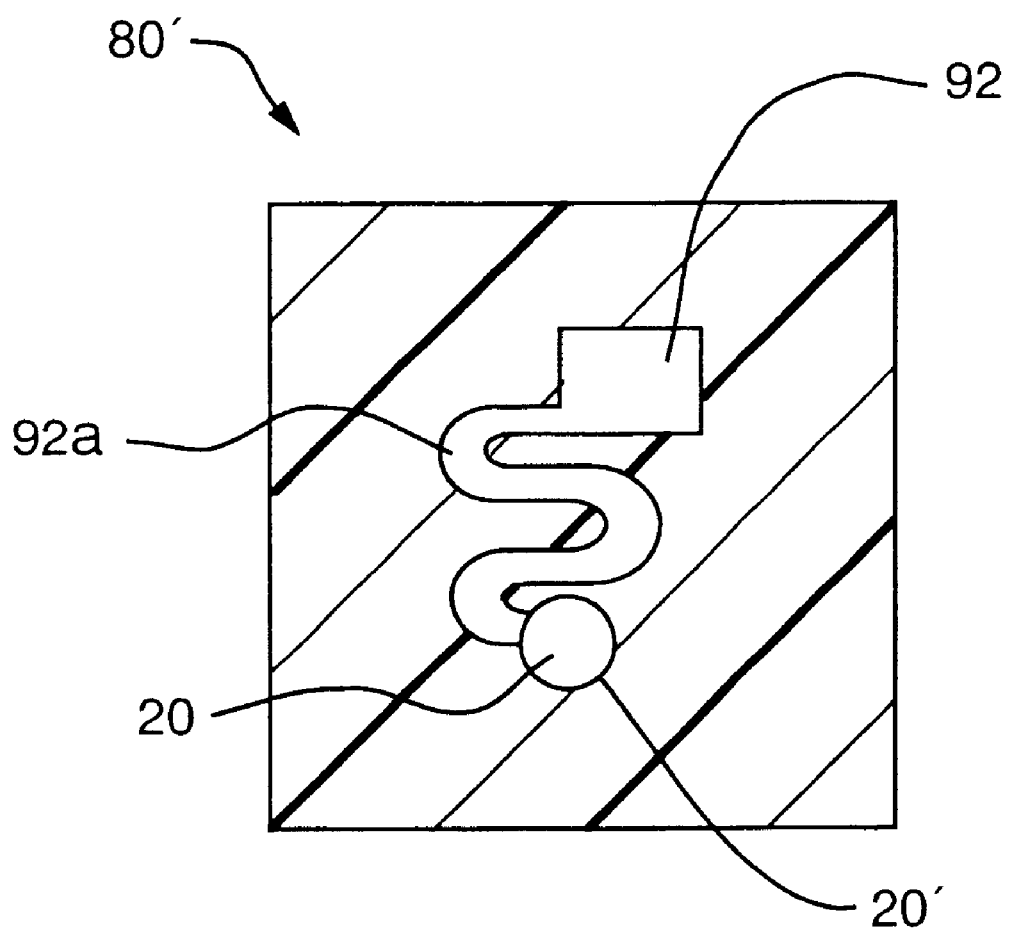
FIG. 4D shows an electrospray head with a sample reservoir feeding a separation channel leading to a spray tip in practice of the invention.

In the embodiment of FIG. 4D, the microfluidic electrospray module 80' includes sample reservoir 92 feeding a lengthened, serpentine, separation channel 92a, leading to tip orifice 20' and then to tip 20. The channel 92a may be a liquid chromatograph or electrophoretic separator, or the like, for conditioning or separating constituents in the sample prior to ionization at the tip 20.

The motivation for such a chip 100, with or without a microfluidic module, is to eliminate variability in sample preparation and analysis, this is achieved by reducing human interaction and by providing a device that incorporates all key components in a single structure. These chips 100 lend themselves to low cost manufacturing and as a result can be disposable. Using a new chip for each sample analysis eliminates sample to sample cross-contamination. Additionally, through the reduction in human intervention, sample preparation time is reduced. In a conventional arrangement the position of the electrospray tip or microfluidic component, must be re-adjusted each time relative to any filter or mass spectrometer inlet. This adds time and cost. With the integrated micro-fluidics chip/PFAIMS apparatus of the invention, the relative positions of the microfluidic components and PFAIMS inlet are fixed. Once analysis is completed the entire chip is simply discarded and a new chip is loaded with a sample to be analyzed and possibly to be mounted on a mass spectrometer. This allows for significantly faster analysis times and higher throughput.

Figure 10A:
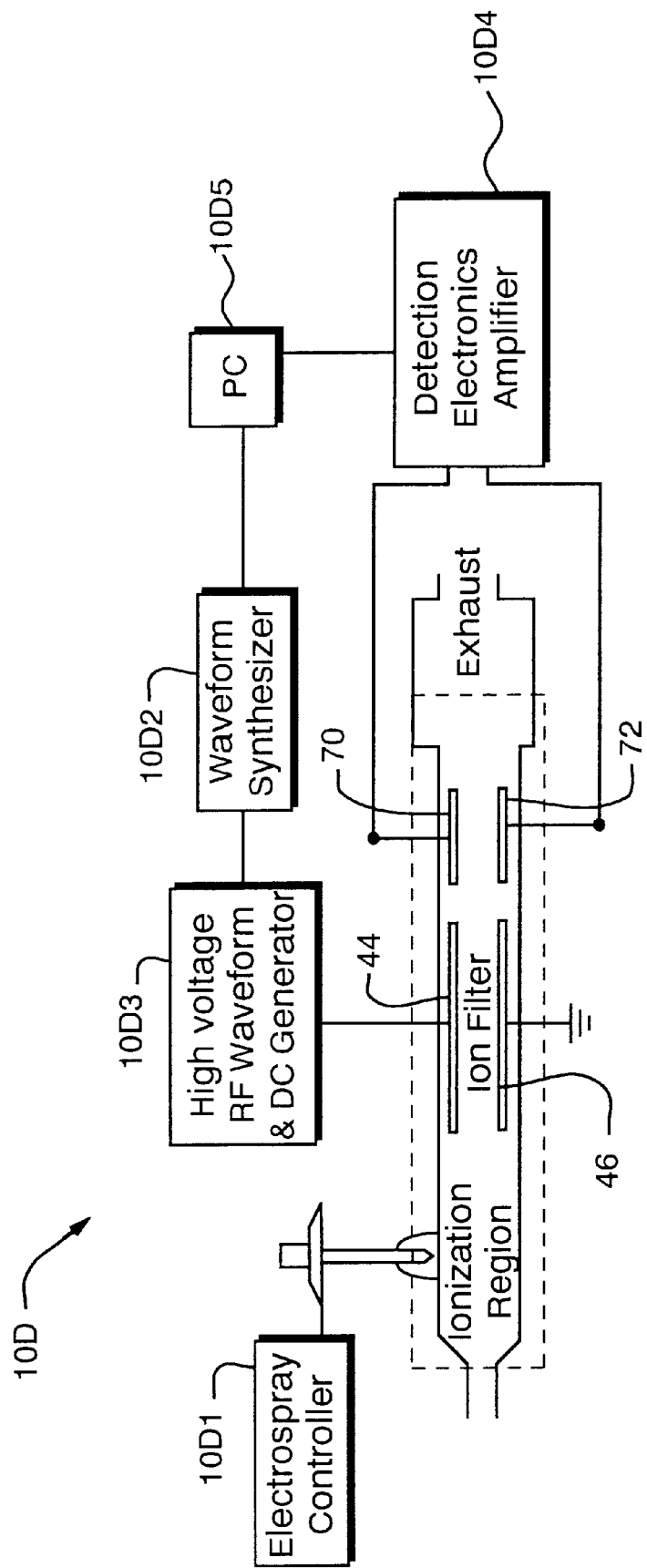
FIG. 10A shows the control system in practice of the invention.
Figure 10B:
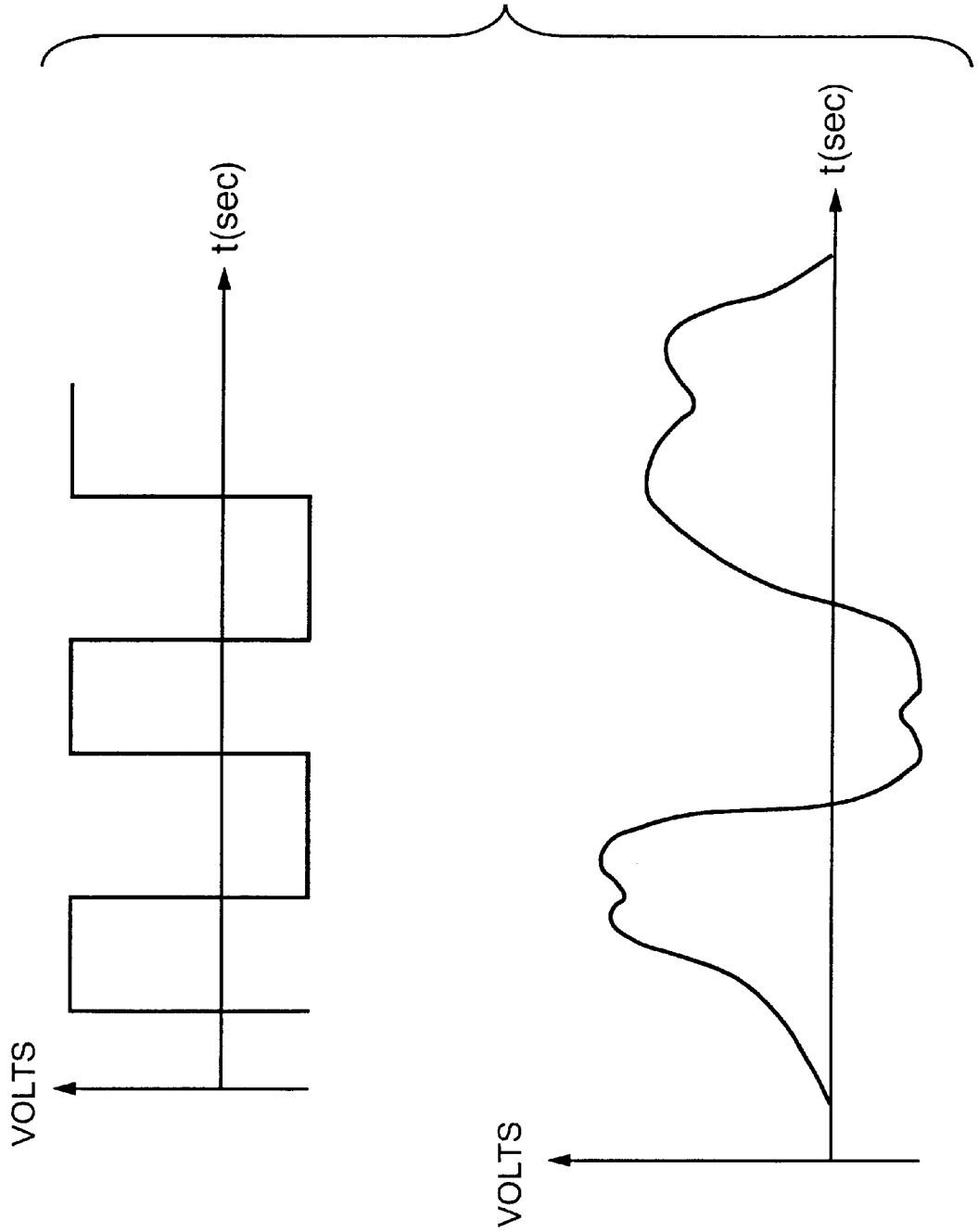
FIG. 10B shows control signals in practice of the invention.

In an illustrative embodiment of the invention, shown in FIG. 10A, controller 10D includes several subsystems, including an electrospray control 10D1, a waveform generator (synthesizer) 10D2 cooperating with high voltage RF waveform & DC generator 10D3 for applying the RF asymmetric drive signal and DC control bias to filter electrodes 44, 46, and detection electronics 10D4 for detection of ions on the detector electrodes. Computer 10D5 collects data and controls the system. In one embodiment, the RF field is produced in generator 10D3 by a soft-switched semi-resonant circuit that incorporates a flyback transformer to rapidly generate the high voltage pulses. The circuit provides a peak-to-peak RF voltage of at least 1400 volts at a frequency of around 100 KHz –4 MHz with a duty cycle of about 10–70%. Sample RF waveforms for driving the filter electrodes are shown in FIG. 10B, although variations thereof are also within practice of the invention.

Figure 11A:
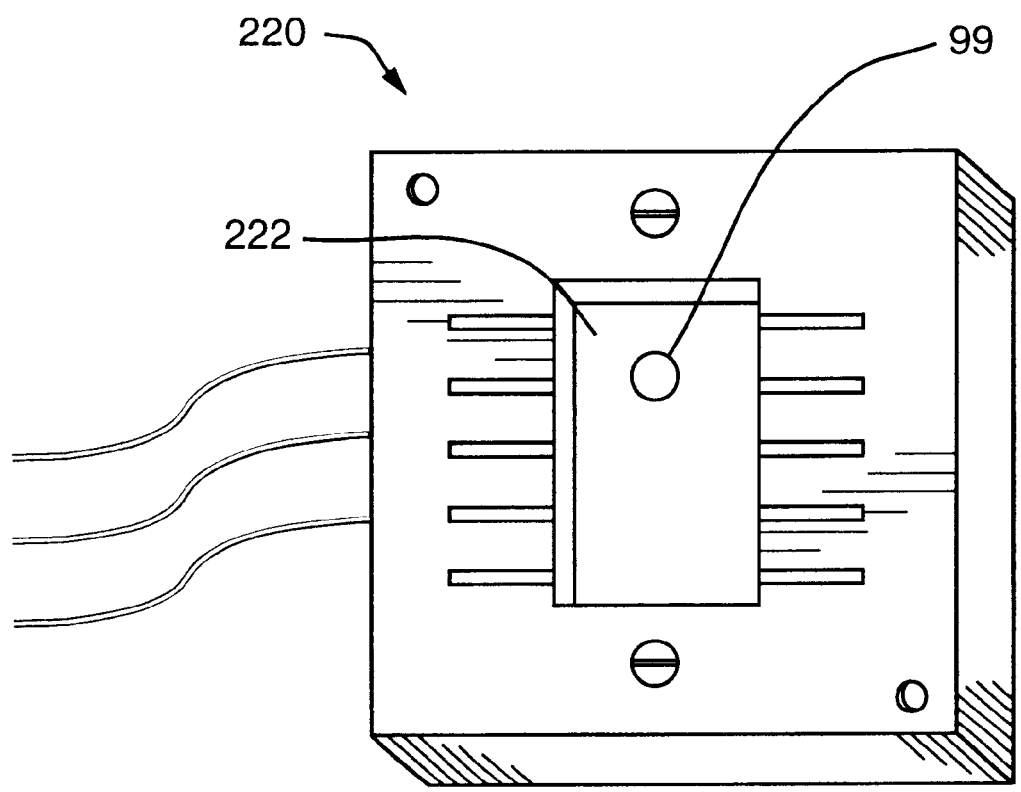
FIG. 11A shows a chip receptacle in practice of the invention.
Figure 11B:
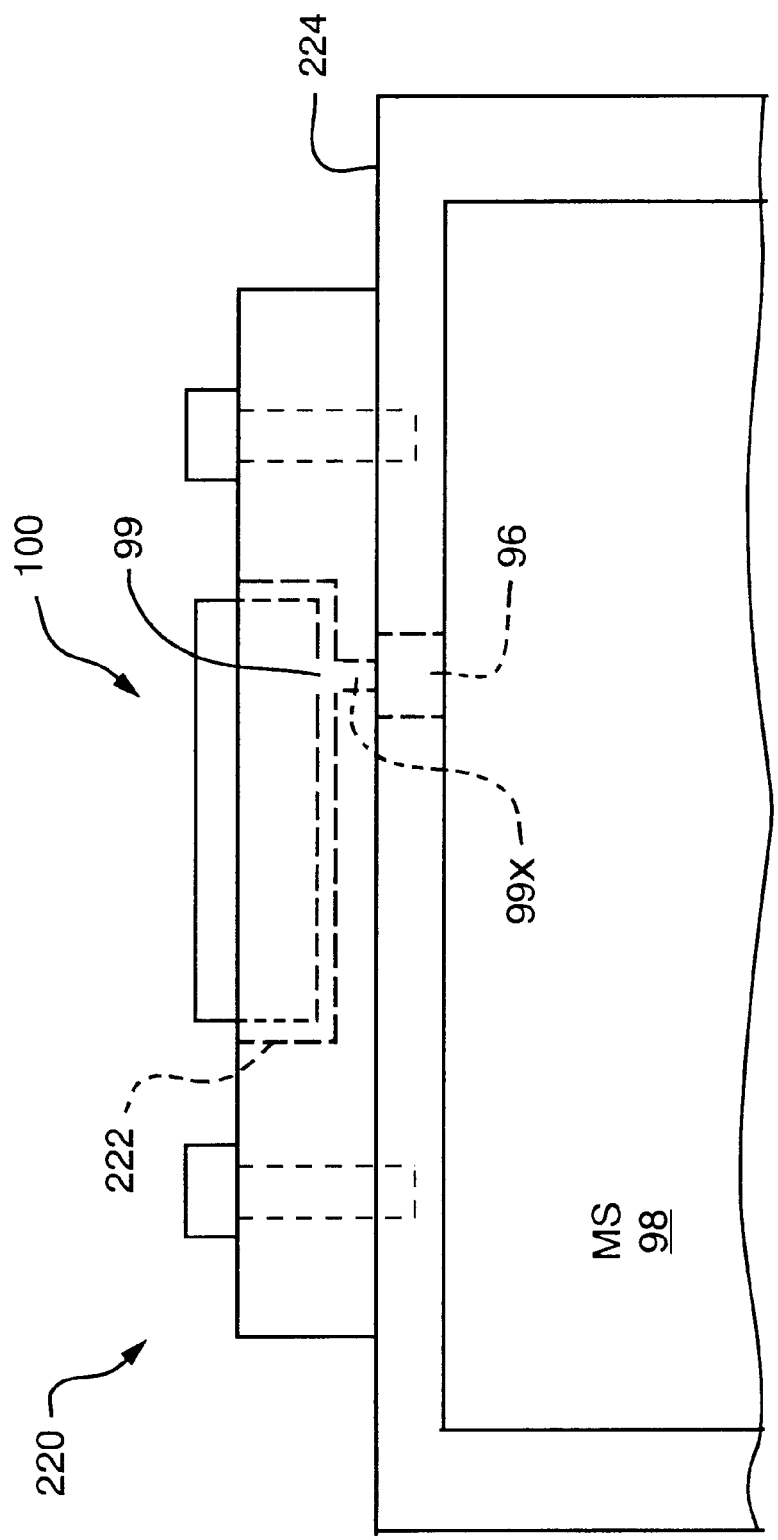
FIG. 11B shows a chip receptacle interfaced with a mass spectrometer in practice of the invention.

Preferably the chip 100 is inserted into a chip receiver assembly 220. Assembly 220 includes a socket 222 for receipt of the chip. The socket is electrically connected to the controller 10D. A preferred embodiment of chip receiver 220 serves a further function of coupling the chemical sensor system 10 to a mass spectrometer MS 98, as shown in FIG. 11B. Chip receiver assembly 220 is affixed to the face 224 of the mass spectrometer, such that outlet orifice 99 of system 10 is aligned via orifice 99x with the MS orifice inlet 96, whereby ions 24' are directed into the MS for detection and analysis.

Detection of ions 24 passing through filter 40 may be made as described above in conjunction with the detector electrodes 70, 72 of FIG. 3A. An alternative embodiment is shown in FIG. 3B where electrode 70 is now used as a deflector electrode to deflect ions 24' toward intake 96 of mass spectrometer 98. The ions are guided or focused by focusing electrodes 72a, 72b and pass through an orifice 99 in substrate 54' and through plenum gas chamber 101 via a mounting adapter 102. Providing a low flow rate plenum gas into chamber 101 prevents neutralized sample ions or solvent molecules from entering the mass spectrometer intake 96. Ions that are focused into the mass spectrometer intake are then detected according to standard mass spectrometer procedures. It will be appreciated that the plenum chamber 101 is not shown in FIG. 11B, although it may be beneficially used in this embodiment.

An assembly of the invention can be easily mounted right up against the mass spectrometer inlet 96 (with or without a plenum chamber), as shown in FIGS. 3B, 11B and 12A–12B, for example. The deflector electrode (side mounting FIG. 3B or 12A–12B) allows almost 100% of ions to be deflected into the mass spectrometer.

Figure 12A:
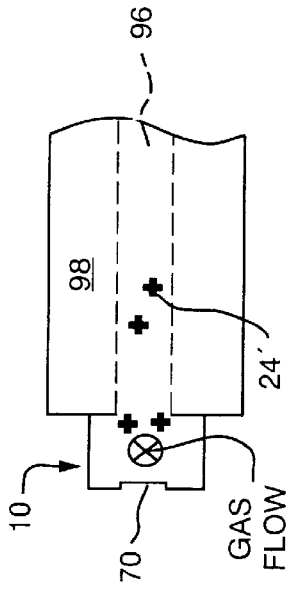
FIGS. 12A, 12B shows planar FAIMS in practice of the invention.
Figure 12B:
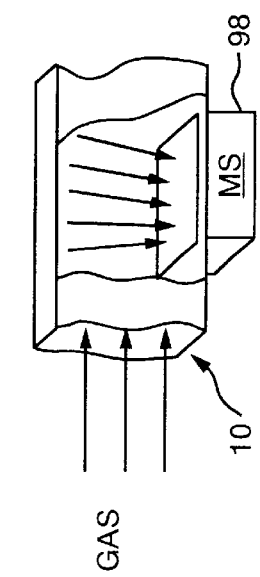
Figure 12C:
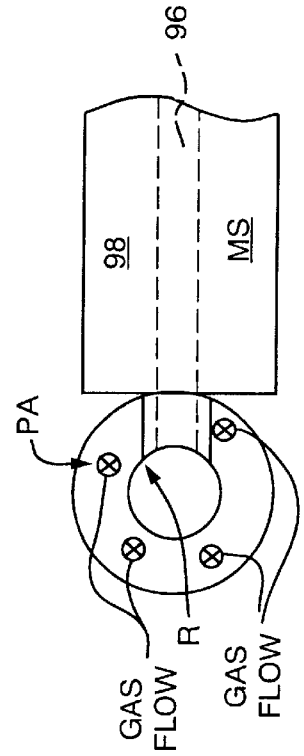
FIGS. 12C, 12D shows prior art cylindrical FAIMS devices.
Figure 12D:
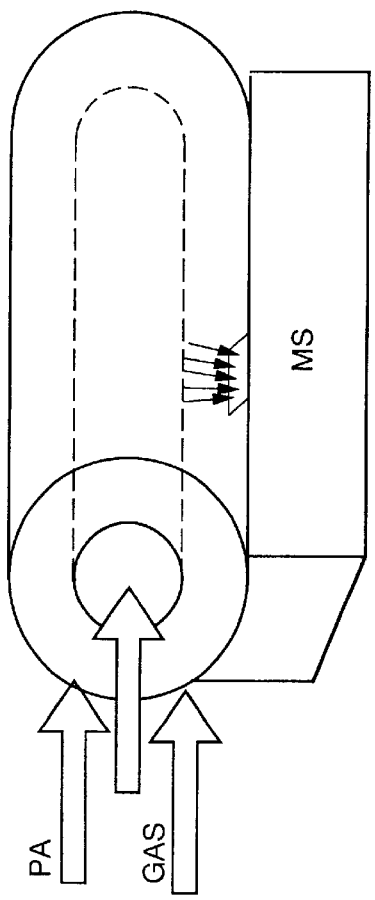

This high efficiency is in contrast with the prior art cylindrical design in FIGS. 12C–12D, mounted to inlet 96 of the mass spectrometer, where only a small fraction of the total ions in the drift tube are affected by the electric field which propels them into inlet 96 and resulting in only a fraction of the available ions being detected in the prior art.

It will now be appreciated that in practice of the invention, chemical analysis can be performed using any of several ion detectors. In the embodiments of FIGS. 3A and 4A, the detector is entirely internal to the assembly 10. In the embodiment of FIG. 3B, assembly 10 is intimately mated via adapter 102 to the mass spectrometer 98 as a detector. In the embodiment of FIG. 3B, if the current on focusing electrodes 72a, 72b is monitored, then additional detector information is available for processing the detection information of mass spectrometer 98. Even without focusing electrodes 72a, 72b, a FAIMS spectra of the invention can be reconstructed by monitoring the total ion current in the mass spectrometer.

Figure 13A:
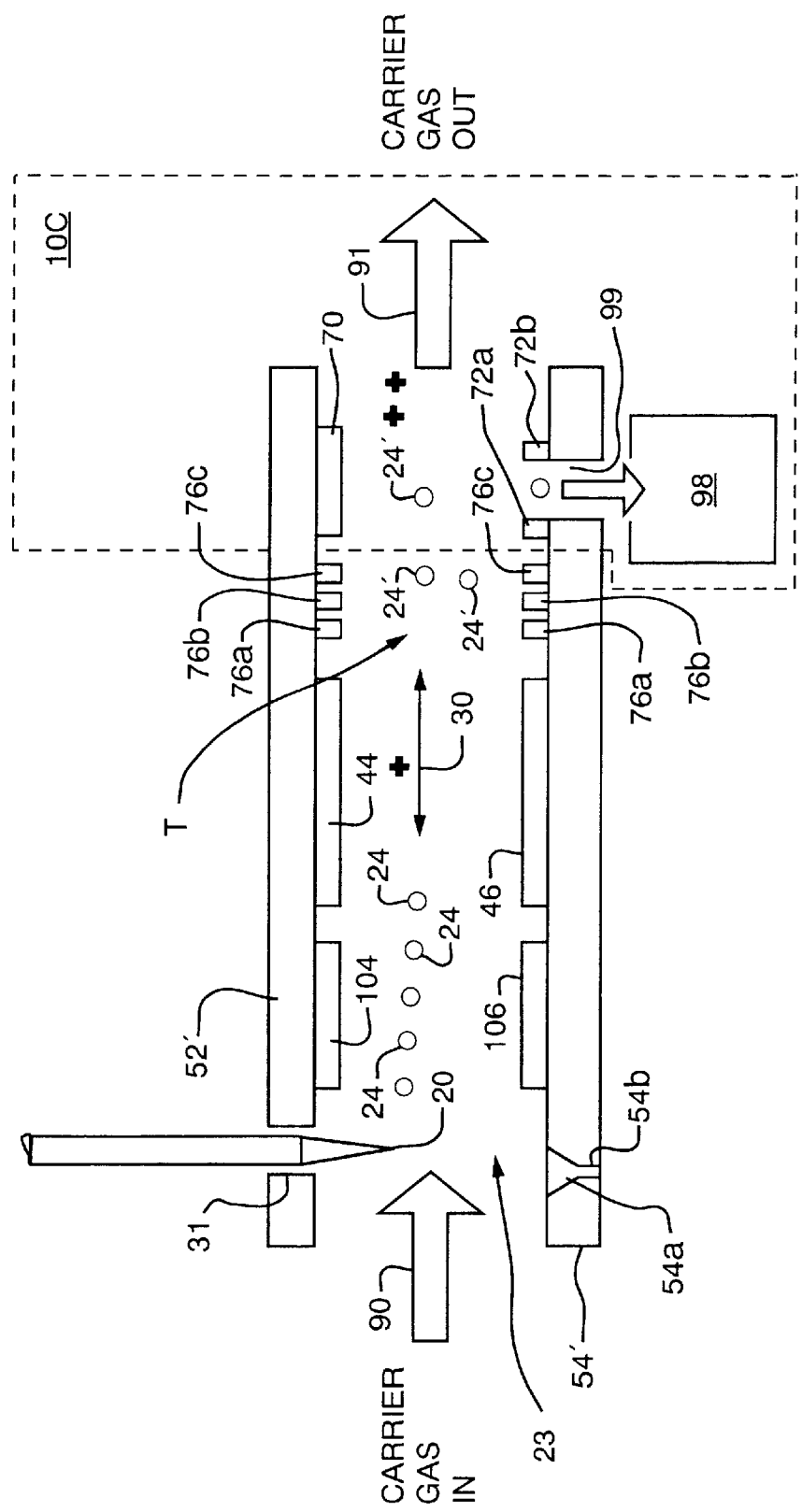
FIGS. 13A, 13B shows an electrospray tip inserted within the ion region, either from above through orifice in upper substrate or from the side in practice of the invention.
Figure 13B:
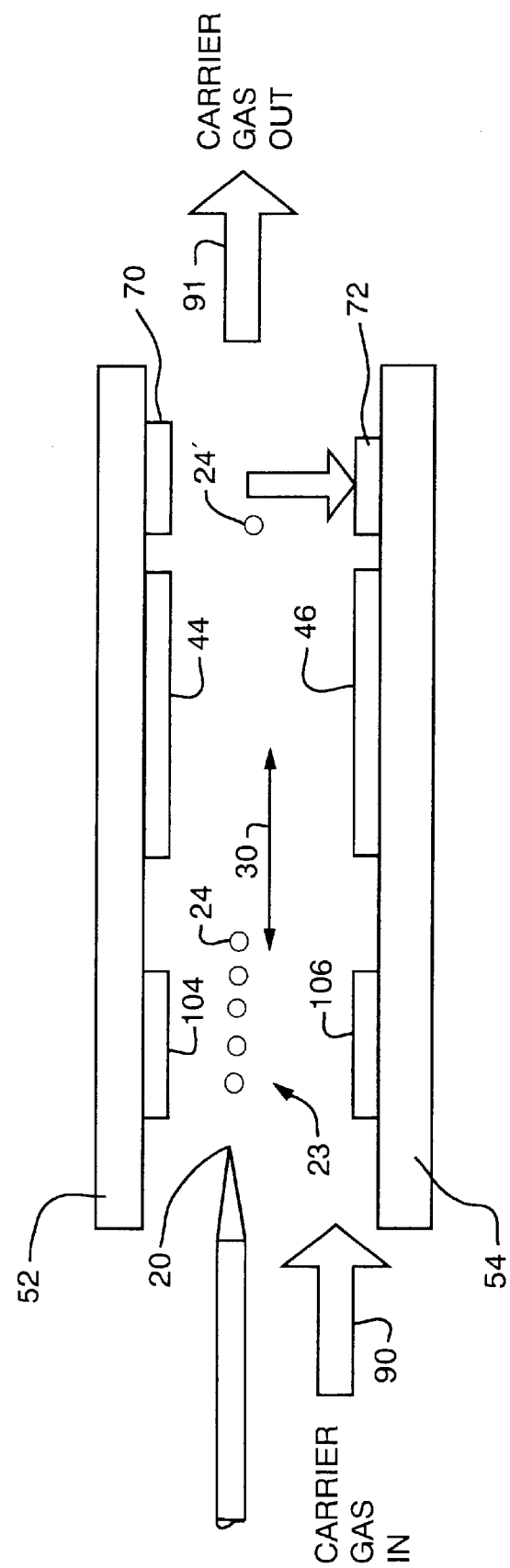

Alternative embodiments of the invention are shown in FIGS. 13A, 13B where the electrospray tip 20 has been inserted within ion region 23, either from above through orifice 31 in upper substrate 52' (FIG. 13A) or from the side (FIG. 13B). Attractor electrodes 104, 106 attract and guide the ions in the flow path 30 as they travel in gas flow 90 toward filter electrodes 44, 46. In FIG. 13A, droplets from the electrospray tip 20 collect in reservoir 54a, which also may be provided with a drain hole 54b.

It is desirable to concentrate ions after they pass through the ion filter and before entering output section 10C. This improves the signal to noise ratio at the detector and improves sensitivity. An ion trap or ion well can collect ions in this manner, concentrating them and then delivering the concentrated ions at once to the output section. Neutrals are not collected in the ion trap and are continuously being removed by the gas flow from the ion trap T.

An ion trap can be applied to many embodiments of the invention, such as in FIGS. 3A,B,C, for example. An illustrative embodiment is shown in FIG. 13A, where an ion trap T is formed with several appropriately biased electrode pair. In one example, for positive ions, the electrodes are biased such that a potential minimum is formed in the region of electrode pair 76b and potentials on electrode pairs 76a and 76c are higher. Ions are allowed to accumulate in the trap, and after a desired amount of time resulting in collection of a desired number of ions, the trap can be opened by adjusting the voltages applied to electrodes 76a, 76b and 76c. When the trap is opened, the trapped ions 24' flow into the output section 10C.

Figure 14A:
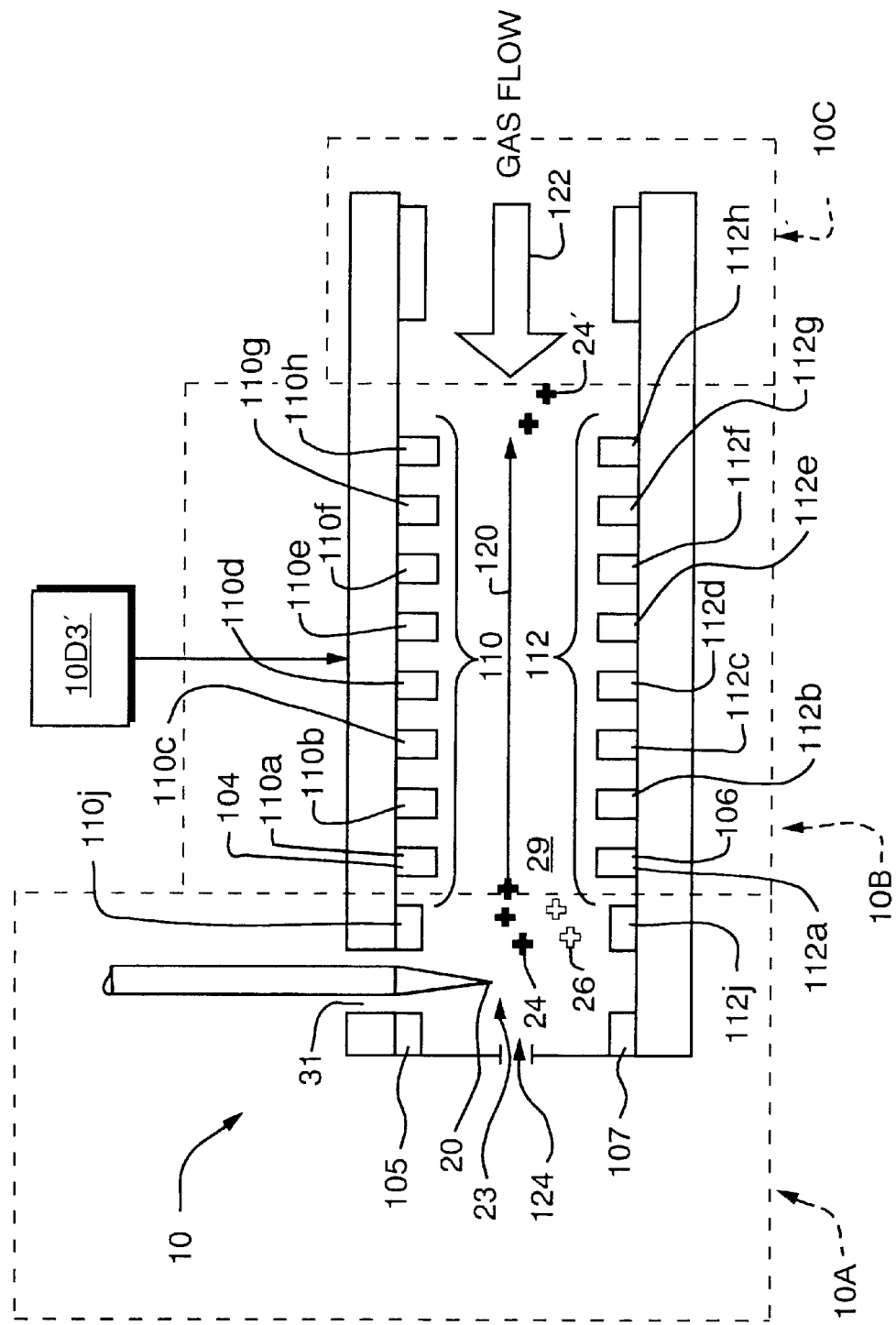
FIGS. 14A, 14B shows longitudinal electric field driven embodiments in practice of the invention.
Figure 14B:
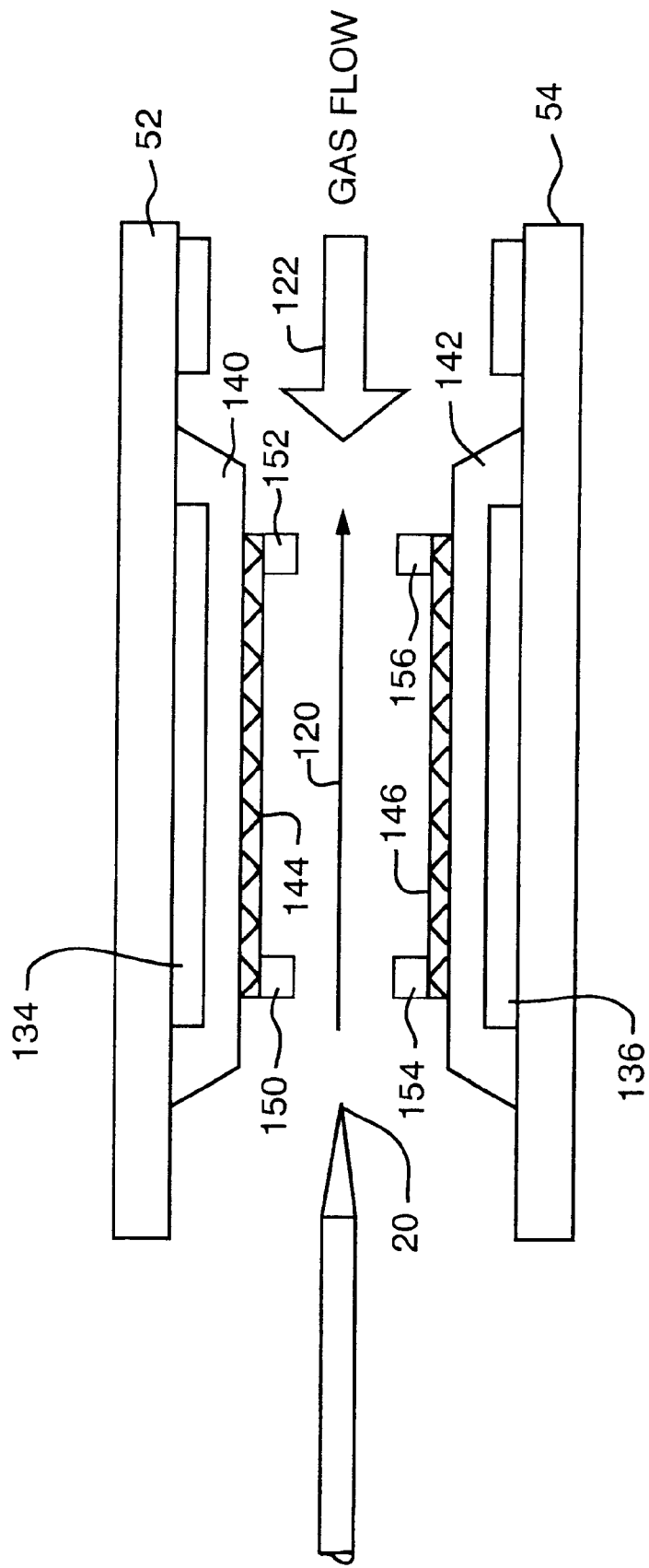

In the embodiments discussed above, ion filter 40 includes spaced electrodes 44, 46 which are driven by the RF and DC generator 10D3 as ions are propelled by gas flow 90 in drift tube 29. In the embodiment of FIGS. 14A, 14B, a longitudinal electric field driven embodiment of the invention, a novel method of conveying the ions in the drift tube 29 is shown.

In the embodiments of FIGS. 14A, 14B, the ions are propelled toward the output section 10C using a longitudinal electric field generated by electrodes 110 and 112. These embodiments feature a simplified gas flow structure in a very compact design, and gas flow is even optional.

In one embodiment, ions actually travel in an opposite direction to gas flow 122, and are propelled by electric field vector 120. This gas flow opposite to the ion travel direction enhances the desolvation of the sample ions. It also maintains a clean ion filter 40 free of neutral sample molecules. This consequently decreases the level of ion cluster formation resulting in more accurate detection of ion species. Furthermore the counter gas flow clears out and reduces memory effects of previous samples in ionization region 23. This embodiment can include integrated electrospray tip 20 inserted within ion region 23 from above, or side mounted, as are shown.

In the longitudinal electric field driven embodiments of FIGS. 14A, 14B, ions 24, 26 are conveyed without gas flow 122 but rather by action of a longitudinal electric field produced by sets of cooperating electrodes 110, 112 along with a longitudinal RF & DC generator 10D3'. As an example of the operation of the PFAIMS in a particular electrode bias scheme, several or all of the electrode pairs 110a–h, 112a–h have the same RF voltage applied, while the DC potentials are stepped so that a longitudinal potential gradient is formed to drive the ions towards the detector. This embodiment can operate without a gas flow or optionally can include an exhaust gas flow 122 which exhausts neutrals and solvent molecules out exhaust port 124.

In one example, electrodes 110, 112a might have 10vdc applied thereto and electrodes 110h, 112h then might have 100vdc applied. Now negative ions in region 10A are attracted by electrode pair 110a–112a and further attracted by pair 110h, 112h, and their momentum then carries them into detector region 10C if passed by the filter.

The RF and compensation may be applied to various of the electrodes 110a–h, 112a–h, and will operate in the manner set forth above.

In another embodiment of FIG. 14A the electrospray tip can be external to ionization region 23 (not shown) above orifice 31 where electrode 112j serves as the attraction electrode. In the longitudinal electric field driven embodiment of FIG. 14B, the ion filter includes spaced resistive layers 144,146 insulated from electrodes 134, 136, by insulating medium 140, 142, for example, a low temperature oxide material. Preferably the substrates are insulating. Resistive layers 144, 146 are preferably a ceramic material deposited on insulating layers 140,142. Terminal electrode pairs 150, 152, 154, 156 make contact with a resistive layer and enable a voltage drop across each resistive layer to generate the longitudinal electric field vector 120. Electrodes 150 and 154 are biased according to application, for example they may be at 1000 volts while electrodes 152 and 156 may be at zero volts.

When the embodiment of FIG. 14B is implemented in a cylindrical design, then the electrodes 150 and 154 form a ring electrode, and electrodes 152 and 156 form a ring electrode, and resistive layers 144, 146 form a cylinder.

The present invention can also perform time of flight ion mobility spectrometry functions. For example, in the embodiment of FIG. 14A, electrodes 104, 106 are pulsed to draw a sample from tip 20 that is ionized, starting the time cycle. Electrodes 110a–h, 112a–h are biased relative to their neighbors so that the ions are driven by the generated longitudinal electric field gradient towards output section 10C. A counter gas flow 122 can be applied to sweep sample neutrals away. A combination of these electrodes can be used to form the ion trap T described above (see FIG. 13A).

Figure 15A:
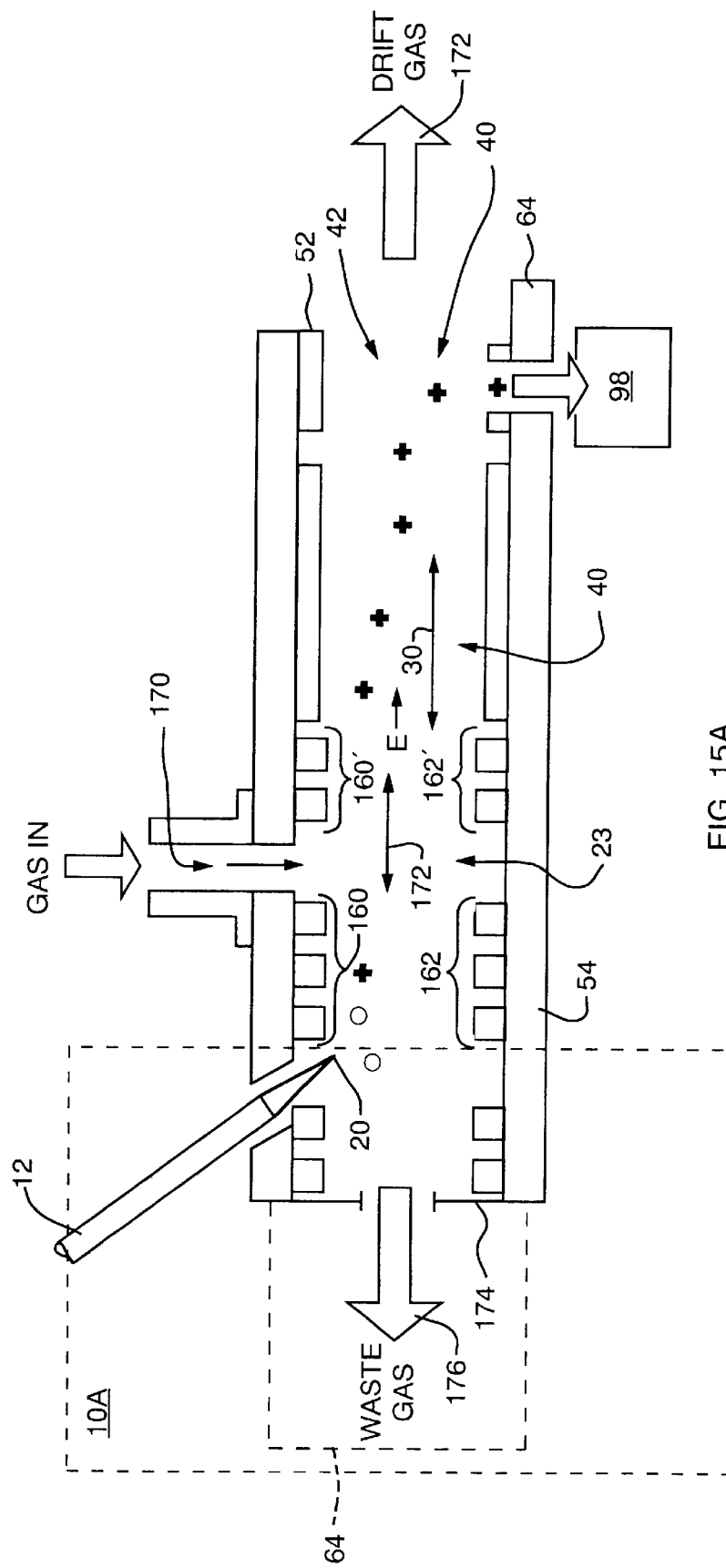
FIGS. 15A, 15B show split gas flow embodiments in practice of the invention.

In the split gas flow embodiment of FIG. 15A, the electrospray needle 12 is inserted through substrate 52 and into ion region 23, however, it may be mounted externally to the drift tube such as in FIG. 3A. The ion flow generator in this design includes a plurality of segmented electrodes 160, 162 on opposite sides of flow path 30 to create longitudinal electric field E. In the preferred embodiment, one or more discrete electrodes 160, 162' are located downstream of gas inlet 170 to extend longitudinal electric field E beyond the split flow of gas, and thereby ensuring that ions flow into filter 40 as carried by drift gas flow stream 172.

Figure 15B:
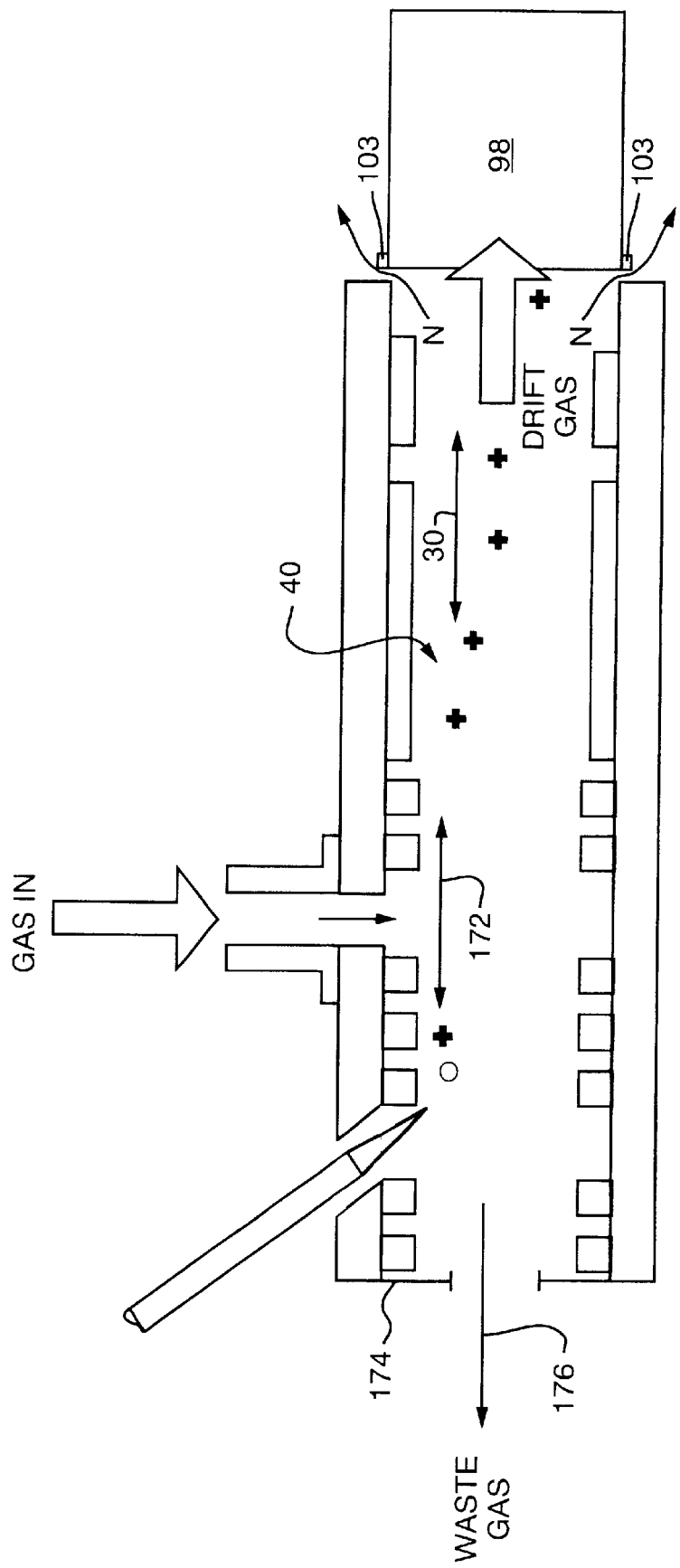

In the embodiment of FIG. 15B, mass spectrometer 98 is directly coupled to the end of the drift tube 30. An advantage of this design is that the ion filter 40 is kept free of sample neutrals by virtue of the split gas flow. This prevents clustering of neutral sample molecules with ions, and this results in higher detection accuracy. A venting device 103 for venting of neutrals N keeps neutrals out of the MS intake.

A baffle 174 may be placed as shown to regulate the velocity of waste gas flow stream 176 relative to the velocity of drift gas flow stream 172. Typically, drift gas flow stream 172 is at a higher velocity than waste gas flow stream 176. Other means for creating a waste gas flow stream of a velocity different than the drift gas flow stream, however, are within the scope of this invention.

In the embodiments of FIGS. 15A, 15B, various sample preparation sections can be used, whether simple a port to draw in ambient air samples, or electrospray, gas chromatograph, liquid chromatograph, or the like. Regardless of what is used, the split gas embodiment shown can prevent clustering and allows better identification of ion species.

Generally the sample ions tend to be found in monomer or cluster states. The relationship between the amount of monomer and cluster ions for a given ion species is dependent of the concentration of sample and the particular experimental conditions (e.g., moisture, temperature, flow rate, intensity of RF-electric field). Both the monomer and cluster states provide useful information for chemical identification. It will be useful to investigate the same sample separately in a condition which promotes clustering, and in an environment that promotes the formation of only the monomer ions. A planar two channel PFAIMS of an embodiment such as shown in FIG. 16 can be used to achieve this.

Figure 16:
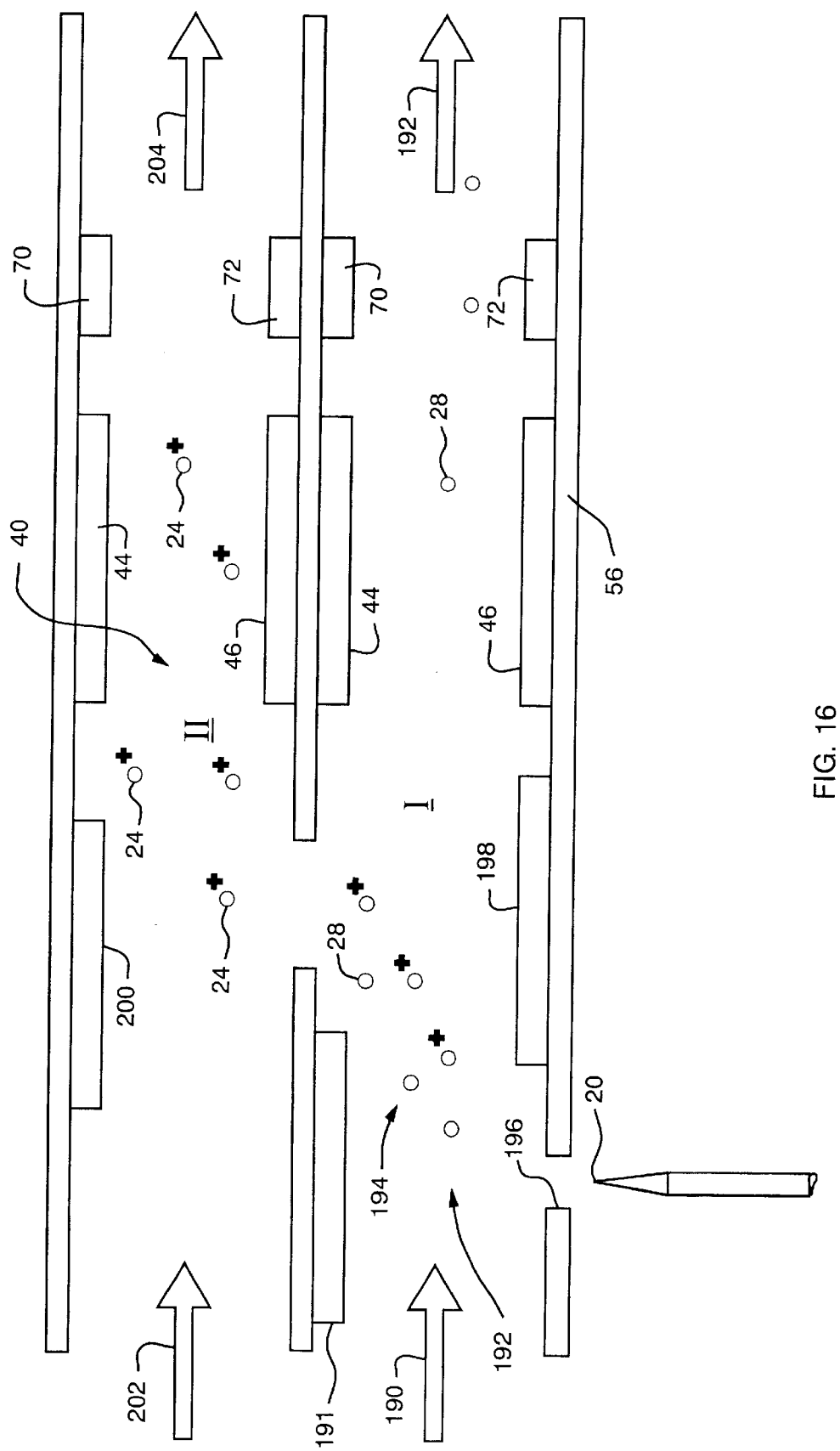
FIG. 16 shows a dual channel embodiment in practice of the invention.

In the dual channel embodiment of FIG. 16, a first channel "I" is shown for receipt of ions 24, and molecules 28 in a drift gas flow 190 in ion region 194. Also included are PFAIMS filter electrodes 44, 46 and detector electrodes 70, 72.

To interrogate the sample ions in the monomer state, the ions are extracted from the flow stream (by action of an electric field between electrodes 198 and 200) and they flow up into upper chamber "II". The neutral molecules 28, typically solvent, continue to flow through channel "I" and exit at drift gas exhaust 192. The potential difference between the electrospray tip 20 and the attraction electrode 191 accelerates the ions into the ion region 194 through orifice 196 in substrate 56. A second gas flow 202 prevents the sample neutrals from entering chamber "II" and carries ions 24 to PFAIMS filter 40 (electrodes 44, 46 in Chamber II), and the passed ions are then detected, such as with detector electrodes 70, 72 as in FIG. 3A or with a mass spectrometer as in FIG. 3B. The second gas flow 202 exhausts as flow 204. When the deflection and attractor electrodes 198, 200 are not energized, then the sample ions can be observed in the cluster state in chamber "I" by the local detector electrodes 72 and 70. By alternatively energizing and not energizing electrodes 198 and 200 significantly more information can be obtained to better identify the chemical sample.

Figure 17:
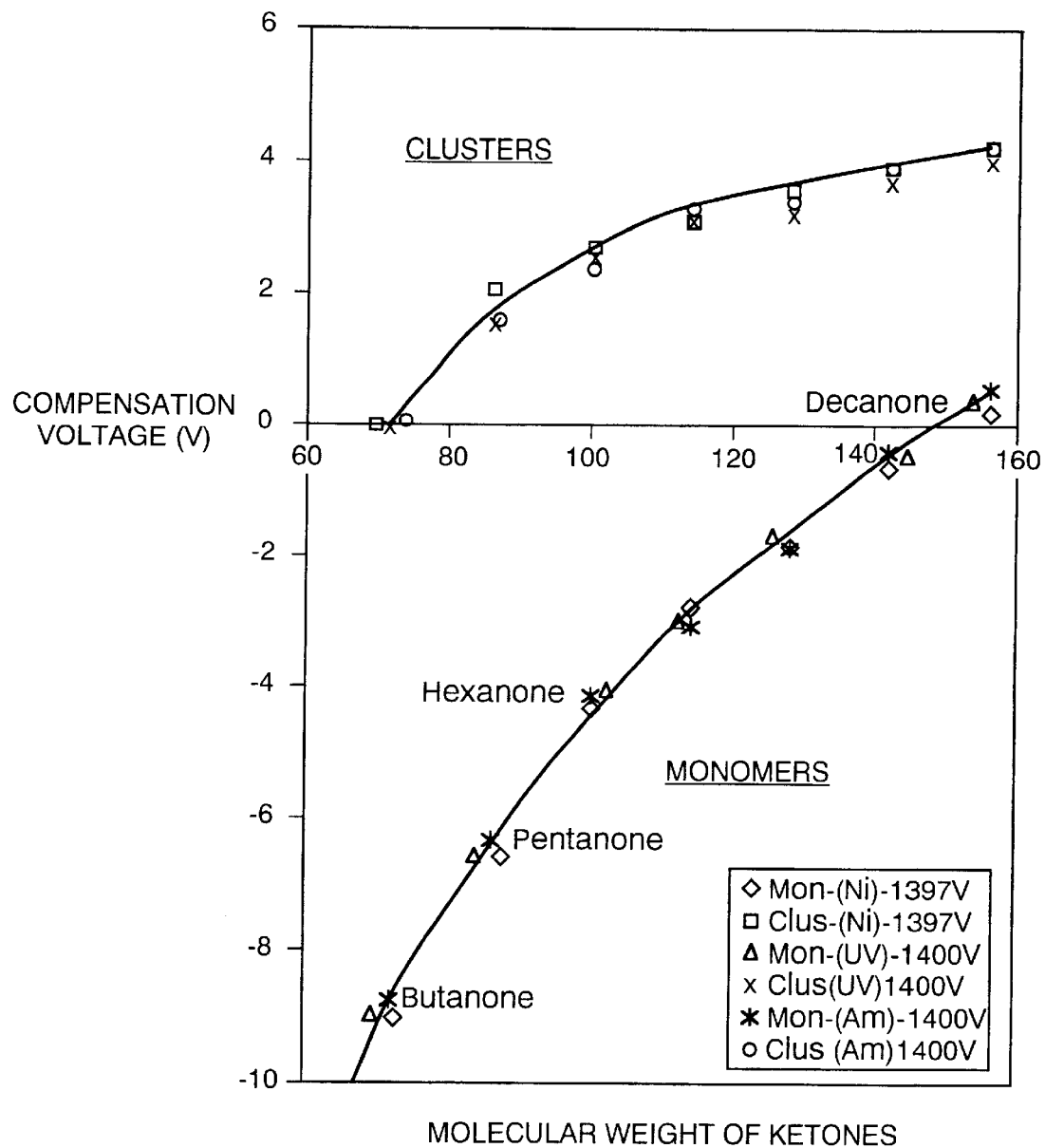
FIG. 17 shows dependence of Ketones on compensation voltage for different ionization sources in practice of the invention.

FIG. 17 shows a homologous series of Ketone samples obtained in one practice of the invention, ranging from Butanone to Decanone. From the figure it is evident that for the same chemical species the cluster ions (top plot) require very different compensation signals compared to the monomer ions (bottom plot). So by observing the difference in peak position of the monomer and cluster peak the level of identification of the chemical compound can be significantly increased. For example, for Butanone the peak position in the monomer state occurs close to −9 volts while the cluster peak is around zero. For Decanone for example, the monomer peak is close to zero while the cluster peak is at around +4 volts.

Figure 18:
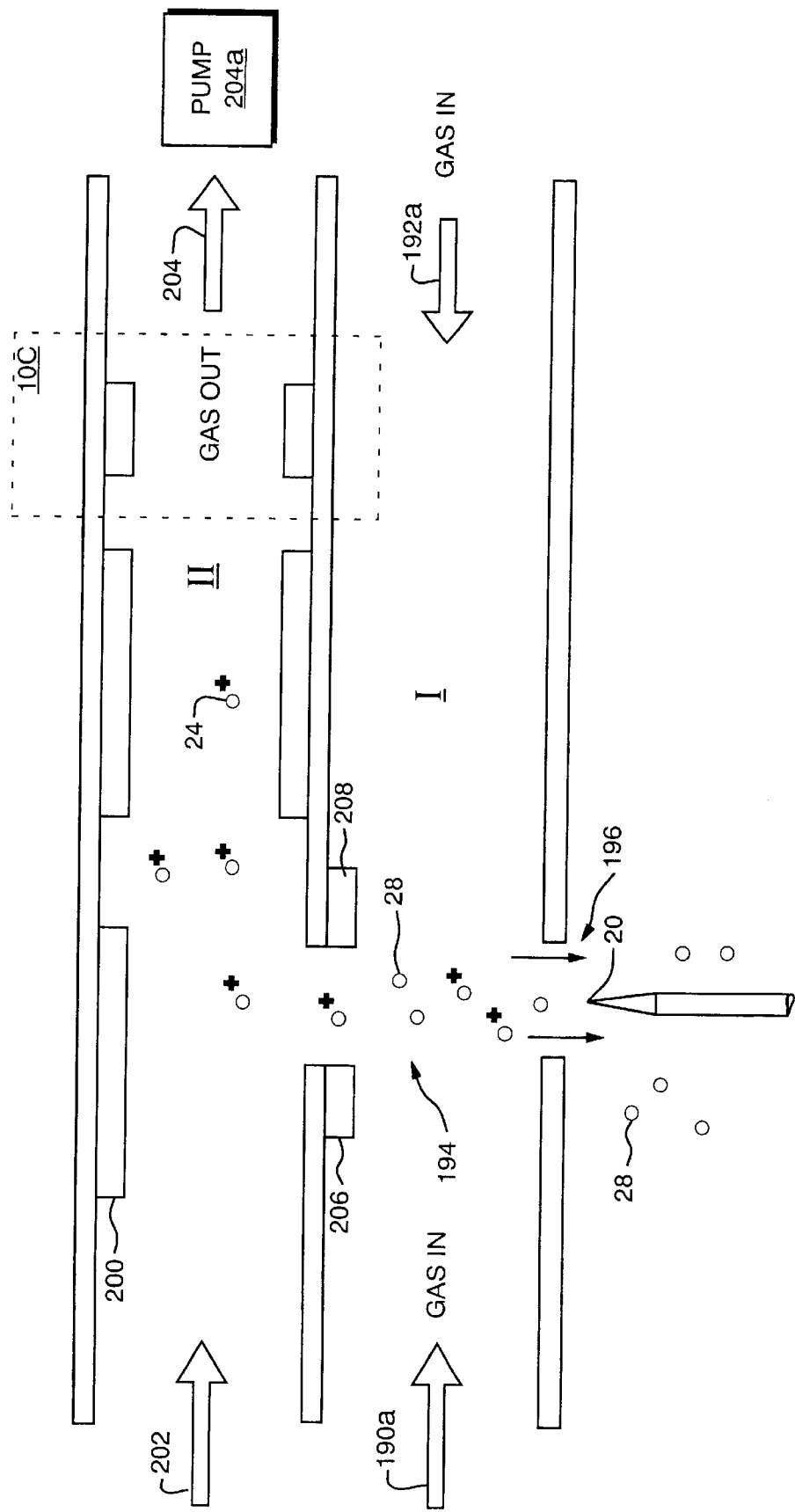
FIG. 18 shows a dual channel embodiment in practice of the invention.

The motivation for the embodiment shown in FIG. 18 is the same as that of embodiment 16. In this system switching between a monomer state and cluster state operating condition is achieved by control of a curtain gas flow 190a and 192a. With the curtain gas applied, sample neutrals 28 are prevented from entering channel "II" and ions in the monomer state can be investigated. Curtain gases 190a and 192a may flow in the same direction and exhaust at orifice 196 for example. Meanwhile the gas flows in channel "II" remain in the same configuration as the system in FIG. 16 Guiding electrodes 206 and 208 are included to guide the ions into channel "II". Attraction electrode 200 is also used to attract ions into channel "II". When the curtain gas is turned off, ions in the cluster state may be observed since sample neutrals and sample ions may now be drawn into channel "II" using a pump 204a. Gas flows 202 and 204 may also be used. The output section may be connected to a mass spectrometer.

In application of the present invention, the high field asymmetric ion mobility filtering technique uses high frequency high voltage waveforms. The fields are applied perpendicular to ion transport, favoring a planar configuration. This preferred planar configuration allows drift tubes to be fabricated inexpensively with small dimensions, preferably by micromachining. Also, electronics can be miniaturized, and total estimated power can be as low as 4 Watts (unheated) or lower, a level that is suitable for field instrumentation.

We have described novel apparatus that combines electrospray and filtering components. We further disclose micromachined PFAIMS-electrospray interface chips. The PFAIMS-electrospray interface chips offer unique benefits compared to all prior bio-molecule-filtering methods for electrospray mass spectrometry. At the same time this approach can be used in conjunction with many in-liquid separation techniques such as capillary electrophoresis.

Figure 19:
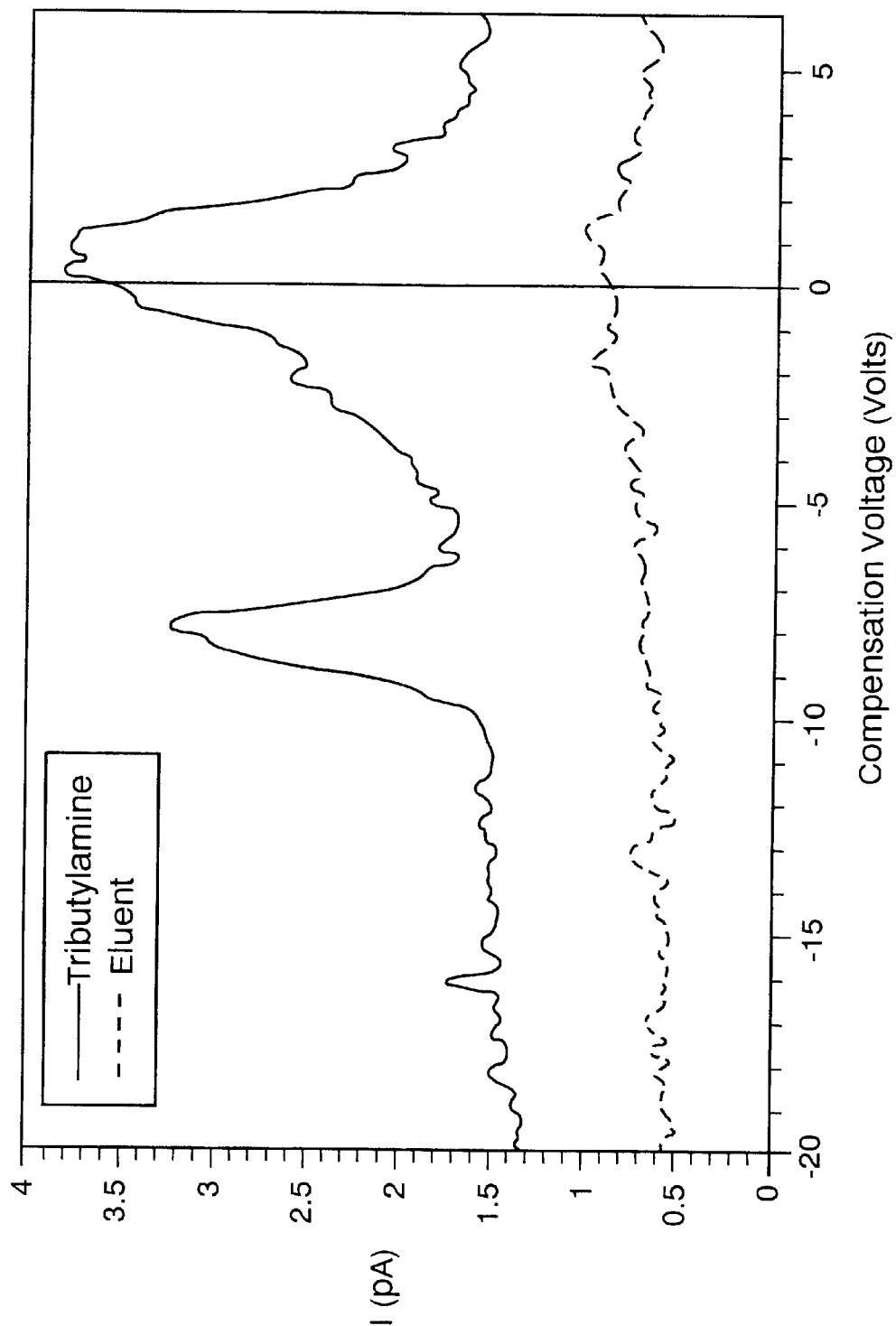
FIG. 19 shows detection spectra in practice of the invention.

In practice of an embodiment of the invention, tributylamine was electrosprayed into the PFAIMS filter and detector. Resulting spectra are shown in FIG. 19 for the amine in solvent and for the solvent eluent alone. There is virtually no response for the eluent alone, and significant response to the amine. This demonstrates practical value and function of the invention.

The present invention provides improved chemical analysis in a compact and low cost package. The present invention overcomes cost, size or performance limitations of prior art TOF-IMS and FAIMS devices, in novel method and apparatus for chemical species discrimination based on ion mobility in a compact, fieldable package. As a result a novel planar, high field asymmetric ion mobility spectrometer device can be intimately coupled with a electrospray tip to achieve a new class of chemical sensor, i.e., either as a standalone device or coupled to an MS. A fieldable, integrated, PFAIMS chemical sensor can be provided that can rapidly produce accurate, real-time or near real-time, in-situ, orthogonal data for identification of a wide range of chemical compounds. These sensors have the further ability to render simultaneous detection of a broad range of species, and have the capability of simultaneous detection of both positive and negative ions in a sample. Still further surprising is that this can be achieved in a cost-effective, compact, volume-manufacturable package that can operate in the field with low power requirements and yet it is able to generate orthogonal data that can fully identify various a detected species.

Another advantage of the PFAIMS design over prior art cylindrical designs is the ability of the PFAIMS to filter and act on all types of ions with different alpha α dependencies on electric field strength (see background section for more detail on alpha α). This fact allows significant reduction in the complexity of performing measurements in unknown complex sample mixtures.

It will be appreciated by a person skilled in the art that in the prior art cylindrical design shown in FIGS. 12C–D, the radial electric field distribution is non-uniform. Meanwhile, in practice of the present invention, such as the PFAIMS shown in FIGS. 3A,B, the field distribution between the ion filter electrodes (neglecting fringing fields) in the PFAIMS design is uniform and the field is uniform.

It has been found that the time for separation of ions in the planar FAIMS design is significantly less (~10 times) than in the prior art cylindrical FAIMS design when reaching conditions for ion focusing.

However, embodiments of the present invention may be practiced in method and apparatus using cylindrical, planar and other configurations and still remain within the spirit and scope of the present invention. Examples of applications for this invention include use in biological and chemical sensors, and the like. Various modifications of the specific embodiments set forth above are also within the spirit and scope of the invention. The examples disclosed herein are shown by way of illustration and not by way of limitation. The scope of these and other embodiments is limited only as set forth in the following claims.

While this invention has been particularly shown and described with references to preferred embodiments thereof, it will be understood by those skilled in the art that various changes in form and details may be made therein without departing from the scope of the invention encompassed by the appended claims.

What is claimed is:

1. Field asymmetric ion mobility spectrometer apparatus, comprising
   a sample preparation and introduction section, including a head for delivery of ions from a liquid sample, and
   an ion filtering section, an output part and an electronics part,
   said filter section comprising insulating surfaces defining a flow path, further comprising ion filter electrodes facing each other over said flow path, said flow path for the flow of ions between said electrodes, said ions derived from said liquid sample,
   said electronics part configured to apply controlling signals to said electrodes, said electronics part applying an asymmetric periodic signal across said electrodes for generating a filter field having alternating high and low level condition for filtering the flow of said ions in said flow path according to said alternating conditions, and said filter field being compensated to pass desired ion species out of said filter, said passed desired species flowing along said flow path to said output part.

2. Apparatus of claim 1 wherein said insulating surfaces form planar insulating substrates of said filter, wherein said insulating substrates control the gap between the filter electrodes.

3. Apparatus of claim 1 further comprising a planar filter with insulating spacers, wherein the insulating spacers overlap the edges of the filter electrodes.

4. Apparatus of claim 1 wherein said head comprises an electrospray head.

5. Apparatus of claim 4 further comprising desolvation electrodes for desolvation of said ions.

6. Apparatus of claim 4 wherein said electronics part applies symmetric RF signals to said desolvation electrodes, wherein the RF signals provide energy to the ions for raising the ion temperature and enhancing said desolvation.

7. Apparatus of claim 1, further comprising substrates having insulating substrate surfaces, said substrates forming a housing.

8. Apparatus of claim 7 wherein said housing forms a microelectronic chip package.

9. Apparatus of claim 1 further comprising an output section having a plurality of detector electrodes for detecting multiple ion species simultaneously.

10. Apparatus of claim 9 wherein said output section simultaneously detects positively and negatively charged ions.

11. Apparatus of claim 1 further comprising an electrospray head and an attraction electrode, said attraction electrode separated from the ion filter by said substrate to permit applying a different potential to the attraction electrode relative to the ion filter.

12. Apparatus of claim 11 further comprising a FAIMS cylindrical spectrometer package incorporating said surfaces.

13. Apparatus of claim 11 said surfaces further defining a planar surfaced FAIMS spectrometer.

14. Apparatus of claim 11 further comprising guiding electrodes for guiding ions in said flow path.

15. Apparatus of claim 1 comprising a device for generating FAIMS detection data, further comprising a time-offlight measurement device generating TOF detection data, said TOF device combined with said FAIMS device, said head for identification of ion species in said filter via combination of said TOF and FAIMS detection data.

16. Apparatus of claim 15 further comprising a detector for detection of ions passed by said filter, further comprising independently controlled attraction and guiding electrodes, the time of ion travel from said head to said detector being measured using at least one of said electrodes.

17. Apparatus of claim 16 wherein the electrospray assembly can be attached to one of the substrates and guiding electrodes are used to guide the ions into the ionization region.

18. Apparatus of claim 17 further comprising a counter gas flow source to enhance desolvation in said flow path.

19. Apparatus of claim 1 wherein control of which of said ions are filtered is achieved by control by said electronics part of a variable compensation feature and a high field asymmetric waveform radio frequency signal.

20. Apparatus of claim 1 wherein control of which of said ions are filtered is achieved by control by said electronics part of a variable compensation signal and of a high field asymmetric waveform radio frequency signal, wherein said compensation is controlled by varying a feature of the high field asymmetric waveform radio frequency signal.

21. Apparatus of claim 20 wherein said varying a feature includes control of the nature, duty cycle, amplitude, frequency or period of the high field asymmetric waveform radio frequency signal.

22. Apparatus of claim 1 further comprising a spectrometer chip and mounting apparatus, wherein said chip is mountable to a mass spectrometer via said mounting apparatus.

23. Apparatus of claim 22 further comprising a chip carrier, said chip being mounted in said carrier, the carrier enabled for mounting on the inlet of a detector.

24. Apparatus of claim 1 further comprising a detector and a housing, said filter and detector contained in said housing.

25. Apparatus of claim 1 wherein embodiments of the invention enable filtering of molecules after they have been ejected from a source, such as from an electrospray tip or a capillary electrophoresis outlet, and have been ionized prior to filtering via a FAIMS filter, and detected via an internal detector, or via a mass spectrometer or other detector.

26. Apparatus of claim 1 further defining a micromachined electrospray tip within a planar field asymmetric waveform ion mobility spectrometer filter.

27. Apparatus of claim 26 further comprising a device for ion filtering after sample ionization, wherein buffer salt and solvent ions, generated in the electrospray process, are separated from bio-molecules of interest, to provide simplified mass spectra and improved detection limits and identification of said bio-molecules.

28. The apparatus of claim 1 having miniaturized dimensions and formed on a chip.

29. The apparatus of claim 28 wherein the chip is formed with MEMS processes.

30. Apparatus of claim 1 further comprising a mass spectrometer mounting assembly defined at said output part.

31. An ion mobility spectrometer apparatus, comprising:
a high field asymmetric ion mobility spectrometer having an ion filter section, a liquid sample preparation section including an electrospray head, said head receiving, conditioning, and ionizing liquid sample, and an output section, wherein said filter section filters ions from said liquid sample preparation section and passes ion species of interest to said output section to enable species detection and analysis, said sections couple by a common flow path.

32. Apparatus of claim 31 wherein the liquid sample preparation section includes electrospray sample ionization source having a chamber for receipt of liquid sample, and a trap is formed for capture of ions after filtering.

33. Apparatus of claim 31 wherein said spectrometer includes spaced insulated planar substrates, with filter electrodes formed thereon, and the substrates enclosing between themselves said flow path.

34. Apparatus of claim 33 wherein preferably the substrates are insulating or have surfaces for insulated mounting of electrodes facing each other across the flow path.

35. Apparatus of claim 34 wherein the substrates are separated by spacers which may be insulating, wherein the thickness of the spacers defines the distance between the substrates and between the electrodes.

36. Apparatus of claim 31 further comprising spacers as electrodes, apparatus for applying a voltage to said spacer electrodes to confine the ion in the filter within the center of the flow path.

37. Apparatus of claim 36 wherein ions which passed the filter fall on a detector electrode under control of the controller, depending upon the polarity of the detector electrode and the control signals on the detector electrodes, wherein if each detector electrode is held at a different polarity, then multiple ion species can be detected simultaneously, wherein detected ions are correlated with the applied control signals and compensation signals to determine the species of detected ions.

38. Apparatus of claim 31 further comprising insulating spacers that overlap with the edges of filter electrodes to ensure that the ions flowing in the drift tube are confined to a region of uniform transverse electric field between the filter electrodes away from the electrode edges where the non-uniform fringing field is present, and all ions are forced to pass between the filter electrodes, and are subjected to that uniform field.

39. Apparatus of claim 38 wherein some ions are neutralized as they collide with the filter electrodes, said neutralized ions being purged by the carrier gas or purged by heating such as by heating the flow path by applying a current to appropriately configured filter electrodes.

40. Apparatus of claim 39 wherein the flow path is heated by serpentine filter electrodes or resistive spacer electrodes.

41. Apparatus of claim 31 further comprising apparatus to desolvate ions prior to their filtering, such as by applying a heater signal to a heater electrode or by heating the incoming gas flow with a heater element or by applying a generally symmetric RF-electric field to enhance desolvation of ions produced in the electrospray, and preferably as a symmetric radio frequency field applied perpendicularly to the carrier gas flow to cause the ions generated in the electrospray process to oscillate symmetrically, and be heated, as they travel down the drift tube so that the ions are desolvated without net deflection.

42. Apparatus of claim 31 further comprising planar work surfaces for formation of electrodes, which surfaces may be insulating or insulated, such as when formed using glass or ceramic substrates for example in a very compact packaging and with small electrode sizes, the ion filter being defined on these insulated surfaces by the facing filter electrodes with the flow path defined in between, and the insulated surfaces of the substrates in turn isolating the control signals at the filter electrodes from the detector electrodes, for lower noise and improved performance.

43. Apparatus of claim 31 wherein structural electrodes are separated by insulating spacers and the flow path is formed within.

44. Apparatus of claim 31 wherein structural electrodes are separated by insulating spacers and the flow path is formed within, said structural electrodes serving the function of a housing.

45. Apparatus of claim 44 wherein the output section has a top electrode held at a predetermined voltage at the same polarity as the ions of interest passed by the filter while the bottom electrode is held at another level, perhaps at ground and the top electrode deflects ions downward to the bottom electrode for detection.

46. Apparatus of claim 45 wherein either top or bottom electrode may detect ions depending on the ion charge and polarity and the signal applied to the electrodes so that multiple ion species may be detected simultaneously by using top electrode as one detector and bottom electrode as a second detector, and using two different detector circuits, with two different outputs thus being possible at the same time, and thus the detector may detect multiple species passed by the FAIMS filter essentially simultaneously.

47. Apparatus of claim 31 wherein an electronics controller supplies the controlling electronic signals to the system and a control circuit could be on-board, or off-board, where the FAIMS device has at least the leads and contact pads that connect to the control circuit, the signals from the controller being applied to the filter electrodes via such electric leads.

48. Apparatus of claim 31 further comprising forming the electrodes on an insulative substrate, the ion filter electrodes and detector electrodes being positioned closer together to enhance ion collection efficiency and reduce mass that needs to be regulated, heated and controlled.

49. Apparatus of claim 31 further comprising structure that reduces power requirements, including use of small electrodes that reduces capacitance which in turn reduces power consumption, and wherein tightly spaced electrodes enabling a mass production process, since the insulating surfaces of the substrates are a perfect platform for the forming of such electrodes.

50. Apparatus of claim 31 further including a micromachined electrospray head mounted on a substrate and electrodes formed on the substrate 52 to guide the electrospray ions into an ion region of the flow path 30 in the drift tube 29, with an attraction electrode that has a potential applied thereto to attract the ions into the ion region, and a carrier gas flow is set at a desired flow rate to capture ions and to carry them to the filter for the filtering and gas exhaust includes the carrier gas and carries away non-ionized components and neutralized ions.

51. Apparatus of claim 50 wherein potentials applied to electrodes can be set and controlled independent of each other, and enabling attractor electrode to be driven with a different signal than any other electrodes and allowing optimization of ion introduction independent of filter drive requirements.

52. Apparatus of claim 51 wherein guiding electrodes and attractor electrode can be operated in a pulsed mode and wherein a select amount of ions can be introduced into the ion region and wherein the time these ions travel, such as from the orifice to detector, can be used in a TOF-FAIMS mode of operation, wherein the time of flight is associated with ion species, thus providing additional information for species discrimination.

53. Apparatus of claim 1 wherein a major improvement in cylindrical FAIMS devices enables total control of attractor electrode, by isolating the attractor electrode from the filter electrodes.

54. Apparatus of claim 1 wherein an electrospray assembly is attached to a substrate and includes an electrospray head, wherein ions are carried by guiding electrodes toward an orifice and are attracted into ion region in the drift tube by attraction electrode and guiding electrodes.

55. Apparatus of claim 54 wherein preferably a separate DC bias is applied to each guiding electrode to create a potential gradient which guides the ions towards ion region and the guiding electrodes can be used for a further function by also applying symmetric RF signals to enhance desolvation, while gas is introduced to further enhance desolvation flowing opposite to the guided ions exhausting out exhaust ports, preferably operated with no pressure gradient across the orifice.

56. Apparatus of claim 55, in order to improve spray conditions, the separation between the electrospray tip and the top guiding electrode can be adjusted such as by adjusting the position of a housing relative to the base/substrate, which in turn adjusts the separation or in an alternative, the height of the spray head can be adjusted relative to the electrode.

57. Apparatus of claim 1 wherein spaced apart guiding electrodes are bathed in a curtain gas flow which is either unconfined or contained within the local housing, and electrospray head is adjustably mounted in a mount, wherein its angle of delivery can be adjusted relative to the surface of the substrate, and its height can be adjusted relative to the substrate.

58. Apparatus of claim 1 further comprising a microchip having a sample reservoir which receives a liquid sample, which is then ionized and filtered, the chip integrating both an ionization source, such as a microfluidic module, and planar high field asymmetric waveform ion mobility filter.

59. Apparatus of claim 58 wherein various micro-fabricated micro-fluidic components may be used as ion source, or combinations thereof, including electrospray, nano-electrospray, liquid chromatography, electrophoresis separation.

60. Apparatus of claim 58 wherein electrospray head includes sample reservoir feeding a separation channel, leading to spray tip, the channel may be a liquid chromatograph or electrophoretic separator, or the like, for conditioning or separating constituents in the sample prior to ionization at the tip.

61. Apparatus of claim 57 further comprising a chip receiver assembly and the chip is inserted into the receiver in a socket for receipt of the chip, the socket electrically connected to the controller.

62. Apparatus of claim 57 wherein said chip receiver includes a coupling for coupling to a spectrometer, such that the output orifice from the output section is aligned with the MS orifice inlet, whereby ions are directed into the MS inlet for detection and analysis.

63. Apparatus of claim 62 wherein a detector electrode is now used as a deflector electrode to deflect ions toward the intake of the mass spectrometer, the ions are guided or focused by focusing electrodes and pass through an orifice in the substrate and through plenum gas chamber via a mounting adapter.

64. Apparatus of claim 62 further providing a low flow rate plenum gas into chamber to prevent neutralized sample ions or solvent molecules from entering the mass spectrometer intake, and wherein ions that are focused into the mass spectrometer intake are then detected according to standard mass spectrometer procedures.

65. Apparatus of claim 64 wherein ions entering the detector region are focused into the mass spec inlet and this results in a dramatic increase in efficiency of detection and improved sensitivity of the system.

66. Apparatus of claim 1 further comprising a controller that includes several subsystems, including an electrospray control, a waveform generator or synthesizer cooperating with high voltage RF waveform & DC generator for applying the RF asymmetric drive signal and control bias signal to filter electrodes, and detection electronics for detection of ions on the detector electrodes, wherein a computer may collect data and control the system.

67. Apparatus of claim 66 wherein chemical analysis is performed with the assembly is intimately mated via an adapter to a mass spectrometer as a detector and current on focusing electrodes is monitored, to obtain then additional detector information available for processing the detection information of mass spectrometer, and a FAIMS spectra of the invention can be reconstructed by monitoring the total ion current in the mass spectrometer.

68. Apparatus of claim 1 wherein the electrospray tip has been inserted within ion region, either from above through orifice in upper substrate or from the side and attractor electrodes attract and guide the ions in the flow path as they travel in gas flow toward filter electrodes and droplets from the electrospray tip collect in reservoir, which also may be provided with a drain hole.

69. Apparatus of claim 1 further comprising an ion trap, to concentrate ions after they pass through the ion filter and before entering the output section to improve the signal to noise ratio of the detected signal.

70. Apparatus of claim 69 wherein neutrals are not collected in the ion trap and are continuously removed by gas flow from the ion trap.

71. Apparatus of claim 1 further comprising a longitudinal electric field driven embodiment of the invention, for conveying the ions in the drift tube and ions are propelled towards the output section using a longitudinal electric field provided by electrodes, a counter gas flow may be used to clear out and reduce memory effects of previous samples in ion region.

72. Apparatus of claim 71 ions are conveyed without gas flow but rather by action of a longitudinal electric field produced by sets of cooperating electrodes along with a longitudinal RF & DC generator.

73. Apparatus of claim 72 wherein the electrospray tip can be external to the ion region above an orifice where electrode serves as the attraction electrode and in longitudinal electric field driven embodiments, the ion filter includes spaced resistive layers insulated from electrodes, preferably formed on Pyrex substrates, by insulating medium, for example, a low temperature oxide material, and resistive layers are preferably a resistive layer such as a ceramic material deposited on insulating layers, respectively, terminal electrodes make contact with each resistive layer to apply a voltage drop across each resistive layer to generate the longitudinal electric field vector, driven between high and low potentials.

74. Apparatus of claim 73 wherein in a cylindrical design, the electrodes form ring electrodes and resistive layers form a cylinder.

75. Apparatus of claim 1 for performing time of flight ion mobility spectrometry wherein electrodes are pulsed to draw a sample from a tip, starting the time cycle, and electrodes h are biased relative to their neighbors so that the ions are driven by the generated longitudinal electric field gradient towards output section, and a counter gas flow can be applied to sweep sample neutrals away, the possibility of forming an ion trap with a combination of these electrodes.

76. Apparatus of claim 1 having a split gas flow, wherein the electrospray needle is inserted through substrate and into ion region, however, it may be mounted externally to the drift tube, and the ion flow generator in this design includes a plurality of segmented electrodes on opposite sides of flow path to create longitudinal electric field E, and in the preferred embodiment, one or more discrete electrodes are located downstream of gas inlet to extend longitudinal electric field E beyond the split flow of gas, and thereby ensuring that ions flow into filter as carried by drift gas flow stream.

77. Apparatus of claim 76 wherein a mass spectrometer is directly coupled to exhaust port at the end of the drift tube, wherein a baffle may be placed to regulate the velocity of waste gas flow stream relative to the velocity of drift gas flow stream.

78. Apparatus of claim 1 wherein various sample preparation sections can be used, whether simply a port to draw in ambient air samples, or electrospray, gas chromatograph, liquid chromatograph, or the like and a split gas flow prevents clustering and allows better identification of ion species.

79. Apparatus of claim 1 wherein the relationship between the amount of monomer and cluster ions for a given ion species is dependent of the concentration of sample and the particular experimental conditions, which may include moisture, temperature, flow rate, intensity of RF-electric field, and both monomer and cluster states are detected to provide useful information for chemical identification, in a planar two channel FAIMS used to achieve this.

80. Apparatus of claim 79 having a first channel "I" and second channel "II", wherein a curtain gas applied to sample neutrals and they are prevented from entering channel II and ions in the monomer state can be investigated, wherein curtain gasses may flow in the same direction and exhaust at orifice or in opposite directions, while guiding electrodes are included to guide the ions into channel II and an attraction electrode is also used to attract ions into channel II, such that when the curtain gas is turned off ions in the cluster state may be observed since sample neutrals and sample ions may now be drawn into channel II using a pump, and the output section may be connected to a mass spectrometer.

81. Field asymmetric ion mobility spectrometer apparatus, comprising:
sample ion source, and
an ion filtering section, an output part and an electronics part,
said filter section comprising insulating surfaces defining a flow path, further comprising ion filter electrodes facing each other over said flow path, said flow path for the flow of ions between said electrodes, said ions derived from said sample source,
said electronics part configured to apply controlling signals to said electrodes and generating, said electronics part applying an asymmetric periodic signal across said electrodes for generating a filter field having alternating high and low level condition for filtering the flow of said ions in said flow path according to said alternating conditions, and said filter field being compensated to pass desired ion species out of said filter, said passed desired species flowing along said flow path to said output part,
further defining a plurality of integrated micro-fluidic heads with filter parts in a housing, said housing fixing the relative positions of the micro-fluidic heads and filter parts.

82. Apparatus of claim 81 further comprising a disposable array of said integrated micro-fluidic heads with filter parts in a housing.

83. Apparatus of claim 81 wherein said filter section is planar or curved.

84. Field asymmetric ion mobility spectrometer apparatus, comprising:
an ion source an output, a flow path defined between said source and output,
a plurality of ring electrodes and insulator rings, a first set of electrodes and rings forming a first cylinder cooperating with a second cylinder, said flow path defined between said cylinders,
at least two of said electrodes cooperating to define an ion filter, said flow path for the flow of ions in between said electrodes from said source toward said output, and
an electronics part configured to apply controlling signals to said electrodes, said electronics part applying a control signal for filtering the flow of said ions in said flow path according to said signal.

85. Apparatus of claim 84 electronics part configured to apply controlling signals to said electrodes, said electronics part applying an asymmetric periodic signal across said electrodes for generating an alternating high and low field conditions for filtering the flow of said ions in said flow path according to said alternating conditions, and said filter field being compensated to pass desired ion species out of said filter, said passed desired species flowing along said flow path to said output part.

86. Apparatus of claim 85 further defining a sample preparation and introduction section, including a head for the ionization of a liquid sample, said sample being ionized at said ion source.

87. Apparatus of claim 86 wherein said head comprises an electrospray head.

88. Apparatus of claim 87 further comprising spacers, said spacers separating and holding said cylinders in fixed relationship.

89. Apparatus of claim 85 further comprising a set of longitudinal drive field electrodes, said drive field electrodes being driven to generate a longitudinal drive gradient along said flow path to drive ions in said filter toward said output.

90. Apparatus of claim 89 wherein said output further comprises at least one detector electrode for detection of ions passed by said filter.

91. Method for sample separation, including the steps of:
providing sample preparation and introduction section via a head for delivery of ions from a liquid sample,
filtering said ions via an ion filtering section,
providing said filter section with insulating surfaces defining a flow path and ion filter electrodes facing each other over said flow path, said flow path for the flow of said ions between said electrodes, said ions derived from said liquid sample,
providing an electronics part configured to apply controlling signals to said electrodes, said electronics part for applying an asymmetric periodic signal across said electrodes for generating a filter field having alternating high and low level condition for filtering the flow of said ions in said flow path according to said alternating conditions, and said filter field being compensated to pass desired ion species out of said filter, said passed desired species flowing along said flow path to an output part.

92. Method of claim 91 further comprising the steps of forming said insulating surfaces as planar insulating substrates, and controlling the gap between said filter electrodes with said substrates in cooperation.

93. Method of claim 92 further comprising the steps of providing a planar filter with insulating spacers.

94. Method of claim 91 further wherein said head comprises an electrospray head.

95. Method of claim 91 further comprising the steps providing desolvation electrodes, and performing desolvation on said ions with said desolvation electrodes.

96. Method of claim 95 further comprising the step of applying symmetric RF signals to said desolvation electrodes for enhancing said desolvation.

97. Method, in a field asymmetric ion mobility spectrometer, comprising the steps of:
providing a sample ion source, an ion filtering section, an output part,
providing insulating surfaces in said filter section defining a flow path with filter electrodes facing each other over said flow path, said flow path for the flow of ions between said electrodes, said ions derived from said sample source,
providing an electronics part configured to apply controlling signals to said electrodes and generating, said electronics part applying an asymmetric periodic signal across said electrodes for generating a filter field having alternating high and low level condition for filtering the flow of said ions in said flow path according to said alternating conditions, and said filter field being compensated to pass desired ion species out of said filter, said passed desired species flowing along said flow path to said output part, and
defining a plurality of integrated micro-fluidics heads with filter parts in a housing, said housing fixing the relative positions of the micro-fluidic heads and filter parts.

98. Method in a field asymmetric ion mobility spectrometer apparatus with sample preparation and introduction section, ion filtering section, and an output and control section, comprising the steps of providing insulating surfaces, forming said filter section comprising ion filter electrodes facing each other on said insulating surfaces, performing ion filtering after sample ionization, separating bio-molecules of interest in a compensated high-low varying asymmetric RF field, and identifying said bio-molecules based on differences in their ion mobility in high and low varying compensative RF field.

99. A method in a field asymmetric ion mobility spectrometer, comprising the steps of:
providing a sample preparation and introduction section, including a head for delivery of ions from a liquid sample,
providing an ion filtering section and an output part,
providing said filter section with insulating surfaces defining a flow path with ion filter electrodes facing each other over said flow path, said flow path for the flow of ions between said electrodes, said ions derived from said liquid sample,
providing an electronics part configured to apply controlling signals to said electrodes, said electronics part applying an asymmetric periodic signal to said electrodes for generating a filter field having alternating high and low level condition for for filtering the flow of said ions in said flow path according to said alternating conditions, and said filter field being compensated to pass desired ion species out of said filter, said passed desired species flowing along said flow path to said output part, and
providing a compensation control input for the control of a feature of said field to provide said compensation.

* * * * *

UNITED STATES PATENT AND TRADEMARK OFFICE
CERTIFICATE OF CORRECTION

PATENT NO.    : 6,690,004 B2
DATED         : February 10, 2004
INVENTOR(S)   : Raanan A. Miller et al.

It is certified that error appears in the above-identified patent and that said Letters Patent is hereby corrected as shown below:

Column 30,
Line 1, delete "couple" and insert -- coupled --

Signed and Sealed this

Fifteenth Day of June, 2004

JON W. DUDAS
*Acting Director of the United States Patent and Trademark Office*